(12) United States Patent
De Maria et al.

(10) Patent No.: US 7,892,808 B2
(45) Date of Patent: Feb. 22, 2011

(54) PROTEASE VARIANTS

(75) Inventors: Leonardo De Maria, Frederiksberg (DK); Carsten Andersen, Vaerlose (DK); Lars Lehmann Hylling Christensen, Allerod (DK); Soren Flensted Lassen, Farum (DK); Peter Rahbek Ostergaard, Virum (DK)

(73) Assignee: Norozymes A/S, Bagsvaerd (DK)

( * ) Notice: Subject to any disclaimer, the term of this patent is extended or adjusted under 35 U.S.C. 154(b) by 1138 days.

(21) Appl. No.: 10/574,554

(22) PCT Filed: Oct. 8, 2004

(86) PCT No.: PCT/DK2004/000688

§ 371 (c)(1),
(2), (4) Date: Apr. 3, 2006

(87) PCT Pub. No.: WO2005/035747

PCT Pub. Date: Apr. 21, 2005

(65) Prior Publication Data
US 2009/0047387 A1 Feb. 19, 2009

Related U.S. Application Data

(60) Provisional application No. 60/549,347, filed on Mar. 2, 2004, provisional application No. 60/510,450, filed on Oct. 10, 2003.

(30) Foreign Application Priority Data
Oct. 10, 2003 (DK) ............... 2003 01494
Mar. 1, 2004 (DK) ............... 2004 00333

(51) Int. Cl.
C12N 9/52 (2006.01)
C12N 15/57 (2006.01)
C12N 15/74 (2006.01)
C11D 3/386 (2006.01)
A23K 1/165 (2006.01)

(52) U.S. Cl. .............. 435/220; 435/69.1; 435/252.3; 435/320.1; 426/53; 510/300; 536/23.2

(58) Field of Classification Search ............... None
See application file for complete search history.

(56) References Cited

U.S. PATENT DOCUMENTS 3,683,069 A   8/1972   Hooreman (Continued)

FOREIGN PATENT DOCUMENTS

DE   200432   9/1981

(Continued)

OTHER PUBLICATIONS

Derwent Abstract: XP-002310338 Published Aug. 19, 2004.

(Continued)

*Primary Examiner*—Nashaat T Nashed
*Assistant Examiner*—William W Moore
(74) *Attorney, Agent, or Firm*—Elias J. Lambiris

(57) ABSTRACT

The invention relates to a novel 3D structure determined for a *Nocardiopsis* protease, as well as to variants of parent protease homologous to *Nocardiopsis* proteases, preferably of improved thermostability and/or with an altered temperature activity profile. The invention also relates to DNA sequences encoding such variants, their production in a recombinant host cell, as well as methods of using the variants, in particular within the field of animal feed and detergents. The invention further relates to methods of generating and preparing protease variants having different properties.

49 Claims, 26 Drawing Sheets

```
                      1                                                  50
Protease 10   ADIIGGLAYTMGGRCSVGFAATNAAGQPGFVTAGHCGRVGTQVTIGNGRG
Protease 18   ADIIGGLAYYMGGRCSVGFAATNSAGQPGFVTAGHCGTVGTGVTIGNGTG
Protease 11   ADIIGGLAYTMGGRCSVGFAATNAAGQPGFVTAGHCGRVGTQVSIGNGQG
Protease 35   ADIIGGLAYTMGGRCSVGFAATNAAGQPGFVTAGHCGRVGTQVTIGNGRG
Protease 08   ADIIGGLAYTMGGRCSVGFAATNASGQPGFVTAGHCGTVGTPVSIGNGQG
Protease 22   ADIIGGLAYYMGGRCSVGFAATNASGQPGFVTAGHCGTVGTPVSIGNGKG 51                                                 100
Protease 10   VPEQSVPFGNDAAFVRGTSNFTLTNLVSRYNTGGYATVAGHNQAPIGSSV
Protease 18   TFQNSVPFGNDAAFVRGTSNFTLTNLVSRYNSGGYQSVTGTSQAPAGSAV
Protease 11   VFEQSIFPGNDAAFVRGTSNFTLTNLVSRYNTGGYATVAGHNQAPIGSSV
Protease 35   VFEQSIFPGNDAAFVRGTSNFTLTNLVSRYNTGGYATVAGHNQAPIGSSV
Protease 08   VPERSVFPGNDSAFVRGTSNFTLTNLVSRYNTGGYATVSGSSQAAIGSQI
Protease 22   VPERSIFPGNDSAFVRGTSNFTLTNLVSRYNSGGYATVAGHNQAPIGSAV 101                                                 150
Protease 10   CRSGSTTGWHCGTIQARGQSVSYPEGTVTNMTRTTVCAEPGDSGGSYISG
Protease 18   CRSGSTTGWHCGTIQARNQTVRYPQGTVYSLTRTNVCAEPGDSGGSFISG
Protease 11   CRSGSTTGWHCGTIQARGQSVSYPEGTVTNMTRTTVCAEPGDSGGSYISG
Protease 35   CRSGSTTGWHCGTIQARGQSVSYPEGTVTNMTRTTVCAEPGDSGGSYISG
Protease 08   CRSGSTTGWHCGTVQARGQTVSYPQGTVQNLTRTNVCAEPGDSGGSFISG
Protease 22   CRSGSTTGWHCGTIQARNQTVRYPQGTVYSLTRTTVCAEPGDSGGSYISG 151                                 188
Protease 10   TQAQGVTSGGSGNCRTGGTTFYQEVTPMVNSWGVRLRT
Protease 18   SQAQGVTSGGSGNCSVGGTTYYQEVTPMINSWGVRIRT
Protease 11   NQAQGVTSGGSGNCRTGGTTFYQEVTPMVNSWGVRLRT
Protease 35   NQAQGVTSGGSGNCRTGGTTFYQEVTPMVNSWGVRLRT
Protease 08   SQAQGVTSGGSGNCSFGGTTYYQEVNPMLSSWGLTLRT
Protease 22   TQAQGVTSGGSGNCSAGGTTYYQEVNPMLSSWGLTLRT
```

U.S. PATENT DOCUMENTS

| | | | |
|---|---|---|---|
| 3,723,250 A | 3/1973 | Aunstrup et al. | |
| 3,823,072 A | 7/1974 | Hooreman | |
| 3,868,448 A | 2/1975 | Hahn et al. | |
| 3,966,971 A | 6/1976 | Morehouse et al. | |
| 4,073,884 A | 2/1978 | Hartdegen et al. | |
| 4,518,697 A | 5/1985 | Bartnik et al. | |
| 5,047,240 A | 9/1991 | Hooreman | |
| 5,312,748 A | 5/1994 | Liu et al. | |
| 5,646,028 A | 7/1997 | Leigh | |
| 5,705,379 A | 1/1998 | Wilson et al. | |
| 5,811,382 A | 9/1998 | Damhus et al. | |
| 5,877,403 A * | 3/1999 | McMaster et al. | 800/279 |
| 6,855,548 B2 * | 2/2005 | Sjoeholm et al. | 435/422 |
| 7,179,630 B2 | 2/2007 | Lassen et al. | |
| 7,208,310 B2 * | 4/2007 | Lassen et al. | 435/219 |
| 7,485,447 B2 * | 2/2009 | Lassen | 435/220 |
| 7,588,926 B2 * | 9/2009 | Oestergaard et al. | 435/223 |
| 2006/0143738 A1 | 6/2006 | Lassen | |
| 2006/0147499 A1 | 7/2006 | Oestergaard et al. | |
| 2006/0236414 A1 | 10/2006 | Lassen | |
| 2007/0104764 A1 | 5/2007 | Jensen et al. | |
| 2008/0286415 A1 * | 11/2008 | Lassen et al. | 426/63 |

FOREIGN PATENT DOCUMENTS

| | | |
|---|---|---|
| DE | 2004 328 | 5/1983 |
| DK | 0013/96 | 1/1996 |
| EP | 0 130 756 | 1/1985 |
| EP | 0 300 466 | 1/1989 |
| EP | 0 506 448 | 9/1992 |
| EP | 0 516 200 A1 | 12/1992 |
| EP | 0 647 710 | 4/1995 |
| EP | 0 897 985 | 2/1999 |
| JP | 02255081 | 10/1990 |
| JP | 2003284571 | 10/2003 |
| JP | 2004-43660 | 2/2004 |
| WO | WO 88/03947 | 6/1988 |
| WO | WO 91/00345 A1 | 1/1991 |
| WO | WO 91/10723 | 7/1991 |
| WO | WO 92/19729 | 11/1992 |
| WO | WO 95/02044 | 1/1995 |
| WO | WO 95/21540 | 8/1995 |
| WO | WO 95/28850 | 11/1995 |
| WO | WO 96/05739 | 2/1996 |
| WO | WO 98/56260 | 12/1998 |
| WO | WO 99/53038 | 10/1999 |
| WO | WO 01/58276 | 8/2001 |
| WO | WO 2004/070106 | 8/2004 |
| WO | WO 2004/072221 | 8/2004 |
| WO | WO 2004/072279 | 8/2004 |
| WO | WO 2004/111219 | 12/2004 |
| WO | WO 2004/111220 | 12/2004 |
| WO | WO 2004/111221 | 12/2004 |
| WO | WO 2004/111222 | 12/2004 |
| WO | WO 2004/111223 | 12/2004 |
| WO | WO 2004/111224 | 12/2004 |

OTHER PUBLICATIONS

Derwent Abstract: XP-002308395 submitted (Sep. 18, 2002) to the EMBL/GenBankDDBJ databases.

Fagain, Ciaran O., Enzyme and Microbial Technology, vol. 33, pp. 137-149 (2003).
Caine et al., Animal Feed Science Technology, vol. 71, pp. 177-183 (1998).
Gill et al., Analytical Biochemistry, vol. 182, pp. 319-326 (1989).
Michalik et al., Urk. Biokhim. Zh. vol. 69, No. 3, pp. 28-35 (1997) Abstract only.
Needleman et al., Journal of Molecular Biology, vol. 48, pp. 443-453 (1970).
Smith et al., Analytical Biochemistry, vol. 150, pp. 76-85 (1985).
Alschul et al., Seq ID No. 2 Serine Proteinase, GenPept, Acess PQ0104 (1997).
MEROPS Database, Alignment of Subfamily S1E peptidases (2004).
Sidhut et al., The Journal of Biological Chemistry, vol. 269, No. 31, pp. 20167-20171 (1994).
Henderson et al., Journal of Bacteriology, vol. 169, No. 8, pp. 3778-3784 (1987).
Sequence Alignment with protease disclosed in EP 506448, Derwent GenSeq Nucleotide, accession No. AAQ29011 (2004).
Gayle et al., The Journal of Biological Chemistry, vol. 268, No. 29, pp. 22105-22111 (1993).
Whistock et al., Quarterly Reviews of Biophysics, vol. 36, No. 3, pp. 307-340 (2003).
Sequence Alignment of protein disclosed in PCT/DK96/00013, Accession AAW92997 (1999).
Sequence Alignment of protein disclosed in WO 2001/58276, Accession No. AAU07125 (2003).
Sequence Alignment of protein disclosed in PCT/DK96/00013, Accession No. AAX22316 (1999).
Tsuijibo et al., Journal of Applied Bacteriology, vol. 69, No. 4, pp. 520-529 (1990).
Tsuijibo et al., Agric. Biol. Chem. vol. 54 No. 8, pp. 2177-2179 (1990).
Tsuijibo et al., Applied and Environmental Microbiology, vol. 69, No. 2, pp. 894-900 (2003).
Database EMBL, Accession No. AY151208, Nocardiopsis sp. TOA-1 serine protease (napA) gene, complete cds, XP-002308395 (May 16, 2004).
Mitsuiki et al., Enzyme and Microbiol Technology, vol. 34, pp. 482-489 (2004).
Kim et al., Korean Biochemical Journal, vol. 26, No. 1, pp. 81-85 (1993).
Moreira et al., World Journal of Microbiology & Biotechnology, vol. 18, pp. 307-312 (2002).
Higgins et al., Gene, vol. 73, pp. 237-244 (1988).
Kaneda et al., Journal of Biochemistry, vol. 78, pp. 1287-1296 (1975).
Barett et al., Handbook of Proteolytic Enzymes (1998).
Mitsuiki et al., Biosci. Biotechnol. Biochem., vol. 66, No. 1, pp. 164-167 (2002).
Dixit et al., Biochimica et Biophysica Acta, vol. 1523, pp. 261-268 (2000).
Lao et al., Applied and Environmental Microbiology, vol. 62, No. 11, pp. 4256-4259 (1996).
Refstie et al., Aquaculture, vol. 162, pp. 301-312 (1998).
Screen et al., Journal of Biological Chemistry, Vol. 275, No. 9, pp. 6689-6694 (2000).
Heringa et al., Protein Engineering, vol. 8, No. 1, pp. 21-30 (1995).

* cited by examiner

```
            1                                                 50
Protease 10 ADIIGGLAYTMGGRCSVGFAATNAAGQPGFVTAGHCGRVGTQVTIGNGRG
Protease 18 ADIIGGLAYYMGGRCSVGFAATNSAGQPGFVTAGHCGTVGTGVTIGNGTG
Protease 11 ADIIGGLAYTMGGRCSVGFAATNAAGQPGFVTAGHCGRVGTQVSIGNGQG
Protease 35 ADIIGGLAYTMGGRCSVGFAATNAAGQPGFVTAGHCGRVGTQVTIGNGRG
Protease 08 ADIIGGLAYTMGGRCSVGFAATNASGQPGFVTAGHCGTVGTPVSIGNGQG
Protease 22 ADIIGGLAYYMGGRCSVGFAATNASGQPGFVTAGHCGTVGTPVSIGNGKG 51                                                100
Protease 10 VFEQSVFPGNDAAFVRGTSNFTLTNLVSRYNTGGYATVAGHNQAPIGSSV
Protease 18 TFQNSVFPGNDAAFVRGTSNFTLTNLVSRYNSGGYQSVTGTSQAPAGSAV
Protease 11 VFEQSIFPGNDAAFVRGTSNFTLTNLVSRYNTGGYATVAGHNQAPIGSSV
Protease 35 VFEQSIFPGNDAAFVRGTSNFTLTNLVSRYNTGGYATVAGHNQAPIGSSV
Protease 08 VFERSVFPGNDSAFVRGTSNFTLTNLVSRYNTGGYATVSGSSQAAIGSQI
Protease 22 VFERSIFPGNDSAFVRGTSNFTLTNLVSRYNSGGYATVAGHNQAPIGSAV 101                                               150
Protease 10 CRSGSTTGWHCGTIQARGQSVSYPEGTVTNMTRTTVCAEPGDSGGSYISG
Protease 18 CRSGSTTGWHCGTIQARNQTVRYPQGTVYSLTRTNVCAEPGDSGGSFISG
Protease 11 CRSGSTTGWHCGTIQARGQSVSYPEGTVTNMTRTTVCAEPGDSGGSYISG
Protease 35 CRSGSTTGWHCGTIQARGQSVSYPEGTVTNMTRTTVCAEPGDSGGSYISG
Protease 08 CRSGSTTGWHCGTVQARGQTVSYPQGTVQNLTRTNVCAEPGDSGGSFISG
Protease 22 CRSGSTTGWHCGTIQARNQTVRYPQGTVYSLTRTTVCAEPGDSGGSYISG 151                         188
Protease 10 TQAQGVTSGGSGNCRTGGTTFYQEVTPMVNSWGVRLRT
Protease 18 SQAQGVTSGGSGNCSVGGTTYYQEVTPMINSWGVRIRT
Protease 11 NQAQGVTSGGSGNCRTGGTTFYQEVTPMVNSWGVRLRT
Protease 35 NQAQGVTSGGSGNCRTGGTTFYQEVTPMVNSWGVRLRT
Protease 08 SQAQGVTSGGSGNCSFGGTTYYQEVNPMLSSWGLTLRT
Protease 22 TQAQGVTSGGSGNCSAGGTTYYQEVNPMLSSWGLTLRT
```

Fig. 1

| ATOM | 1 | N | ALA | 1 | -18.517 | 32.531 | 28.661 | 1.00 | 8.90 |
|------|---|---|-----|---|---------|--------|--------|------|------|
| ATOM | 2 | CB | ALA | 1 | -18.802 | 30.741 | 30.290 | 1.00 | 12.24 |
| ATOM | 3 | CA | ALA | 1 | -19.308 | 31.313 | 28.965 | 1.00 | 10.86 |
| ATOM | 4 | C | ALA | 1 | -20.783 | 31.666 | 29.080 | 1.00 | 12.18 |
| ATOM | 5 | O | ALA | 1 | -21.113 | 32.695 | 29.712 | 1.00 | 12.73 |
| ATOM | 6 | N | ASP | 2 | -21.722 | 30.930 | 28.510 | 1.00 | 12.01 |
| ATOM | 7 | CA | ASP | 2 | -23.176 | 31.225 | 28.612 | 1.00 | 12.07 |
| ATOM | 8 | C | ASP | 2 | -23.667 | 30.604 | 29.929 | 1.00 | 10.24 |
| ATOM | 9 | O | ASP | 2 | -23.359 | 29.410 | 30.109 | 1.00 | 11.30 |
| ATOM | 10 | CB | ASP | 2 | -23.995 | 30.629 | 27.422 | 1.00 | 12.43 |
| ATOM | 11 | CG | ASP | 2 | -23.545 | 31.314 | 26.129 | 1.00 | 16.23 |
| ATOM | 12 | OD1 | ASP | 2 | -23.300 | 30.668 | 25.134 | 1.00 | 21.68 |
| ATOM | 13 | OD2 | ASP | 2 | -23.346 | 32.527 | 26.168 | 1.00 | 17.64 |
| ATOM | 14 | N | ILE | 3 | -24.387 | 31.321 | 30.757 | 1.00 | 9.80 |
| ATOM | 15 | CA | ILE | 3 | -24.850 | 30.687 | 32.027 | 1.00 | 8.80 |
| ATOM | 16 | C | ILE | 3 | -26.252 | 30.135 | 31.768 | 1.00 | 7.97 |
| ATOM | 17 | O | ILE | 3 | -27.160 | 30.953 | 31.648 | 1.00 | 8.91 |
| ATOM | 18 | CB | ILE | 3 | -24.789 | 31.723 | 33.207 | 1.00 | 7.85 |
| ATOM | 19 | CG1 | ILE | 3 | -23.378 | 32.342 | 33.312 | 1.00 | 5.63 |
| ATOM | 20 | CG2 | ILE | 3 | -25.284 | 31.096 | 34.549 | 1.00 | 4.75 |
| ATOM | 21 | CD1 | ILE | 3 | -22.221 | 31.320 | 33.579 | 1.00 | 5.82 |
| ATOM | 22 | N | ILE | 4 | -26.319 | 28.814 | 31.563 | 1.00 | 7.21 |
| ATOM | 23 | CD1 | ILE | 4 | -26.578 | 27.854 | 27.424 | 1.00 | 8.61 |
| ATOM | 24 | CG1 | ILE | 4 | -27.102 | 28.463 | 28.794 | 1.00 | 8.70 |
| ATOM | 25 | CB | ILE | 4 | -27.272 | 27.363 | 29.888 | 1.00 | 7.20 |
| ATOM | 26 | CG2 | ILE | 4 | -28.446 | 26.419 | 29.544 | 1.00 | 6.35 |
| ATOM | 27 | CA | ILE | 4 | -27.569 | 28.083 | 31.259 | 1.00 | 7.04 |
| ATOM | 28 | C | ILE | 4 | -27.799 | 27.046 | 32.350 | 1.00 | 7.12 |
| ATOM | 29 | O | ILE | 4 | -26.841 | 26.414 | 32.764 | 1.00 | 5.80 |
| ATOM | 30 | N | GLY | 5 | -29.017 | 26.894 | 32.834 | 1.00 | 8.40 |
| ATOM | 31 | CA | GLY | 5 | -29.415 | 25.958 | 33.863 | 1.00 | 5.51 |
| ATOM | 32 | C | GLY | 5 | -29.031 | 24.550 | 33.483 | 1.00 | 6.74 |
| ATOM | 33 | O | GLY | 5 | -29.222 | 24.181 | 32.306 | 1.00 | 8.02 |
| ATOM | 34 | N | GLY | 6 | -28.492 | 23.787 | 34.436 | 1.00 | 5.32 |
| ATOM | 35 | CA | GLY | 6 | -28.113 | 22.385 | 34.125 | 1.00 | 6.51 |
| ATOM | 36 | C | GLY | 6 | -26.697 | 22.143 | 33.678 | 1.00 | 7.67 |
| ATOM | 37 | O | GLY | 6 | -26.264 | 20.957 | 33.687 | 1.00 | 8.08 |
| ATOM | 38 | N | LEU | 7 | -25.941 | 23.127 | 33.235 | 1.00 | 7.02 |
| ATOM | 39 | CD2 | LEU | 7 | -25.075 | 23.250 | 29.859 | 1.00 | 15.01 |
| ATOM | 40 | CD1 | LEU | 7 | -24.009 | 25.544 | 29.892 | 1.00 | 12.10 |
| ATOM | 41 | CG | LEU | 7 | -24.823 | 24.494 | 30.662 | 1.00 | 11.57 |
| ATOM | 42 | CB | LEU | 7 | -24.100 | 24.149 | 31.987 | 1.00 | 7.81 |
| ATOM | 43 | CA | LEU | 7 | -24.543 | 22.889 | 32.774 | 1.00 | 7.23 |
| ATOM | 44 | C | LEU | 7 | -23.543 | 22.624 | 33.891 | 1.00 | 8.17 |
| ATOM | 45 | O | LEU | 7 | -23.779 | 23.055 | 35.054 | 1.00 | 8.83 |
| ATOM | 46 | N | ALA | 8 | -22.450 | 21.931 | 33.560 | 1.00 | 7.85 |
| ATOM | 47 | CB | ALA | 8 | -20.568 | 20.517 | 33.998 | 1.00 | 7.20 |
| ATOM | 48 | CA | ALA | 8 | -21.436 | 21.658 | 34.583 | 1.00 | 6.67 |
| ATOM | 49 | C | ALA | 8 | -20.554 | 22.867 | 34.856 | 1.00 | 8.14 |
| ATOM | 50 | O | ALA | 8 | -20.241 | 23.793 | 34.058 | 1.00 | 7.62 |
| ATOM | 51 | N | TYR | 9 | -20.078 | 22.906 | 36.110 | 1.00 | 6.90 |
| ATOM | 52 | CA | TYR | 9 | -19.074 | 23.854 | 36.602 | 1.00 | 7.03 |
| ATOM | 53 | C | TYR | 9 | -18.138 | 22.960 | 37.480 | 1.00 | 8.21 |
| ATOM | 54 | O | TYR | 9 | -18.560 | 21.945 | 38.048 | 1.00 | 7.61 |

| | | | | | | | | | |
|---|---|---|---|---|---|---|---|---|---|
| ATOM | 55 | CB | TYR | 9 | -19.474 | 25.108 | 37.320 | 1.00 | 7.45 |
| ATOM | 56 | CG | TYR | 9 | -20.138 | 24.925 | 38.664 | 1.00 | 9.14 |
| ATOM | 57 | CD1 | TYR | 9 | -19.401 | 24.898 | 39.853 | 1.00 | 8.86 |
| ATOM | 58 | CD2 | TYR | 9 | -21.559 | 24.818 | 38.673 | 1.00 | 8.66 |
| ATOM | 59 | CE1 | TYR | 9 | -20.044 | 24.756 | 41.062 | 1.00 | 7.11 |
| ATOM | 60 | CE2 | TYR | 9 | -22.214 | 24.696 | 39.930 | 1.00 | 8.78 |
| ATOM | 61 | CZ | TYR | 9 | -21.438 | 24.673 | 41.072 | 1.00 | 7.41 |
| ATOM | 62 | OH | TYR | 9 | -22.115 | 24.537 | 42.248 | 1.00 | 8.28 |
| ATOM | 63 | N | THR | 10 | -16.867 | 23.367 | 37.552 | 1.00 | 8.23 |
| ATOM | 64 | CG2 | THR | 10 | -15.380 | 21.144 | 36.171 | 1.00 | 21.51 |
| ATOM | 65 | OG1 | THR | 10 | -14.022 | 22.954 | 36.816 | 1.00 | 17.27 |
| ATOM | 66 | CB | THR | 10 | -14.816 | 21.869 | 37.398 | 1.00 | 15.54 |
| ATOM | 67 | CA | THR | 10 | -15.881 | 22.592 | 38.334 | 1.00 | 12.22 |
| ATOM | 68 | C | THR | 10 | -15.190 | 23.495 | 39.381 | 1.00 | 12.59 |
| ATOM | 69 | O | THR | 10 | -15.040 | 24.724 | 39.295 | 1.00 | 11.83 |
| ATOM | 70 | N | MET | 11 | -14.719 | 22.854 | 40.422 | 1.00 | 13.86 |
| ATOM | 71 | CE | MET | 11 | -18.117 | 21.521 | 42.992 | 0.70 | 10.20 |
| ATOM | 72 | SD | MET | 11 | -16.364 | 21.817 | 43.260 | 0.70 | 13.92 |
| ATOM | 73 | CG | MET | 11 | -16.351 | 23.607 | 42.742 | 0.70 | 8.87 |
| ATOM | 74 | CB | MET | 11 | -14.945 | 24.074 | 42.557 | 0.70 | 13.60 |
| ATOM | 79 | CA | MET | 11 | -14.003 | 23.423 | 41.576 | 1.00 | 14.74 |
| ATOM | 80 | C | MET | 11 | -13.204 | 22.219 | 42.141 | 1.00 | 16.84 |
| ATOM | 81 | O | MET | 11 | -13.132 | 22.126 | 43.360 | 1.00 | 18.29 |
| ATOM | 82 | N | GLY | 12 | -12.650 | 21.380 | 41.252 | 1.00 | 17.41 |
| ATOM | 83 | CA | GLY | 12 | -11.931 | 20.160 | 41.721 | 1.00 | 20.30 |
| ATOM | 84 | C | GLY | 12 | -12.961 | 19.034 | 41.377 | 1.00 | 22.00 |
| ATOM | 85 | O | GLY | 12 | -12.730 | 18.252 | 40.444 | 1.00 | 25.04 |
| ATOM | 86 | N | GLY | 13 | -14.079 | 19.064 | 42.126 | 1.00 | 17.68 |
| ATOM | 87 | CA | GLY | 13 | -15.219 | 18.171 | 41.900 | 1.00 | 15.21 |
| ATOM | 88 | C | GLY | 13 | -16.127 | 18.873 | 40.846 | 1.00 | 15.26 |
| ATOM | 89 | O | GLY | 13 | -15.681 | 19.862 | 40.228 | 1.00 | 14.61 |
| ATOM | 90 | N | ARG | 14 | -17.370 | 18.410 | 40.657 | 1.00 | 12.77 |
| ATOM | 91 | NH2 | ARG | 14 | -20.479 | 14.276 | 37.036 | 1.00 | 17.15 |
| ATOM | 92 | NH1 | ARG | 14 | -21.587 | 16.075 | 36.340 | 1.00 | 13.21 |
| ATOM | 93 | CZ | ARG | 14 | -20.415 | 15.529 | 36.584 | 1.00 | 16.51 |
| ATOM | 94 | NE | ARG | 14 | -19.265 | 16.236 | 36.423 | 1.00 | 15.10 |
| ATOM | 95 | CD | ARG | 14 | -19.240 | 17.643 | 36.031 | 1.00 | 15.25 |
| ATOM | 96 | CG | ARG | 14 | -19.255 | 18.517 | 37.291 | 1.00 | 14.76 |
| ATOM | 97 | CB | ARG | 14 | -18.333 | 18.056 | 38.435 | 1.00 | 11.53 |
| ATOM | 98 | CA | ARG | 14 | -18.269 | 19.018 | 39.659 | 1.00 | 11.00 |
| ATOM | 99 | C | ARG | 14 | -19.665 | 19.162 | 40.278 | 1.00 | 9.52 |
| ATOM | 100 | O | ARG | 14 | -20.027 | 18.274 | 41.091 | 1.00 | 8.13 |
| ATOM | 101 | N | CYS | 15 | -20.368 | 20.221 | 39.853 | 1.00 | 8.85 |
| ATOM | 102 | CA | CYS | 15 | -21.782 | 20.417 | 40.285 | 1.00 | 6.14 |
| ATOM | 103 | C | CYS | 15 | -22.455 | 21.027 | 39.084 | 1.00 | 6.53 |
| ATOM | 104 | O | CYS | 15 | -21.754 | 21.176 | 38.036 | 1.00 | 8.10 |
| ATOM | 105 | CB | CYS | 15 | -21.897 | 21.271 | 41.568 | 1.00 | 7.27 |
| ATOM | 106 | SG | CYS | 15 | -21.795 | 20.241 | 43.088 | 1.00 | 8.70 |
| ATOM | 107 | N | SER | 16 | -23.746 | 21.368 | 39.154 | 1.00 | 5.13 |
| ATOM | 108 | CA | SER | 16 | -24.402 | 21.936 | 37.975 | 1.00 | 4.73 |
| ATOM | 109 | C | SER | 16 | -24.969 | 23.294 | 38.269 | 1.00 | 6.73 |
| ATOM | 110 | O | SER | 16 | -25.331 | 23.536 | 39.470 | 1.00 | 7.15 |
| ATOM | 111 | CB | SER | 16 | -25.540 | 20.930 | 37.602 | 1.00 | 5.02 |
| ATOM | 112 | OG | SER | 16 | -25.031 | 19.670 | 37.228 | 1.00 | 7.01 |

| | | | | | | | | | |
|---|---|---|---|---|---|---|---|---|---|
| ATOM | 113 | N   | VAL | 17 | -25.177 | 24.129 | 37.276 | 1.00 | 5.71 |
| ATOM | 114 | CA  | VAL | 17 | -25.780 | 25.469 | 37.450 | 1.00 | 6.30 |
| ATOM | 115 | C   | VAL | 17 | -27.274 | 25.365 | 37.742 | 1.00 | 6.27 |
| ATOM | 116 | O   | VAL | 17 | -27.904 | 24.514 | 37.084 | 1.00 | 6.87 |
| ATOM | 117 | CB  | VAL | 17 | -25.589 | 26.211 | 36.113 | 1.00 | 4.80 |
| ATOM | 118 | CG1 | VAL | 17 | -26.252 | 27.572 | 36.079 | 1.00 | 2.00 |
| ATOM | 119 | CG2 | VAL | 17 | -24.108 | 26.435 | 35.892 | 1.00 | 5.56 |
| ATOM | 120 | N   | GLY | 18 | -27.836 | 26.136 | 38.622 | 1.00 | 5.84 |
| ATOM | 121 | CA  | GLY | 18 | -29.277 | 26.067 | 38.899 | 1.00 | 4.89 |
| ATOM | 122 | C   | GLY | 18 | -29.898 | 27.072 | 37.958 | 1.00 | 7.79 |
| ATOM | 123 | O   | GLY | 18 | -30.578 | 26.683 | 36.960 | 1.00 | 8.56 |
| ATOM | 124 | N   | PHE | 19 | -29.783 | 28.366 | 38.175 | 1.00 | 6.84 |
| ATOM | 125 | CA  | PHE | 19 | -30.368 | 29.391 | 37.291 | 1.00 | 8.35 |
| ATOM | 126 | C   | PHE | 19 | -29.457 | 30.625 | 37.254 | 1.00 | 8.67 |
| ATOM | 127 | O   | PHE | 19 | -28.889 | 30.984 | 38.285 | 1.00 | 7.20 |
| ATOM | 128 | CB  | PHE | 19 | -31.761 | 29.873 | 37.827 | 1.00 | 6.74 |
| ATOM | 129 | CG  | PHE | 19 | -32.786 | 28.779 | 38.033 | 1.00 | 8.40 |
| ATOM | 130 | CD1 | PHE | 19 | -33.490 | 28.300 | 36.918 | 1.00 | 9.81 |
| ATOM | 131 | CD2 | PHE | 19 | -32.921 | 28.194 | 39.301 | 1.00 | 8.27 |
| ATOM | 132 | CE1 | PHE | 19 | -34.414 | 27.241 | 37.060 | 1.00 | 7.45 |
| ATOM | 133 | CE2 | PHE | 19 | -33.804 | 27.129 | 39.460 | 1.00 | 7.36 |
| ATOM | 134 | CZ  | PHE | 19 | -34.541 | 26.662 | 38.347 | 1.00 | 8.66 |
| ATOM | 135 | N   | ALA | 20 | -29.375 | 31.284 | 36.114 | 1.00 | 8.32 |
| ATOM | 136 | CB  | ALA | 20 | -28.552 | 32.954 | 34.501 | 1.00 | 7.08 |
| ATOM | 137 | CA  | ALA | 20 | -28.577 | 32.514 | 35.976 | 1.00 | 6.99 |
| ATOM | 138 | C   | ALA | 20 | -29.347 | 33.558 | 36.793 | 1.00 | 8.39 |
| ATOM | 139 | O   | ALA | 20 | -30.614 | 33.548 | 36.744 | 1.00 | 6.62 |
| ATOM | 140 | N   | ALA | 21 | -28.653 | 34.461 | 37.453 | 1.00 | 6.45 |
| ATOM | 141 | CB  | ALA | 21 | -29.774 | 34.943 | 39.600 | 1.00 | 6.04 |
| ATOM | 142 | CA  | ALA | 21 | -29.305 | 35.514 | 38.244 | 1.00 | 9.09 |
| ATOM | 143 | C   | ALA | 21 | -28.267 | 36.598 | 38.599 | 1.00 | 10.25 |
| ATOM | 144 | O   | ALA | 21 | -27.048 | 36.412 | 38.434 | 1.00 | 10.39 |
| ATOM | 145 | N   | THR | 22 | -28.734 | 37.704 | 39.154 | 1.00 | 10.87 |
| ATOM | 146 | CA  | THR | 22 | -27.795 | 38.747 | 39.633 | 1.00 | 9.81 |
| ATOM | 147 | C   | THR | 22 | -28.044 | 38.773 | 41.139 | 1.00 | 12.70 |
| ATOM | 148 | O   | THR | 22 | -29.153 | 38.378 | 41.607 | 1.00 | 13.28 |
| ATOM | 149 | CB  | THR | 22 | -28.009 | 40.191 | 39.000 | 1.00 | 12.32 |
| ATOM | 150 | OG1 | THR | 22 | -29.443 | 40.520 | 39.201 | 1.00 | 17.96 |
| ATOM | 151 | CG2 | THR | 22 | -27.730 | 40.314 | 37.512 | 1.00 | 10.22 |
| ATOM | 152 | N   | ASN | 23 | -27.067 | 39.261 | 41.919 | 1.00 | 12.56 |
| ATOM | 153 | ND2 | ASN | 23 | -23.651 | 39.789 | 44.187 | 1.00 | 14.15 |
| ATOM | 154 | OD1 | ASN | 23 | -25.034 | 41.090 | 43.182 | 1.00 | 11.99 |
| ATOM | 155 | CG  | ASN | 23 | -24.917 | 40.044 | 43.825 | 1.00 | 13.60 |
| ATOM | 156 | CB  | ASN | 23 | -26.025 | 39.065 | 44.153 | 1.00 | 12.41 |
| ATOM | 157 | CA  | ASN | 23 | -27.308 | 39.367 | 43.381 | 1.00 | 14.31 |
| ATOM | 158 | C   | ASN | 23 | -27.947 | 40.754 | 43.600 | 1.00 | 15.71 |
| ATOM | 159 | O   | ASN | 23 | -28.252 | 41.558 | 42.664 | 1.00 | 13.68 |
| ATOM | 160 | N   | ALA | 24 | -28.043 | 41.088 | 44.883 | 1.00 | 16.68 |
| ATOM | 161 | CB  | ALA | 24 | -28.899 | 42.370 | 46.862 | 1.00 | 19.20 |
| ATOM | 162 | CA  | ALA | 24 | -28.626 | 42.344 | 45.371 | 1.00 | 20.06 |
| ATOM | 163 | C   | ALA | 24 | -27.831 | 43.543 | 44.936 | 1.00 | 22.43 |
| ATOM | 164 | O   | ALA | 24 | -28.408 | 44.658 | 44.795 | 1.00 | 24.93 |
| ATOM | 165 | N   | ALA | 25 | -26.556 | 43.412 | 44.648 | 1.00 | 23.59 |
| ATOM | 166 | CA  | ALA | 25 | -25.727 | 44.513 | 44.128 | 1.00 | 20.79 |

| | | | | | | | | |
|---|---|---|---|---|---|---|---|---|
| ATOM | 167 | C | ALA | 25 | -25.765 | 44.542 | 42.613 | 1.00 21.34 |
| ATOM | 168 | O | ALA | 25 | -25.018 | 45.388 | 42.040 | 1.00 24.26 |
| ATOM | 169 | CB | ALA | 25 | -24.278 | 44.379 | 44.584 | 1.00 24.28 |
| ATOM | 170 | N | GLY | 26 | -26.508 | 43.687 | 41.910 | 1.00 16.97 |
| ATOM | 171 | CA | GLY | 26 | -26.453 | 43.763 | 40.456 | 1.00 15.31 |
| ATOM | 172 | C | GLY | 26 | -25.320 | 43.024 | 39.803 | 1.00 13.98 |
| ATOM | 173 | O | GLY | 26 | -25.158 | 43.168 | 38.560 | 1.00 15.90 |
| ATOM | 174 | N | GLN | 27 | -24.594 | 42.196 | 40.523 | 1.00 13.26 |
| ATOM | 175 | NE2 | GLN | 27 | -19.688 | 42.607 | 42.319 | 1.00 23.84 |
| ATOM | 176 | OE1 | GLN | 27 | -21.306 | 41.674 | 43.669 | 1.00 19.08 |
| ATOM | 177 | CD | GLN | 27 | -20.952 | 42.234 | 42.626 | 1.00 20.42 |
| ATOM | 178 | CG | GLN | 27 | -21.934 | 42.487 | 41.519 | 1.00 16.87 |
| ATOM | 179 | CB | GLN | 27 | -22.364 | 41.130 | 40.909 | 1.00 13.66 |
| ATOM | 180 | CA | GLN | 27 | -23.488 | 41.430 | 39.904 | 1.00 11.98 |
| ATOM | 181 | C | GLN | 27 | -24.023 | 40.113 | 39.345 | 1.00 11.67 |
| ATOM | 182 | O | GLN | 27 | -24.829 | 39.428 | 39.949 | 1.00 11.63 |
| ATOM | 183 | N | PRO | 28 | -23.539 | 39.714 | 38.197 | 1.00 10.36 |
| ATOM | 184 | CG | PRO | 28 | -22.111 | 39.444 | 36.367 | 1.00 11.95 |
| ATOM | 185 | CD | PRO | 28 | -22.544 | 40.519 | 37.403 | 1.00 10.61 |
| ATOM | 186 | CB | PRO | 28 | -23.429 | 38.692 | 36.116 | 1.00 11.06 |
| ATOM | 187 | CA | PRO | 28 | -23.977 | 38.497 | 37.537 | 1.00 9.08 |
| ATOM | 188 | C | PRO | 28 | -23.418 | 37.248 | 38.194 | 1.00 9.80 |
| ATOM | 189 | O | PRO | 28 | -22.278 | 37.282 | 38.749 | 1.00 9.50 |
| ATOM | 190 | N | GLY | 29 | -24.245 | 36.179 | 38.101 | 1.00 6.29 |
| ATOM | 191 | CA | GLY | 29 | -23.721 | 34.885 | 38.671 | 1.00 4.48 |
| ATOM | 192 | C | GLY | 29 | -24.827 | 33.875 | 38.440 | 1.00 6.36 |
| ATOM | 193 | O | GLY | 29 | -25.604 | 34.036 | 37.454 | 1.00 7.58 |
| ATOM | 194 | N | PHE | 30 | -24.889 | 32.917 | 39.339 | 1.00 7.28 |
| ATOM | 195 | CA | PHE | 30 | -25.971 | 31.891 | 39.292 | 1.00 7.77 |
| ATOM | 196 | C | PHE | 30 | -26.232 | 31.306 | 40.703 | 1.00 6.83 |
| ATOM | 197 | O | PHE | 30 | -25.281 | 31.334 | 41.532 | 1.00 8.49 |
| ATOM | 198 | CB | PHE | 30 | -25.653 | 30.741 | 38.312 | 1.00 3.78 |
| ATOM | 199 | CG | PHE | 30 | -24.384 | 29.955 | 38.483 | 1.00 5.51 |
| ATOM | 200 | CD1 | PHE | 30 | -24.299 | 28.836 | 39.311 | 1.00 5.54 |
| ATOM | 201 | CD2 | PHE | 30 | -23.251 | 30.336 | 37.752 | 1.00 8.26 |
| ATOM | 202 | CE1 | PHE | 30 | -23.126 | 28.108 | 39.451 | 1.00 8.21 |
| ATOM | 203 | CE2 | PHE | 30 | -21.996 | 29.661 | 37.898 | 1.00 6.20 |
| ATOM | 204 | CZ | PHE | 30 | -21.971 | 28.509 | 38.739 | 1.00 7.61 |
| ATOM | 205 | N | VAL | 31 | -27.413 | 30.739 | 40.862 | 1.00 4.85 |
| ATOM | 206 | CA | VAL | 31 | -27.751 | 30.017 | 42.118 | 1.00 6.26 |
| ATOM | 207 | C | VAL | 31 | -27.445 | 28.530 | 41.828 | 1.00 6.68 |
| ATOM | 208 | O | VAL | 31 | -27.515 | 28.036 | 40.680 | 1.00 4.79 |
| ATOM | 209 | CB | VAL | 31 | -29.141 | 30.296 | 42.666 | 1.00 7.03 |
| ATOM | 210 | CG1 | VAL | 31 | -29.230 | 31.765 | 43.136 | 1.00 11.46 |
| ATOM | 211 | CG2 | VAL | 31 | -30.190 | 29.902 | 41.646 | 1.00 8.54 |
| ATOM | 212 | N | THR | 32 | -27.150 | 27.786 | 42.910 | 1.00 5.51 |
| ATOM | 213 | CA | THR | 32 | -26.762 | 26.373 | 42.892 | 1.00 7.30 |
| ATOM | 214 | C | THR | 32 | -26.833 | 25.866 | 44.356 | 1.00 8.85 |
| ATOM | 215 | O | THR | 32 | -27.382 | 26.568 | 45.240 | 1.00 6.58 |
| ATOM | 216 | CB | THR | 32 | -25.318 | 26.271 | 42.249 | 1.00 6.85 |
| ATOM | 217 | OG1 | THR | 32 | -24.927 | 24.904 | 42.030 | 1.00 6.22 |
| ATOM | 218 | CG2 | THR | 32 | -24.141 | 26.895 | 43.109 | 1.00 4.90 |
| ATOM | 219 | N | ALA | 33 | -26.318 | 24.676 | 44.619 | 1.00 8.92 |
| ATOM | 220 | CA | ALA | 33 | -26.313 | 24.007 | 45.928 | 1.00 9.53 |

| ATOM | 221 | C | ALA | 33 | -25.158 | 24.465 | 46.827 | 1.00 | 9.16 |
| --- | --- | --- | --- | --- | --- | --- | --- | --- | --- |
| ATOM | 222 | O | ALA | 33 | -24.007 | 24.503 | 46.369 | 1.00 | 8.53 |
| ATOM | 223 | CB | ALA | 33 | -26.294 | 22.473 | 45.773 | 1.00 | 7.77 |
| ATOM | 224 | N | GLY | 34 | -25.408 | 24.724 | 48.076 | 1.00 | 7.16 |
| ATOM | 225 | CA | GLY | 34 | -24.348 | 25.143 | 49.024 | 1.00 | 8.05 |
| ATOM | 226 | C | GLY | 34 | -23.390 | 24.043 | 49.347 | 1.00 | 7.39 |
| ATOM | 227 | O | GLY | 34 | -22.194 | 24.315 | 49.698 | 1.00 | 8.30 |
| ATOM | 228 | N | HIS | 35 | -23.788 | 22.780 | 49.271 | 1.00 | 7.52 |
| ATOM | 229 | CA | HIS | 35 | -22.821 | 21.714 | 49.636 | 1.00 | 6.58 |
| ATOM | 230 | C | HIS | 35 | -21.744 | 21.601 | 48.560 | 1.00 | 8.95 |
| ATOM | 231 | O | HIS | 35 | -20.702 | 20.945 | 48.747 | 1.00 | 8.96 |
| ATOM | 232 | CB | HIS | 35 | -23.497 | 20.364 | 49.883 | 1.00 | 8.85 |
| ATOM | 233 | CG | HIS | 35 | -23.991 | 19.599 | 48.686 | 1.00 | 6.87 |
| ATOM | 234 | ND1 | HIS | 35 | -25.305 | 19.481 | 48.321 | 1.00 | 8.56 |
| ATOM | 235 | CD2 | HIS | 35 | -23.326 | 18.872 | 47.769 | 1.00 | 5.55 |
| ATOM | 236 | CE1 | HIS | 35 | -25.414 | 18.744 | 47.228 | 1.00 | 7.54 |
| ATOM | 237 | NE2 | HIS | 35 | -24.217 | 18.313 | 46.906 | 1.00 | 8.64 |
| ATOM | 238 | N | CYS | 36 | -21.930 | 22.183 | 47.376 | 1.00 | 8.15 |
| ATOM | 239 | CA | CYS | 36 | -20.940 | 22.145 | 46.312 | 1.00 | 8.05 |
| ATOM | 240 | C | CYS | 36 | -19.746 | 23.062 | 46.679 | 1.00 | 11.13 |
| ATOM | 241 | O | CYS | 36 | -18.715 | 22.841 | 45.999 | 1.00 | 10.34 |
| ATOM | 242 | CB | CYS | 36 | -21.518 | 22.598 | 44.977 | 1.00 | 5.97 |
| ATOM | 243 | SG | CYS | 36 | -22.774 | 21.389 | 44.403 | 1.00 | 9.16 |
| ATOM | 244 | N | GLY | 37 | -19.855 | 24.012 | 47.601 | 1.00 | 9.60 |
| ATOM | 245 | CA | GLY | 37 | -18.632 | 24.821 | 47.862 | 1.00 | 8.52 |
| ATOM | 246 | C | GLY | 37 | -18.853 | 25.793 | 48.998 | 1.00 | 11.72 |
| ATOM | 247 | O | GLY | 37 | -19.923 | 26.350 | 49.153 | 1.00 | 12.57 |
| ATOM | 248 | N | ARG | 38 | -17.807 | 26.044 | 49.767 | 1.00 | 9.44 |
| ATOM | 249 | NH2 | ARG | 38 | -13.066 | 27.478 | 54.730 | 0.00 | 41.69 |
| ATOM | 250 | NH1 | ARG | 38 | -14.258 | 25.862 | 55.765 | 0.00 | 42.03 |
| ATOM | 251 | CZ | ARG | 38 | -13.968 | 26.494 | 54.619 | 0.00 | 41.38 |
| ATOM | 252 | NE | ARG | 38 | -14.559 | 26.142 | 53.467 | 0.00 | 39.87 |
| ATOM | 253 | CD | ARG | 38 | -15.763 | 25.165 | 53.320 | 0.00 | 37.50 |
| ATOM | 254 | CG | ARG | 38 | -17.064 | 25.666 | 52.814 | 1.00 | 23.13 |
| ATOM | 255 | CB | ARG | 38 | -16.602 | 26.727 | 51.799 | 1.00 | 14.90 |
| ATOM | 256 | CA | ARG | 38 | -17.812 | 27.040 | 50.845 | 1.00 | 12.65 |
| ATOM | 257 | C | ARG | 38 | -17.566 | 28.415 | 50.239 | 1.00 | 11.84 |
| ATOM | 258 | O | ARG | 38 | -16.987 | 28.562 | 49.137 | 1.00 | 10.80 |
| ATOM | 259 | N | VAL | 39 | -17.953 | 29.488 | 50.953 | 1.00 | 12.22 |
| ATOM | 260 | CA | VAL | 39 | -17.723 | 30.881 | 50.483 | 1.00 | 11.55 |
| ATOM | 261 | C | VAL | 39 | -16.224 | 31.002 | 50.149 | 1.00 | 11.46 |
| ATOM | 262 | O | VAL | 39 | -15.406 | 30.540 | 50.944 | 1.00 | 12.65 |
| ATOM | 263 | CB | VAL | 39 | -18.195 | 31.902 | 51.513 | 1.00 | 14.37 |
| ATOM | 264 | CG1 | VAL | 39 | -17.541 | 33.262 | 51.282 | 1.00 | 18.26 |
| ATOM | 265 | CG2 | VAL | 39 | -19.720 | 32.035 | 51.617 | 1.00 | 19.01 |
| ATOM | 266 | N | GLY | 40 | -15.853 | 31.595 | 49.017 | 1.00 | 10.59 |
| ATOM | 267 | CA | GLY | 40 | -14.467 | 31.715 | 48.658 | 1.00 | 9.21 |
| ATOM | 268 | C | GLY | 40 | -13.962 | 30.690 | 47.689 | 1.00 | 11.61 |
| ATOM | 269 | O | GLY | 40 | -12.904 | 30.954 | 47.066 | 1.00 | 13.99 |
| ATOM | 270 | N | THR | 41 | -14.603 | 29.592 | 47.441 | 1.00 | 10.26 |
| ATOM | 271 | CG2 | THR | 41 | -14.886 | 26.180 | 45.550 | 1.00 | 8.90 |
| ATOM | 272 | OG1 | THR | 41 | -15.058 | 26.792 | 47.930 | 1.00 | 14.49 |
| ATOM | 273 | CB | THR | 41 | -15.123 | 27.285 | 46.571 | 1.00 | 12.41 |
| ATOM | 274 | CA | THR | 41 | -14.199 | 28.566 | 46.525 | 1.00 | 9.98 |

| ATOM | 275 | C   | THR | 41 | -14.360 | 29.148 | 45.121 | 1.00 | 11.13 |
|------|-----|-----|-----|----|---------|--------|--------|------|-------|
| ATOM | 276 | O   | THR | 41 | -15.404 | 29.657 | 44.713 | 1.00 | 10.17 |
| ATOM | 277 | N   | GLN | 42 | -13.297 | 28.983 | 44.365 | 1.00 | 12.36 |
| ATOM | 278 | NE2 | GLN | 42 | -11.317 | 32.840 | 43.178 | 0.70 | 32.68 |
| ATOM | 279 | OE1 | GLN | 42 | -9.407  | 31.714 | 42.552 | 0.70 | 35.48 |
| ATOM | 280 | CD  | GLN | 42 | -10.512 | 31.791 | 43.080 | 0.70 | 30.29 |
| ATOM | 281 | CG  | GLN | 42 | -11.132 | 30.558 | 43.680 | 0.70 | 24.69 |
| ATOM | 282 | CB  | GLN | 42 | -11.801 | 29.729 | 42.592 | 0.70 | 18.80 |
| ATOM | 288 | CA  | GLN | 42 | -13.263 | 29.456 | 42.977 | 1.00 | 11.77 |
| ATOM | 289 | C   | GLN | 42 | -13.852 | 28.392 | 42.063 | 1.00 | 13.86 |
| ATOM | 290 | O   | GLN | 42 | -13.615 | 27.187 | 42.330 | 1.00 | 12.07 |
| ATOM | 291 | N   | VAL | 43 | -14.544 | 28.817 | 41.002 | 1.00 | 13.96 |
| ATOM | 292 | CG2 | VAL | 43 | -17.397 | 28.751 | 39.309 | 1.00 | 15.91 |
| ATOM | 293 | CG1 | VAL | 43 | -17.192 | 27.656 | 41.542 | 1.00 | 10.29 |
| ATOM | 294 | CB  | VAL | 43 | -16.657 | 27.731 | 40.117 | 1.00 | 14.08 |
| ATOM | 295 | CA  | VAL | 43 | -15.132 | 27.886 | 40.018 | 1.00 | 11.05 |
| ATOM | 296 | C   | VAL | 43 | -14.717 | 28.297 | 38.584 | 1.00 | 10.70 |
| ATOM | 297 | O   | VAL | 43 | -14.393 | 29.467 | 38.214 | 1.00 | 8.75  |
| ATOM | 298 | N   | THR | 44 | -14.726 | 27.266 | 37.757 | 1.00 | 8.19  |
| ATOM | 299 | CG2 | THR | 44 | -13.085 | 26.655 | 34.277 | 1.00 | 16.80 |
| ATOM | 300 | OG1 | THR | 44 | -12.054 | 27.080 | 36.423 | 1.00 | 14.72 |
| ATOM | 301 | CB  | THR | 44 | -13.232 | 26.536 | 35.773 | 1.00 | 7.96  |
| ATOM | 302 | CA  | THR | 44 | -14.459 | 27.387 | 36.328 | 1.00 | 8.95  |
| ATOM | 303 | C   | THR | 44 | -15.708 | 26.877 | 35.588 | 1.00 | 10.78 |
| ATOM | 304 | O   | THR | 44 | -16.155 | 25.743 | 35.947 | 1.00 | 9.00  |
| ATOM | 305 | N   | ILE | 45 | -16.219 | 27.660 | 34.626 | 1.00 | 10.77 |
| ATOM | 306 | CA  | ILE | 45 | -17.352 | 27.175 | 33.850 | 1.00 | 11.78 |
| ATOM | 307 | C   | ILE | 45 | -16.950 | 27.476 | 32.396 | 1.00 | 10.56 |
| ATOM | 308 | O   | ILE | 45 | -16.976 | 28.673 | 32.030 | 1.00 | 10.62 |
| ATOM | 309 | CB  | ILE | 45 | -18.743 | 27.767 | 34.312 | 1.00 | 8.73  |
| ATOM | 310 | CG1 | ILE | 45 | -19.767 | 27.359 | 33.217 | 1.00 | 14.25 |
| ATOM | 311 | CG2 | ILE | 45 | -18.635 | 29.300 | 34.483 | 1.00 | 14.91 |
| ATOM | 312 | CD1 | ILE | 45 | -21.239 | 27.351 | 33.717 | 1.00 | 17.74 |
| ATOM | 313 | N   | GLY | 46 | -16.588 | 26.493 | 31.623 | 1.00 | 11.49 |
| ATOM | 314 | CA  | GLY | 46 | -16.162 | 26.796 | 30.214 | 1.00 | 13.72 |
| ATOM | 315 | C   | GLY | 46 | -15.009 | 27.812 | 30.282 | 1.00 | 12.34 |
| ATOM | 316 | O   | GLY | 46 | -14.011 | 27.661 | 31.002 | 1.00 | 14.15 |
| ATOM | 317 | N   | ASN | 47 | -15.134 | 28.895 | 29.512 | 1.00 | 13.14 |
| ATOM | 318 | ND2 | ASN | 47 | -15.075 | 31.342 | 26.221 | 1.00 | 26.89 |
| ATOM | 319 | OD1 | ASN | 47 | -16.257 | 31.266 | 28.086 | 1.00 | 18.12 |
| ATOM | 320 | CG  | ASN | 47 | -15.180 | 31.045 | 27.520 | 1.00 | 19.67 |
| ATOM | 321 | CB  | ASN | 47 | -13.914 | 30.476 | 28.081 | 1.00 | 17.20 |
| ATOM | 322 | CA  | ASN | 47 | -14.106 | 29.967 | 29.522 | 1.00 | 14.86 |
| ATOM | 323 | C   | ASN | 47 | -14.409 | 31.129 | 30.484 | 1.00 | 14.20 |
| ATOM | 324 | O   | ASN | 47 | -13.929 | 32.264 | 30.367 | 1.00 | 16.69 |
| ATOM | 325 | N   | GLY | 48 | -15.234 | 30.900 | 31.476 | 1.00 | 11.79 |
| ATOM | 326 | CA  | GLY | 48 | -15.629 | 31.860 | 32.487 | 1.00 | 10.60 |
| ATOM | 327 | C   | GLY | 48 | -15.114 | 31.350 | 33.840 | 1.00 | 8.68  |
| ATOM | 328 | O   | GLY | 48 | -14.741 | 30.180 | 34.021 | 1.00 | 8.85  |
| ATOM | 329 | N   | ARG | 49 | -15.067 | 32.286 | 34.782 | 1.00 | 8.71  |
| ATOM | 330 | NH2 | ARG | 49 | -10.753 | 29.684 | 38.714 | 0.00 | 43.61 |
| ATOM | 331 | NH1 | ARG | 49 | -9.430  | 30.717 | 37.086 | 0.00 | 39.51 |
| ATOM | 332 | CZ  | ARG | 49 | -10.647 | 30.223 | 37.466 | 0.00 | 42.12 |
| ATOM | 333 | NE  | ARG | 49 | -11.803 | 30.174 | 36.714 | 0.00 | 38.98 |

```
ATOM    334  CD   ARG    49     -11.625  30.774  35.625  1.00  24.44
ATOM    335  CG   ARG    49     -12.079  32.161  35.395  1.00  20.17
ATOM    336  CB   ARG    49     -13.190  32.537  36.355  1.00  13.15
ATOM    337  CA   ARG    49     -14.600  31.985  36.143  1.00   8.87
ATOM    338  C    ARG    49     -15.485  32.746  37.136  1.00   9.56
ATOM    339  O    ARG    49     -16.026  33.814  36.747  1.00  10.73
ATOM    340  N    GLY    50     -15.644  32.236  38.337  1.00  10.04
ATOM    341  CA   GLY    50     -16.416  32.933  39.372  1.00   6.68
ATOM    342  C    GLY    50     -15.985  32.438  40.758  1.00   7.46
ATOM    343  O    GLY    50     -15.035  31.654  40.838  1.00   8.57
ATOM    344  N    VAL    51     -16.755  32.885  41.756  1.00   9.13
ATOM    345  CG2  VAL    51     -15.047  33.181  45.219  1.00   9.31
ATOM    346  CG1  VAL    51     -16.041  34.936  43.760  1.00   9.54
ATOM    347  CB   VAL    51     -15.469  33.510  43.768  1.00  10.40
ATOM    348  CA   VAL    51     -16.439  32.474  43.145  1.00   8.97
ATOM    349  C    VAL    51     -17.739  32.363  43.951  1.00   8.46
ATOM    350  O    VAL    51     -18.657  33.166  43.726  1.00   8.01
ATOM    351  N    PHE    52     -17.778  31.394  44.846  1.00   7.71
ATOM    352  CD2  PHE    52     -20.510  28.198  46.287  1.00   7.34
ATOM    353  CE2  PHE    52     -20.952  27.038  45.614  1.00  12.48
ATOM    354  CZ   PHE    52     -20.103  26.415  44.672  1.00  11.92
ATOM    355  CE1  PHE    52     -18.857  26.983  44.355  1.00   8.56
ATOM    356  CD1  PHE    52     -18.454  28.151  45.012  1.00   7.30
ATOM    357  CG   PHE    52     -19.269  28.765  45.964  1.00  10.46
ATOM    358  CB   PHE    52     -18.820  30.015  46.703  1.00   9.22
ATOM    359  CA   PHE    52     -18.916  31.237  45.766  1.00   9.28
ATOM    360  C    PHE    52     -18.928  32.498  46.637  1.00  10.41
ATOM    361  O    PHE    52     -17.979  32.752  47.403  1.00  10.33
ATOM    362  N    GLU    53     -20.038  33.239  46.481  1.00   8.81
ATOM    363  OE2  GLU    53     -22.012  37.756  45.426  1.00  27.06
ATOM    364  OE1  GLU    53     -21.229  39.265  46.722  1.00  33.78
ATOM    365  CD   GLU    53     -21.338  38.087  46.413  1.00  28.63
ATOM    366  CG   GLU    53     -20.701  36.961  47.162  1.00  15.08
ATOM    367  CB   GLU    53     -20.818  35.612  46.441  1.00  10.91
ATOM    368  CA   GLU    53     -20.172  34.475  47.239  1.00  10.55
ATOM    369  C    GLU    53     -21.035  34.208  48.485  1.00  13.01
ATOM    370  O    GLU    53     -20.664  34.743  49.558  1.00  11.89
ATOM    371  N    GLN    54     -22.095  33.444  48.352  1.00   9.12
ATOM    372  NE2  GLN    54     -26.256  36.329  49.251  1.00  43.84
ATOM    373  OE1  GLN    54     -25.933  35.594  51.419  1.00  46.53
ATOM    374  CD   GLN    54     -25.586  35.741  50.241  1.00  40.72
ATOM    375  CG   GLN    54     -24.256  35.205  49.756  1.00  29.81
ATOM    376  CB   GLN    54     -24.346  33.707  49.555  1.00  17.82
ATOM    377  CA   GLN    54     -22.955  33.105  49.508  1.00  10.81
ATOM    378  C    GLN    54     -23.164  31.600  49.527  1.00  12.82
ATOM    379  O    GLN    54     -23.418  31.101  48.410  1.00  13.75
ATOM    380  N    SER    55     -23.074  30.926  50.665  1.00  10.56
ATOM    381  OG   SER    55     -22.169  27.372  50.204  1.00  14.02
ATOM    382  CB   SER    55     -21.995  28.781  50.228  1.00   9.88
ATOM    383  CA   SER    55     -23.280  29.470  50.637  1.00  11.20
ATOM    384  C    SER    55     -23.730  28.998  52.014  1.00  12.70
ATOM    385  O    SER    55     -23.084  29.298  53.011  1.00  11.84
ATOM    386  N    VAL    56     -24.824  28.274  52.086  1.00  11.38
ATOM    387  CA   VAL    56     -25.345  27.735  53.342  1.00   9.56
```

| | | | | | | | | | |
|---|---|---|---|---|---|---|---|---|---|
| ATOM | 388 | C | VAL | 56 | -25.516 | 26.223 | 53.218 | 1.00 | 11.47 |
| ATOM | 389 | O | VAL | 56 | -26.250 | 25.756 | 52.302 | 1.00 | 10.80 |
| ATOM | 390 | CB | VAL | 56 | -26.691 | 28.365 | 53.715 | 1.00 | 12.57 |
| ATOM | 391 | CG1 | VAL | 56 | -27.250 | 27.561 | 54.895 | 1.00 | 13.65 |
| ATOM | 392 | CG2 | VAL | 56 | -26.542 | 29.809 | 54.111 | 1.00 | 14.61 |
| ATOM | 393 | N | PHE | 57 | -24.903 | 25.475 | 54.116 | 1.00 | 9.44 |
| ATOM | 394 | CA | PHE | 57 | -25.035 | 24.030 | 54.173 | 1.00 | 10.86 |
| ATOM | 395 | C | PHE | 57 | -24.351 | 23.597 | 55.503 | 1.00 | 12.68 |
| ATOM | 396 | O | PHE | 57 | -23.200 | 24.057 | 55.632 | 1.00 | 14.31 |
| ATOM | 397 | CB | PHE | 57 | -24.383 | 23.289 | 52.962 | 1.00 | 9.20 |
| ATOM | 398 | CG | PHE | 57 | -24.530 | 21.797 | 53.071 | 1.00 | 7.41 |
| ATOM | 399 | CD1 | PHE | 57 | -23.489 | 20.999 | 53.547 | 1.00 | 10.87 |
| ATOM | 400 | CD2 | PHE | 57 | -25.748 | 21.211 | 52.762 | 1.00 | 10.76 |
| ATOM | 401 | CE1 | PHE | 57 | -23.654 | 19.621 | 53.690 | 1.00 | 16.75 |
| ATOM | 402 | CE2 | PHE | 57 | -25.948 | 19.851 | 52.869 | 1.00 | 9.80 |
| ATOM | 403 | CZ | PHE | 57 | -24.897 | 19.033 | 53.326 | 1.00 | 17.07 |
| ATOM | 404 | N | PRO | 58 | -24.888 | 22.759 | 56.355 | 1.00 | 11.76 |
| ATOM | 405 | CA | PRO | 58 | -26.182 | 22.082 | 56.294 | 1.00 | 11.15 |
| ATOM | 406 | C | PRO | 58 | -27.302 | 22.967 | 56.755 | 1.00 | 9.63 |
| ATOM | 407 | O | PRO | 58 | -27.072 | 24.207 | 56.657 | 1.00 | 10.82 |
| ATOM | 408 | CB | PRO | 58 | -25.955 | 20.768 | 57.043 | 1.00 | 11.03 |
| ATOM | 409 | CG | PRO | 58 | -24.947 | 21.178 | 58.078 | 1.00 | 12.71 |
| ATOM | 410 | CD | PRO | 58 | -24.125 | 22.322 | 57.531 | 1.00 | 12.73 |
| ATOM | 411 | N | GLY | 59 | -28.466 | 22.432 | 57.103 | 1.00 | 10.97 |
| ATOM | 412 | CA | GLY | 59 | -29.594 | 23.338 | 57.495 | 1.00 | 11.26 |
| ATOM | 413 | C | GLY | 59 | -30.330 | 23.680 | 56.200 | 1.00 | 10.98 |
| ATOM | 414 | O | GLY | 59 | -31.477 | 23.240 | 56.091 | 1.00 | 11.30 |
| ATOM | 415 | N | ASN | 60 | -29.767 | 24.482 | 55.291 | 1.00 | 10.66 |
| ATOM | 416 | CA | ASN | 60 | -30.400 | 24.729 | 53.962 | 1.00 | 8.17 |
| ATOM | 417 | C | ASN | 60 | -29.377 | 24.099 | 52.981 | 1.00 | 9.56 |
| ATOM | 418 | O | ASN | 60 | -28.346 | 23.532 | 53.474 | 1.00 | 8.76 |
| ATOM | 419 | CB | ASN | 60 | -30.598 | 26.175 | 53.595 | 1.00 | 9.50 |
| ATOM | 420 | CG | ASN | 60 | -31.369 | 26.934 | 54.664 | 1.00 | 12.19 |
| ATOM | 421 | OD1 | ASN | 60 | -30.872 | 27.984 | 55.082 | 1.00 | 16.81 |
| ATOM | 422 | ND2 | ASN | 60 | -32.478 | 26.340 | 55.060 | 1.00 | 15.11 |
| ATOM | 423 | N | ASP | 61 | -29.582 | 24.193 | 51.661 | 1.00 | 7.15 |
| ATOM | 424 | CA | ASP | 61 | -28.544 | 23.661 | 50.701 | 1.00 | 7.83 |
| ATOM | 425 | C | ASP | 61 | -28.598 | 24.692 | 49.547 | 1.00 | 8.69 |
| ATOM | 426 | O | ASP | 61 | -29.213 | 24.393 | 48.519 | 1.00 | 7.71 |
| ATOM | 427 | CB | ASP | 61 | -28.818 | 22.216 | 50.313 | 1.00 | 4.48 |
| ATOM | 428 | CG | ASP | 61 | -27.637 | 21.575 | 49.640 | 1.00 | 6.18 |
| ATOM | 429 | OD1 | ASP | 61 | -27.591 | 20.419 | 49.245 | 1.00 | 6.86 |
| ATOM | 430 | OD2 | ASP | 61 | -26.622 | 22.316 | 49.431 | 1.00 | 8.20 |
| ATOM | 431 | N | ALA | 62 | -28.041 | 25.868 | 49.751 | 1.00 | 7.72 |
| ATOM | 432 | CB | ALA | 62 | -29.258 | 27.857 | 49.385 | 1.00 | 8.64 |
| ATOM | 433 | CA | ALA | 62 | -28.134 | 26.967 | 48.775 | 1.00 | 8.98 |
| ATOM | 434 | C | ALA | 62 | -26.880 | 27.802 | 48.618 | 1.00 | 9.19 |
| ATOM | 435 | O | ALA | 62 | -26.114 | 27.939 | 49.618 | 1.00 | 10.25 |
| ATOM | 436 | N | ALA | 63 | -26.667 | 28.360 | 47.434 | 1.00 | 7.69 |
| ATOM | 437 | CA | ALA | 63 | -25.476 | 29.189 | 47.173 | 1.00 | 7.50 |
| ATOM | 438 | C | ALA | 63 | -25.668 | 30.110 | 45.987 | 1.00 | 7.33 |
| ATOM | 439 | O | ALA | 63 | -26.526 | 29.843 | 45.116 | 1.00 | 6.36 |
| ATOM | 440 | CB | ALA | 63 | -24.247 | 28.263 | 46.886 | 1.00 | 4.57 |
| ATOM | 441 | N | PHE | 64 | -24.889 | 31.172 | 45.985 | 1.00 | 8.23 |

| | | | | | | | | |
|---|---|---|---|---|---|---|---|---|
| ATOM | 442 | CD2 | PHE | 64 | -24.221 | 35.364 | 43.942 | 1.00 6.73 |
| ATOM | 443 | CE2 | PHE | 64 | -24.051 | 36.237 | 42.841 | 1.00 7.23 |
| ATOM | 444 | CZ | PHE | 64 | -25.063 | 36.205 | 41.842 | 1.00 6.08 |
| ATOM | 445 | CE1 | PHE | 64 | -26.166 | 35.352 | 41.959 | 1.00 10.30 |
| ATOM | 446 | CD1 | PHE | 64 | -26.263 | 34.453 | 43.038 | 1.00 10.04 |
| ATOM | 447 | CG | PHE | 64 | -25.287 | 34.477 | 44.027 | 1.00 6.69 |
| ATOM | 448 | CB | PHE | 64 | -25.415 | 33.537 | 45.240 | 1.00 6.42 |
| ATOM | 449 | CA | PHE | 64 | -24.840 | 32.152 | 44.922 | 1.00 7.87 |
| ATOM | 450 | C | PHE | 64 | -23.351 | 32.196 | 44.518 | 1.00 10.06 |
| ATOM | 451 | O | PHE | 64 | -22.454 | 32.478 | 45.362 | 1.00 10.39 |
| ATOM | 452 | N | VAL | 65 | -23.080 | 31.952 | 43.234 | 1.00 8.61 |
| ATOM | 453 | CA | VAL | 65 | -21.722 | 32.028 | 42.662 | 1.00 8.62 |
| ATOM | 454 | C | VAL | 65 | -21.686 | 33.327 | 41.831 | 1.00 8.89 |
| ATOM | 455 | O | VAL | 65 | -22.514 | 33.548 | 40.948 | 1.00 7.44 |
| ATOM | 456 | CB | VAL | 65 | -21.338 | 30.840 | 41.722 | 1.00 11.34 |
| ATOM | 457 | CG1 | VAL | 65 | -20.018 | 31.055 | 40.967 | 1.00 10.37 |
| ATOM | 458 | CG2 | VAL | 65 | -21.333 | 29.530 | 42.493 | 1.00 9.94 |
| ATOM | 459 | N | ARG | 66 | -20.744 | 34.213 | 42.094 | 1.00 6.55 |
| ATOM | 460 | NH2 | ARG | 66 | -16.111 | 39.098 | 43.470 | 1.00 18.29 |
| ATOM | 461 | NH1 | ARG | 66 | -17.309 | 39.979 | 41.747 | 1.00 18.67 |
| ATOM | 462 | CZ | ARG | 66 | -17.271 | 39.260 | 42.832 | 1.00 18.74 |
| ATOM | 463 | NE | ARG | 66 | -18.308 | 38.673 | 43.409 | 1.00 22.97 |
| ATOM | 464 | CD | ARG | 66 | -19.672 | 38.751 | 42.950 | 1.00 23.13 |
| ATOM | 465 | CG | ARG | 66 | -19.916 | 37.827 | 41.797 | 1.00 18.33 |
| ATOM | 466 | CB | ARG | 66 | -19.949 | 36.464 | 42.422 | 1.00 12.11 |
| ATOM | 467 | CA | ARG | 66 | -20.545 | 35.475 | 41.416 | 1.00 8.00 |
| ATOM | 468 | C | ARG | 66 | -19.501 | 35.310 | 40.305 | 1.00 7.85 |
| ATOM | 469 | O | ARG | 66 | -18.447 | 34.738 | 40.557 | 1.00 8.51 |
| ATOM | 470 | N | GLY | 67 | -19.828 | 35.857 | 39.132 | 1.00 8.23 |
| ATOM | 471 | CA | GLY | 67 | -18.921 | 35.779 | 37.962 | 1.00 3.28 |
| ATOM | 472 | C | GLY | 67 | -17.838 | 36.834 | 38.114 | 1.00 7.11 |
| ATOM | 473 | O | GLY | 67 | -18.123 | 38.019 | 38.332 | 1.00 9.23 |
| ATOM | 474 | N | THR | 68 | -16.585 | 36.418 | 37.933 | 1.00 6.19 |
| ATOM | 475 | CA | THR | 68 | -15.407 | 37.292 | 37.994 | 1.00 6.13 |
| ATOM | 476 | C | THR | 68 | -14.784 | 37.468 | 36.611 | 1.00 10.55 |
| ATOM | 477 | O | THR | 68 | -13.939 | 38.358 | 36.375 | 1.00 9.20 |
| ATOM | 478 | CB | THR | 68 | -14.366 | 36.832 | 39.071 | 1.00 13.02 |
| ATOM | 479 | OG1 | THR | 68 | -13.865 | 35.569 | 38.579 | 1.00 9.29 |
| ATOM | 480 | CG2 | THR | 68 | -14.870 | 36.773 | 40.522 | 1.00 11.87 |
| ATOM | 481 | N | SER | 69 | -15.205 | 36.672 | 35.618 | 1.00 12.02 |
| ATOM | 482 | CA | SER | 69 | -14.736 | 36.796 | 34.233 | 1.00 11.62 |
| ATOM | 483 | C | SER | 69 | -15.660 | 36.069 | 33.264 | 1.00 12.37 |
| ATOM | 484 | O | SER | 69 | -15.911 | 34.865 | 33.480 | 1.00 11.23 |
| ATOM | 485 | CB | SER | 69 | -13.337 | 36.184 | 34.027 | 1.00 12.32 |
| ATOM | 486 | OG | SER | 69 | -12.823 | 36.389 | 32.763 | 1.00 15.07 |
| ATOM | 487 | N | ASN | 70 | -16.100 | 36.767 | 32.236 | 1.00 12.58 |
| ATOM | 488 | ND2 | ASN | 70 | -16.685 | 36.201 | 28.330 | 1.00 20.03 |
| ATOM | 489 | OD1 | ASN | 70 | -15.425 | 34.370 | 28.194 | 1.00 19.07 |
| ATOM | 490 | CG | ASN | 70 | -15.954 | 35.243 | 28.878 | 1.00 14.54 |
| ATOM | 491 | CB | ASN | 70 | -15.848 | 35.335 | 30.379 | 1.00 8.27 |
| ATOM | 492 | CA | ASN | 70 | -16.894 | 36.195 | 31.131 | 1.00 11.17 |
| ATOM | 493 | C | ASN | 70 | -18.166 | 35.424 | 31.400 | 1.00 10.53 |
| ATOM | 494 | O | ASN | 70 | -18.343 | 34.319 | 30.817 | 1.00 14.17 |
| ATOM | 495 | N | PHE | 71 | -19.048 | 35.946 | 32.209 | 1.00 8.98 |

| | | | | | | | | |
|---|---|---|---|---|---|---|---|---|
| ATOM | 496 | CD2 | PHE | 71 | -21.139 | 34.054 | 36.002 | 1.00 5.72 |
| ATOM | 497 | CE2 | PHE | 71 | -20.735 | 33.063 | 36.900 | 1.00 7.44 |
| ATOM | 498 | CZ | PHE | 71 | -19.483 | 32.395 | 36.669 | 1.00 10.35 |
| ATOM | 499 | CE1 | PHE | 71 | -18.713 | 32.681 | 35.550 | 1.00 10.41 |
| ATOM | 500 | CD1 | PHE | 71 | -19.159 | 33.681 | 34.652 | 1.00 9.67 |
| ATOM | 501 | CG | PHE | 71 | -20.350 | 34.372 | 34.873 | 1.00 5.76 |
| ATOM | 502 | CB | PHE | 71 | -20.839 | 35.417 | 33.897 | 1.00 7.11 |
| ATOM | 503 | CA | PHE | 71 | -20.346 | 35.257 | 32.435 | 1.00 10.26 |
| ATOM | 504 | C | PHE | 71 | -21.337 | 35.958 | 31.503 | 1.00 11.61 |
| ATOM | 505 | O | PHE | 71 | -21.429 | 37.207 | 31.537 | 1.00 14.68 |
| ATOM | 506 | N | THR | 72 | -22.071 | 35.275 | 30.691 | 1.00 11.03 |
| ATOM | 507 | CA | THR | 72 | -23.133 | 35.902 | 29.860 | 1.00 9.26 |
| ATOM | 508 | C | THR | 72 | -24.405 | 35.261 | 30.425 | 1.00 9.51 |
| ATOM | 509 | O | THR | 72 | -24.562 | 34.027 | 30.269 | 1.00 11.35 |
| ATOM | 510 | CB | THR | 72 | -23.036 | 35.596 | 28.328 | 1.00 15.61 |
| ATOM | 511 | OG1 | THR | 72 | -21.768 | 36.189 | 27.928 | 1.00 15.86 |
| ATOM | 512 | CG2 | THR | 72 | -24.177 | 36.178 | 27.494 | 1.00 14.54 |
| ATOM | 513 | N | LEU | 73 | -25.282 | 36.028 | 31.020 | 1.00 11.12 |
| ATOM | 514 | CA | LEU | 73 | -26.502 | 35.479 | 31.608 | 1.00 9.31 |
| ATOM | 515 | C | LEU | 73 | -27.504 | 35.184 | 30.484 | 1.00 9.04 |
| ATOM | 516 | O | LEU | 73 | -27.563 | 35.896 | 29.460 | 1.00 8.44 |
| ATOM | 517 | CB | LEU | 73 | -27.046 | 36.412 | 32.687 | 1.00 8.84 |
| ATOM | 518 | CG | LEU | 73 | -26.215 | 36.869 | 33.883 | 1.00 13.85 |
| ATOM | 519 | CD1 | LEU | 73 | -27.074 | 37.521 | 34.968 | 1.00 12.85 |
| ATOM | 520 | CD2 | LEU | 73 | -25.471 | 35.702 | 34.530 | 1.00 9.85 |
| ATOM | 521 | N | THR | 74 | -28.295 | 34.161 | 30.737 | 1.00 7.42 |
| ATOM | 522 | CG2 | THR | 74 | -27.696 | 32.554 | 28.200 | 1.00 3.40 |
| ATOM | 523 | OG1 | THR | 74 | -29.174 | 31.283 | 29.642 | 1.00 9.42 |
| ATOM | 524 | CB | THR | 74 | -29.063 | 32.532 | 28.922 | 1.00 7.73 |
| ATOM | 525 | CA | THR | 74 | -29.389 | 33.735 | 29.859 | 1.00 7.40 |
| ATOM | 526 | C | THR | 74 | -30.600 | 33.347 | 30.732 | 1.00 10.05 |
| ATOM | 527 | O | THR | 74 | -30.473 | 33.184 | 31.959 | 1.00 7.44 |
| ATOM | 528 | N | ASN | 75 | -31.775 | 33.201 | 30.069 | 1.00 8.53 |
| ATOM | 529 | ND2 | ASN | 75 | -36.021 | 33.747 | 28.974 | 1.00 14.07 |
| ATOM | 530 | OD1 | ASN | 75 | -33.929 | 33.279 | 28.252 | 1.00 14.16 |
| ATOM | 531 | CG | ASN | 75 | -34.723 | 33.526 | 29.157 | 1.00 15.69 |
| ATOM | 532 | CB | ASN | 75 | -34.178 | 33.518 | 30.570 | 1.00 11.17 |
| ATOM | 533 | CA | ASN | 75 | -32.924 | 32.729 | 30.849 | 1.00 9.39 |
| ATOM | 534 | C | ASN | 75 | -33.156 | 31.252 | 30.465 | 1.00 10.95 |
| ATOM | 535 | O | ASN | 75 | -34.322 | 30.835 | 30.620 | 1.00 13.03 |
| ATOM | 536 | N | LEU | 76 | -32.177 | 30.516 | 29.993 | 1.00 7.99 |
| ATOM | 537 | CD2 | LEU | 76 | -32.993 | 29.592 | 26.412 | 1.00 11.04 |
| ATOM | 538 | CD1 | LEU | 76 | -30.530 | 29.917 | 26.112 | 1.00 13.41 |
| ATOM | 539 | CG | LEU | 76 | -31.687 | 29.987 | 27.082 | 1.00 11.12 |
| ATOM | 540 | CB | LEU | 76 | -31.416 | 29.013 | 28.250 | 1.00 10.63 |
| ATOM | 541 | CA | LEU | 76 | -32.315 | 29.158 | 29.530 | 1.00 8.79 |
| ATOM | 542 | C | LEU | 76 | -31.876 | 28.059 | 30.512 | 1.00 8.97 |
| ATOM | 543 | O | LEU | 76 | -31.038 | 28.290 | 31.385 | 1.00 6.01 |
| ATOM | 544 | N | VAL | 77 | -32.529 | 26.936 | 30.323 | 1.00 8.54 |
| ATOM | 545 | CA | VAL | 77 | -32.285 | 25.689 | 31.062 | 1.00 8.05 |
| ATOM | 546 | C | VAL | 77 | -32.125 | 24.578 | 29.973 | 1.00 9.00 |
| ATOM | 547 | O | VAL | 77 | -33.126 | 24.380 | 29.178 | 1.00 6.78 |
| ATOM | 548 | CB | VAL | 77 | -33.397 | 25.290 | 32.052 | 1.00 8.09 |
| ATOM | 549 | CG1 | VAL | 77 | -33.049 | 23.911 | 32.715 | 1.00 5.84 |

| | | | | | | | | |
|---|---|---|---|---|---|---|---|---|
| ATOM | 550 | CG2 | VAL | 77 | -33.575 | 26.350 | 33.142 | 1.00 10.07 |
| ATOM | 551 | N | SER | 78 | -31.017 | 23.871 | 29.974 | 1.00  8.67 |
| ATOM | 552 | OG | SER | 78 | -29.161 | 21.344 | 27.899 | 1.00  9.85 |
| ATOM | 553 | CB | SER | 78 | -29.355 | 22.409 | 28.857 | 1.00 12.29 |
| ATOM | 554 | CA | SER | 78 | -30.831 | 22.814 | 28.929 | 1.00  8.23 |
| ATOM | 555 | C | SER | 78 | -31.710 | 21.583 | 29.189 | 1.00  9.82 |
| ATOM | 556 | O | SER | 78 | -31.759 | 21.055 | 30.305 | 1.00  7.69 |
| ATOM | 557 | N | ARG | 79 | -32.337 | 21.082 | 28.116 | 1.00  9.80 |
| ATOM | 558 | NH2 | ARG | 79 | -37.443 | 22.028 | 24.212 | 1.00 31.34 |
| ATOM | 559 | NH1 | ARG | 79 | -38.500 | 22.780 | 26.184 | 1.00 27.56 |
| ATOM | 560 | CZ | ARG | 79 | -37.601 | 21.991 | 25.554 | 1.00 28.07 |
| ATOM | 561 | NE | ARG | 79 | -36.785 | 21.131 | 26.161 | 1.00 21.89 |
| ATOM | 562 | CD | ARG | 79 | -36.718 | 20.936 | 27.589 | 1.00 18.78 |
| ATOM | 563 | CG | ARG | 79 | -35.265 | 21.118 | 27.992 | 1.00  9.14 |
| ATOM | 564 | CB | ARG | 79 | -34.499 | 19.957 | 27.396 | 1.00  7.07 |
| ATOM | 565 | CA | ARG | 79 | -33.163 | 19.879 | 28.166 | 1.00 10.01 |
| ATOM | 566 | C | ARG | 79 | -32.272 | 18.740 | 27.659 | 1.00 11.09 |
| ATOM | 567 | O | ARG | 79 | -32.799 | 17.622 | 27.476 | 1.00 11.76 |
| ATOM | 568 | N | TYR | 80 | -30.980 | 18.901 | 27.456 | 1.00 10.89 |
| ATOM | 569 | OH | TYR | 80 | -25.669 | 19.608 | 31.411 | 1.00 13.70 |
| ATOM | 570 | CD2 | TYR | 80 | -28.969 | 18.626 | 30.175 | 1.00  8.55 |
| ATOM | 571 | CE2 | TYR | 80 | -28.018 | 19.277 | 30.962 | 1.00  9.07 |
| ATOM | 572 | CZ | TYR | 80 | -26.667 | 19.006 | 30.683 | 1.00 13.15 |
| ATOM | 573 | CE1 | TYR | 80 | -26.290 | 18.103 | 29.673 | 1.00 13.12 |
| ATOM | 574 | CD1 | TYR | 80 | -27.305 | 17.481 | 28.921 | 1.00 12.00 |
| ATOM | 575 | CG | TYR | 80 | -28.646 | 17.742 | 29.153 | 1.00 10.87 |
| ATOM | 576 | CB | TYR | 80 | -29.686 | 17.010 | 28.331 | 1.00 11.71 |
| ATOM | 577 | CA | TYR | 80 | -30.100 | 17.809 | 27.036 | 1.00 13.19 |
| ATOM | 578 | C | TYR | 80 | -30.669 | 16.889 | 25.939 | 1.00 15.57 |
| ATOM | 579 | O | TYR | 80 | -31.074 | 17.414 | 24.848 | 1.00 16.53 |
| ATOM | 580 | N | ASN | 81 | -30.732 | 15.583 | 26.157 | 1.00 15.67 |
| ATOM | 581 | ND2 | ASN | 81 | -30.251 | 12.075 | 23.672 | 0.50 23.42 |
| ATOM | 582 | OD1 | ASN | 81 | -31.653 | 10.851 | 24.930 | 0.50 22.68 |
| ATOM | 583 | CG | ASN | 81 | -31.012 | 11.924 | 24.769 | 0.50 24.69 |
| ATOM | 584 | CB | ASN | 81 | -30.915 | 13.117 | 25.699 | 0.50 20.33 |
| ATOM | 589 | CA | ASN | 81 | -31.169 | 14.536 | 25.163 | 1.00 17.67 |
| ATOM | 590 | C | ASN | 81 | -32.611 | 14.689 | 24.807 | 1.00 18.70 |
| ATOM | 591 | O | ASN | 81 | -33.067 | 14.207 | 23.731 | 1.00 20.41 |
| ATOM | 592 | N | THR | 82 | -33.405 | 15.385 | 25.621 | 1.00 15.25 |
| ATOM | 593 | CG2 | THR | 82 | -36.933 | 16.845 | 26.136 | 1.00 15.50 |
| ATOM | 594 | OG1 | THR | 82 | -35.944 | 14.838 | 27.235 | 1.00 15.80 |
| ATOM | 595 | CB | THR | 82 | -35.663 | 16.070 | 26.495 | 1.00 13.76 |
| ATOM | 596 | CA | THR | 82 | -34.787 | 15.661 | 25.275 | 1.00 16.61 |
| ATOM | 597 | C | THR | 82 | -34.775 | 16.712 | 24.128 | 1.00 19.57 |
| ATOM | 598 | O | THR | 82 | -35.725 | 16.765 | 23.314 | 1.00 20.18 |
| ATOM | 599 | N | GLY | 83 | -33.765 | 17.555 | 23.973 | 1.00 17.44 |
| ATOM | 600 | CA | GLY | 83 | -33.611 | 18.551 | 22.941 | 1.00 16.21 |
| ATOM | 601 | C | GLY | 83 | -34.082 | 19.964 | 23.286 | 1.00 12.64 |
| ATOM | 602 | O | GLY | 83 | -35.127 | 20.225 | 23.908 | 1.00 12.83 |
| ATOM | 603 | N | GLY | 84 | -33.281 | 20.926 | 22.859 | 1.00 11.84 |
| ATOM | 604 | CA | GLY | 84 | -33.604 | 22.331 | 23.082 | 1.00 11.09 |
| ATOM | 605 | C | GLY | 84 | -33.492 | 22.741 | 24.541 | 1.00  9.78 |
| ATOM | 606 | O | GLY | 84 | -32.796 | 22.177 | 25.384 | 1.00 10.83 |
| ATOM | 607 | N | TYR | 85 | -34.104 | 23.875 | 24.825 | 1.00 10.88 |

| | | | | | | | | |
|---|---|---|---|---|---|---|---|---|
| ATOM | 608 | OH | TYR | 85 | -28.004 | 24.555 | 24.203 | 1.00 18.98 |
| ATOM | 609 | CD2 | TYR | 85 | -31.561 | 25.395 | 24.068 | 1.00 12.07 |
| ATOM | 610 | CE2 | TYR | 85 | -30.266 | 25.023 | 23.693 | 1.00 13.73 |
| ATOM | 611 | CZ | TYR | 85 | -29.263 | 24.890 | 24.644 | 1.00 15.05 |
| ATOM | 612 | CE1 | TYR | 85 | -29.519 | 25.081 | 26.012 | 1.00 12.94 |
| ATOM | 613 | CD1 | TYR | 85 | -30.826 | 25.421 | 26.395 | 1.00 12.96 |
| ATOM | 614 | CG | TYR | 85 | -31.850 | 25.570 | 25.445 | 1.00 11.64 |
| ATOM | 615 | CB | TYR | 85 | -33.264 | 25.866 | 25.882 | 1.00 10.50 |
| ATOM | 616 | CA | TYR | 85 | -34.079 | 24.539 | 26.116 | 1.00 10.86 |
| ATOM | 617 | C | TYR | 85 | -35.418 | 25.002 | 26.674 | 1.00 13.82 |
| ATOM | 618 | O | TYR | 85 | -36.268 | 25.491 | 25.854 | 1.00 14.41 |
| ATOM | 619 | N | ALA | 86 | -35.569 | 24.891 | 27.969 | 1.00 9.86 |
| ATOM | 620 | CB | ALA | 86 | -37.046 | 24.630 | 29.971 | 1.00 9.75 |
| ATOM | 621 | CA | ALA | 86 | -36.735 | 25.425 | 28.695 | 1.00 11.67 |
| ATOM | 622 | C | ALA | 86 | -36.361 | 26.918 | 28.958 | 1.00 11.87 |
| ATOM | 623 | O | ALA | 86 | -35.188 | 27.341 | 28.972 | 1.00 9.92 |
| ATOM | 624 | N | THR | 87 | -37.345 | 27.829 | 29.131 | 1.00 10.43 |
| ATOM | 625 | CG2 | THR | 87 | -36.841 | 29.875 | 26.861 | 1.00 17.11 |
| ATOM | 626 | OG1 | THR | 87 | -38.959 | 29.934 | 28.083 | 1.00 17.19 |
| ATOM | 627 | CB | THR | 87 | -37.539 | 30.174 | 28.200 | 1.00 17.24 |
| ATOM | 628 | CA | THR | 87 | -37.057 | 29.241 | 29.379 | 1.00 10.64 |
| ATOM | 629 | C | THR | 87 | -37.640 | 29.593 | 30.724 | 1.00 11.34 |
| ATOM | 630 | O | THR | 87 | -38.696 | 29.055 | 31.041 | 1.00 13.09 |
| ATOM | 631 | N | VAL | 88 | -37.001 | 30.448 | 31.521 | 1.00 10.66 |
| ATOM | 632 | CA | VAL | 88 | -37.441 | 30.863 | 32.856 | 1.00 9.45 |
| ATOM | 633 | C | VAL | 88 | -38.255 | 32.155 | 32.696 | 1.00 11.88 |
| ATOM | 634 | O | VAL | 88 | -37.698 | 33.094 | 32.136 | 1.00 10.63 |
| ATOM | 635 | CB | VAL | 88 | -36.246 | 31.053 | 33.821 | 1.00 7.00 |
| ATOM | 636 | CG1 | VAL | 88 | -36.652 | 31.636 | 35.192 | 1.00 5.32 |
| ATOM | 637 | CG2 | VAL | 88 | -35.478 | 29.746 | 33.985 | 1.00 9.05 |
| ATOM | 638 | N | ALA | 89 | -39.467 | 32.233 | 33.201 | 1.00 10.89 |
| ATOM | 639 | CB | ALA | 89 | -41.539 | 33.201 | 32.260 | 1.00 9.11 |
| ATOM | 640 | CA | ALA | 89 | -40.325 | 33.440 | 33.132 | 1.00 11.01 |
| ATOM | 641 | C | ALA | 89 | -40.690 | 33.918 | 34.548 | 1.00 11.13 |
| ATOM | 642 | O | ALA | 89 | -41.242 | 35.028 | 34.655 | 1.00 13.90 |
| ATOM | 643 | N | GLY | 90 | -40.351 | 33.181 | 35.617 | 1.00 9.54 |
| ATOM | 644 | CA | GLY | 90 | -40.632 | 33.592 | 36.976 | 1.00 8.75 |
| ATOM | 645 | C | GLY | 90 | -40.322 | 32.409 | 37.921 | 1.00 10.19 |
| ATOM | 646 | O | GLY | 90 | -39.660 | 31.477 | 37.500 | 1.00 9.62 |
| ATOM | 647 | N | HIS | 91 | -40.857 | 32.540 | 39.135 | 1.00 11.81 |
| ATOM | 648 | CD2 | HIS | 91 | -40.073 | 33.404 | 43.018 | 1.00 18.32 |
| ATOM | 649 | NE2 | HIS | 91 | -40.052 | 34.763 | 43.177 | 1.00 17.97 |
| ATOM | 650 | CE1 | HIS | 91 | -39.622 | 35.366 | 42.127 | 1.00 17.17 |
| ATOM | 651 | ND1 | HIS | 91 | -39.350 | 34.411 | 41.259 | 1.00 16.07 |
| ATOM | 652 | CG | HIS | 91 | -39.605 | 33.184 | 41.765 | 1.00 16.04 |
| ATOM | 653 | CB | HIS | 91 | -39.411 | 31.883 | 41.060 | 1.00 11.82 |
| ATOM | 654 | CA | HIS | 91 | -40.637 | 31.530 | 40.180 | 1.00 10.58 |
| ATOM | 655 | C | HIS | 91 | -41.854 | 31.229 | 41.025 | 1.00 12.38 |
| ATOM | 656 | O | HIS | 91 | -41.723 | 31.032 | 42.248 | 1.00 13.11 |
| ATOM | 657 | N | ASN | 92 | -43.013 | 31.126 | 40.369 | 1.00 12.16 |
| ATOM | 658 | ND2 | ASN | 92 | -46.608 | 32.760 | 41.360 | 1.00 44.37 |
| ATOM | 659 | OD1 | ASN | 92 | -45.564 | 33.225 | 39.385 | 1.00 40.52 |
| ATOM | 660 | CG | ASN | 92 | -45.903 | 32.418 | 40.259 | 1.00 35.33 |
| ATOM | 661 | CB | ASN | 92 | -45.524 | 30.938 | 40.252 | 1.00 23.82 |

| | | | | | | | | |
|---|---|---|---|---|---|---|---|---|
| ATOM | 662 | CA | ASN | 92 | -44.261 | 30.746 | 41.119 | 1.00 13.35 |
| ATOM | 663 | C | ASN | 92 | -44.164 | 29.268 | 41.493 | 1.00 12.66 |
| ATOM | 664 | O | ASN | 92 | -43.930 | 28.437 | 40.582 | 1.00 11.76 |
| ATOM | 665 | N | GLN | 93 | -44.364 | 28.935 | 42.749 | 1.00 11.08 |
| ATOM | 666 | NE2 | GLN | 93 | -42.340 | 27.432 | 47.693 | 1.00 21.50 |
| ATOM | 667 | OE1 | GLN | 93 | -44.559 | 27.501 | 47.458 | 1.00 31.26 |
| ATOM | 668 | CD | GLN | 93 | -43.422 | 27.632 | 46.972 | 1.00 27.63 |
| ATOM | 669 | CG | GLN | 93 | -43.291 | 28.002 | 45.511 | 1.00 20.72 |
| ATOM | 670 | CB | GLN | 93 | -44.409 | 27.379 | 44.700 | 1.00 15.24 |
| ATOM | 671 | CA | GLN | 93 | -44.262 | 27.516 | 43.171 | 1.00 12.74 |
| ATOM | 672 | C | GLN | 93 | -45.394 | 26.705 | 42.566 | 1.00 13.82 |
| ATOM | 673 | O | GLN | 93 | -46.572 | 27.162 | 42.672 | 1.00 15.94 |
| ATOM | 674 | N | ALA | 94 | -45.166 | 25.549 | 42.048 | 1.00 11.74 |
| ATOM | 675 | CA | ALA | 94 | -46.178 | 24.676 | 41.481 | 1.00 11.41 |
| ATOM | 676 | C | ALA | 94 | -46.815 | 23.934 | 42.649 | 1.00 14.20 |
| ATOM | 677 | O | ALA | 94 | -46.120 | 23.587 | 43.637 | 1.00 14.08 |
| ATOM | 678 | CB | ALA | 94 | -45.495 | 23.704 | 40.529 | 1.00 6.58 |
| ATOM | 679 | N | PRO | 95 | -48.112 | 23.645 | 42.551 | 1.00 14.96 |
| ATOM | 680 | CG | PRO | 95 | -50.259 | 23.275 | 41.661 | 1.00 15.96 |
| ATOM | 681 | CD | PRO | 95 | -48.954 | 24.020 | 41.412 | 1.00 15.38 |
| ATOM | 682 | CB | PRO | 95 | -50.261 | 22.810 | 43.087 | 1.00 13.99 |
| ATOM | 683 | CA | PRO | 95 | -48.815 | 22.843 | 43.571 | 1.00 13.77 |
| ATOM | 684 | C | PRO | 95 | -48.308 | 21.414 | 43.670 | 1.00 12.85 |
| ATOM | 685 | O | PRO | 95 | -47.789 | 20.722 | 42.764 | 1.00 13.21 |
| ATOM | 686 | N | ILE | 96 | -48.439 | 20.860 | 44.892 | 1.00 9.64 |
| ATOM | 687 | CD1 | ILE | 96 | -46.305 | 19.698 | 47.937 | 1.00 20.39 |
| ATOM | 688 | CG1 | ILE | 96 | -47.785 | 19.940 | 47.690 | 1.00 17.20 |
| ATOM | 689 | CB | ILE | 96 | -48.425 | 19.023 | 46.634 | 1.00 13.72 |
| ATOM | 690 | CG2 | ILE | 96 | -48.131 | 17.530 | 46.952 | 1.00 17.91 |
| ATOM | 691 | CA | ILE | 96 | -48.058 | 19.444 | 45.141 | 1.00 11.51 |
| ATOM | 692 | C | ILE | 96 | -48.841 | 18.627 | 44.138 | 1.00 13.14 |
| ATOM | 693 | O | ILE | 96 | -50.052 | 18.979 | 43.880 | 1.00 15.21 |
| ATOM | 694 | N | GLY | 97 | -48.332 | 17.575 | 43.528 | 1.00 10.18 |
| ATOM | 695 | CA | GLY | 97 | -49.020 | 16.783 | 42.537 | 1.00 9.00 |
| ATOM | 696 | C | GLY | 97 | -48.645 | 17.200 | 41.126 | 1.00 11.33 |
| ATOM | 697 | O | GLY | 97 | -48.867 | 16.374 | 40.221 | 1.00 12.32 |
| ATOM | 698 | N | SER | 98 | -48.108 | 18.393 | 40.935 | 1.00 10.97 |
| ATOM | 699 | OG | SER | 98 | -48.122 | 21.262 | 40.073 | 0.70 15.96 |
| ATOM | 700 | CB | SER | 98 | -47.149 | 20.355 | 39.724 | 0.70 13.01 |
| ATOM | 703 | CA | SER | 98 | -47.643 | 18.918 | 39.637 | 1.00 11.70 |
| ATOM | 704 | C | SER | 98 | -46.376 | 18.198 | 39.140 | 1.00 11.01 |
| ATOM | 705 | O | SER | 98 | -45.567 | 17.708 | 39.906 | 1.00 12.53 |
| ATOM | 706 | N | SER | 99 | -46.203 | 18.149 | 37.825 | 1.00 8.54 |
| ATOM | 707 | OG | SER | 99 | -45.372 | 18.423 | 34.957 | 1.00 12.93 |
| ATOM | 708 | CB | SER | 99 | -45.157 | 17.258 | 35.747 | 1.00 7.78 |
| ATOM | 709 | CA | SER | 99 | -45.010 | 17.562 | 37.226 | 1.00 8.54 |
| ATOM | 710 | C | SER | 99 | -43.921 | 18.659 | 37.391 | 1.00 7.90 |
| ATOM | 711 | O | SER | 99 | -44.195 | 19.884 | 37.534 | 1.00 10.31 |
| ATOM | 712 | N | VAL | 100 | -42.675 | 18.231 | 37.384 | 1.00 9.21 |
| ATOM | 713 | CA | VAL | 100 | -41.468 | 19.082 | 37.505 | 1.00 5.59 |
| ATOM | 714 | C | VAL | 100 | -40.375 | 18.343 | 36.773 | 1.00 5.35 |
| ATOM | 715 | O | VAL | 100 | -40.380 | 17.108 | 36.785 | 1.00 9.03 |
| ATOM | 716 | CB | VAL | 100 | -41.112 | 19.395 | 38.979 | 1.00 5.88 |
| ATOM | 717 | CG1 | VAL | 100 | -40.630 | 18.114 | 39.670 | 1.00 8.61 |

| ATOM | 718 | CG2 | VAL | 100 | -40.142 | 20.579 | 39.127 | 1.00 | 5.24 |
|------|-----|-----|-----|-----|---------|--------|--------|------|------|
| ATOM | 719 | N | CYS | 101 | -39.423 | 19.055 | 36.168 | 1.00 | 5.24 |
| ATOM | 720 | CA | CYS | 101 | -38.304 | 18.494 | 35.437 | 1.00 | 4.35 |
| ATOM | 721 | C | CYS | 101 | -36.989 | 18.996 | 36.086 | 1.00 | 5.37 |
| ATOM | 722 | O | CYS | 101 | -36.984 | 20.152 | 36.529 | 1.00 | 8.17 |
| ATOM | 723 | CB | CYS | 101 | -38.312 | 18.824 | 33.935 | 1.00 | 5.99 |
| ATOM | 724 | SG | CYS | 101 | -39.723 | 18.001 | 33.063 | 1.00 | 8.35 |
| ATOM | 725 | N | ARG | 102 | -35.982 | 18.175 | 36.084 | 1.00 | 6.08 |
| ATOM | 726 | CA | ARG | 102 | -34.649 | 18.527 | 36.587 | 1.00 | 7.57 |
| ATOM | 727 | C | ARG | 102 | -33.605 | 18.534 | 35.462 | 1.00 | 8.71 |
| ATOM | 728 | O | ARG | 102 | -33.604 | 17.647 | 34.598 | 1.00 | 8.00 |
| ATOM | 729 | CB | ARG | 102 | -34.261 | 17.489 | 37.655 | 1.00 | 4.69 |
| ATOM | 730 | CG | ARG | 102 | -32.859 | 17.784 | 38.286 | 1.00 | 3.27 |
| ATOM | 731 | CD | ARG | 102 | -32.303 | 16.653 | 39.077 | 1.00 | 6.25 |
| ATOM | 732 | NE | ARG | 102 | -32.250 | 15.402 | 38.343 | 1.00 | 7.04 |
| ATOM | 733 | CZ | ARG | 102 | -31.471 | 15.083 | 37.294 | 1.00 | 9.62 |
| ATOM | 734 | NH1 | ARG | 102 | -31.692 | 13.864 | 36.773 | 1.00 | 9.55 |
| ATOM | 735 | NH2 | ARG | 102 | -30.608 | 15.953 | 36.805 | 1.00 | 5.91 |
| ATOM | 736 | N | SER | 103 | -32.662 | 19.454 | 35.404 | 1.00 | 7.27 |
| ATOM | 737 | CA | SER | 103 | -31.567 | 19.475 | 34.435 | 1.00 | 4.96 |
| ATOM | 738 | C | SER | 103 | -30.259 | 19.365 | 35.228 | 1.00 | 6.42 |
| ATOM | 739 | O | SER | 103 | -30.059 | 20.177 | 36.162 | 1.00 | 6.49 |
| ATOM | 740 | CB | SER | 103 | -31.571 | 20.781 | 33.624 | 1.00 | 5.59 |
| ATOM | 741 | OG | SER | 103 | -30.581 | 20.673 | 32.575 | 1.00 | 7.71 |
| ATOM | 742 | N | GLY | 104 | -29.359 | 18.411 | 34.965 | 1.00 | 7.52 |
| ATOM | 743 | CA | GLY | 104 | -28.071 | 18.282 | 35.661 | 1.00 | 5.92 |
| ATOM | 744 | C | GLY | 104 | -27.031 | 17.745 | 34.686 | 1.00 | 6.41 |
| ATOM | 745 | O | GLY | 104 | -27.354 | 17.083 | 33.665 | 1.00 | 7.09 |
| ATOM | 746 | N | SER | 105 | -25.757 | 18.002 | 34.912 | 1.00 | 7.88 |
| ATOM | 747 | OG | SER | 105 | -22.953 | 18.433 | 35.504 | 1.00 | 11.75 |
| ATOM | 748 | CB | SER | 105 | -23.430 | 18.504 | 34.179 | 1.00 | 7.00 |
| ATOM | 749 | CA | SER | 105 | -24.638 | 17.559 | 34.049 | 1.00 | 10.37 |
| ATOM | 750 | C | SER | 105 | -24.255 | 16.085 | 34.102 | 1.00 | 10.06 |
| ATOM | 751 | O | SER | 105 | -23.505 | 15.679 | 33.176 | 1.00 | 10.75 |
| ATOM | 752 | N | THR | 106 | -24.719 | 15.248 | 35.018 | 1.00 | 9.74 |
| ATOM | 753 | CA | THR | 106 | -24.403 | 13.811 | 35.029 | 1.00 | 9.92 |
| ATOM | 754 | C | THR | 106 | -25.458 | 13.046 | 34.238 | 1.00 | 8.56 |
| ATOM | 755 | O | THR | 106 | -25.079 | 12.174 | 33.464 | 1.00 | 10.42 |
| ATOM | 756 | CB | THR | 106 | -24.322 | 13.103 | 36.435 | 1.00 | 10.71 |
| ATOM | 757 | OG1 | THR | 106 | -23.436 | 13.978 | 37.167 | 1.00 | 10.45 |
| ATOM | 758 | CG2 | THR | 106 | -23.782 | 11.671 | 36.508 | 1.00 | 6.76 |
| ATOM | 759 | N | THR | 107 | -26.723 | 13.319 | 34.467 | 1.00 | 7.87 |
| ATOM | 760 | CA | THR | 107 | -27.804 | 12.599 | 33.831 | 1.00 | 5.96 |
| ATOM | 761 | C | THR | 107 | -28.634 | 13.349 | 32.838 | 1.00 | 7.88 |
| ATOM | 762 | O | THR | 107 | -29.531 | 12.664 | 32.266 | 1.00 | 8.47 |
| ATOM | 763 | CB | THR | 107 | -28.695 | 11.935 | 34.969 | 1.00 | 8.85 |
| ATOM | 764 | OG1 | THR | 107 | -29.241 | 13.086 | 35.695 | 1.00 | 7.24 |
| ATOM | 765 | CG2 | THR | 107 | -27.869 | 11.012 | 35.858 | 1.00 | 8.14 |
| ATOM | 766 | N | GLY | 108 | -28.523 | 14.609 | 32.643 | 1.00 | 7.16 |
| ATOM | 767 | CA | GLY | 108 | -29.341 | 15.323 | 31.611 | 1.00 | 8.94 |
| ATOM | 768 | C | GLY | 108 | -30.668 | 15.756 | 32.223 | 1.00 | 10.50 |
| ATOM | 769 | O | GLY | 108 | -30.722 | 16.175 | 33.436 | 1.00 | 8.98 |
| ATOM | 770 | N | TRP | 109 | -31.691 | 15.642 | 31.408 | 1.00 | 6.52 |
| ATOM | 771 | CD2 | TRP | 109 | -35.413 | 18.684 | 30.968 | 1.00 | 5.39 |

| | | | | | | | | | |
|---|---|---|---|---|---|---|---|---|---|
| ATOM | 772 | CE3 | TRP | 109 | -34.790 | 19.728 | 31.656 | 1.00 | 5.67 |
| ATOM | 773 | CZ3 | TRP | 109 | -35.588 | 20.864 | 31.900 | 1.00 | 10.11 |
| ATOM | 774 | CH2 | TRP | 109 | -36.931 | 20.950 | 31.533 | 1.00 | 7.46 |
| ATOM | 775 | CZ2 | TRP | 109 | -37.555 | 19.912 | 30.864 | 1.00 | 5.36 |
| ATOM | 776 | CE2 | TRP | 109 | -36.762 | 18.789 | 30.603 | 1.00 | 8.40 |
| ATOM | 777 | NE1 | TRP | 109 | -37.097 | 17.619 | 29.964 | 1.00 | 11.33 |
| ATOM | 778 | CD1 | TRP | 109 | -35.996 | 16.771 | 29.909 | 1.00 | 8.89 |
| ATOM | 779 | CG | TRP | 109 | -34.928 | 17.409 | 30.506 | 1.00 | 7.87 |
| ATOM | 780 | CB | TRP | 109 | -33.558 | 16.856 | 30.594 | 1.00 | 4.08 |
| ATOM | 781 | CA | TRP | 109 | -33.070 | 16.106 | 31.803 | 1.00 | 6.13 |
| ATOM | 782 | C | TRP | 109 | -34.031 | 15.013 | 32.176 | 1.00 | 7.55 |
| ATOM | 783 | O | TRP | 109 | -34.244 | 14.017 | 31.372 | 1.00 | 8.28 |
| ATOM | 784 | N | HIS | 110 | -34.566 | 15.040 | 33.380 | 1.00 | 6.29 |
| ATOM | 785 | CD2 | HIS | 110 | -32.409 | 12.573 | 33.819 | 1.00 | 8.99 |
| ATOM | 786 | NE2 | HIS | 110 | -31.845 | 11.558 | 33.121 | 1.00 | 10.03 |
| ATOM | 787 | CE1 | HIS | 110 | -32.751 | 10.595 | 32.981 | 1.00 | 12.94 |
| ATOM | 788 | ND1 | HIS | 110 | -33.856 | 11.027 | 33.562 | 1.00 | 12.68 |
| ATOM | 789 | CG | HIS | 110 | -33.678 | 12.246 | 34.128 | 1.00 | 9.92 |
| ATOM | 790 | CB | HIS | 110 | -34.761 | 13.004 | 34.840 | 1.00 | 8.94 |
| ATOM | 791 | CA | HIS | 110 | -35.487 | 13.971 | 33.861 | 1.00 | 7.82 |
| ATOM | 792 | C | HIS | 110 | -36.648 | 14.637 | 34.584 | 1.00 | 7.74 |
| ATOM | 793 | O | HIS | 110 | -36.444 | 15.708 | 35.190 | 1.00 | 8.03 |
| ATOM | 794 | N | CYS | 111 | -37.832 | 13.990 | 34.506 | 1.00 | 7.77 |
| ATOM | 795 | CA | CYS | 111 | -39.052 | 14.589 | 35.065 | 1.00 | 7.64 |
| ATOM | 796 | C | CYS | 111 | -39.864 | 13.660 | 35.952 | 1.00 | 9.31 |
| ATOM | 797 | O | CYS | 111 | -39.559 | 12.451 | 35.928 | 1.00 | 11.03 |
| ATOM | 798 | CB | CYS | 111 | -39.988 | 15.100 | 33.925 | 1.00 | 9.61 |
| ATOM | 799 | SG | CYS | 111 | -39.150 | 16.153 | 32.711 | 1.00 | 9.12 |
| ATOM | 800 | N | GLY | 112 | -40.828 | 14.245 | 36.638 | 1.00 | 8.81 |
| ATOM | 801 | CA | GLY | 112 | -41.625 | 13.408 | 37.597 | 1.00 | 8.51 |
| ATOM | 802 | C | GLY | 112 | -42.521 | 14.315 | 38.399 | 1.00 | 10.25 |
| ATOM | 803 | O | GLY | 112 | -42.794 | 15.437 | 37.941 | 1.00 | 12.04 |
| ATOM | 804 | N | THR | 113 | -42.979 | 13.969 | 39.595 | 1.00 | 10.08 |
| ATOM | 805 | CA | THR | 113 | -43.870 | 14.809 | 40.372 | 1.00 | 8.62 |
| ATOM | 806 | C | THR | 113 | -43.359 | 15.387 | 41.685 | 1.00 | 9.71 |
| ATOM | 807 | O | THR | 113 | -42.441 | 14.786 | 42.268 | 1.00 | 10.48 |
| ATOM | 808 | CB | THR | 113 | -45.240 | 13.996 | 40.648 | 1.00 | 17.08 |
| ATOM | 809 | OG1 | THR | 113 | -44.930 | 12.755 | 41.340 | 1.00 | 19.10 |
| ATOM | 810 | CG2 | THR | 113 | -46.004 | 13.705 | 39.362 | 1.00 | 15.24 |
| ATOM | 811 | N | ILE | 114 | -43.963 | 16.488 | 42.073 | 1.00 | 8.35 |
| ATOM | 812 | CA | ILE | 114 | -43.662 | 17.108 | 43.365 | 1.00 | 9.73 |
| ATOM | 813 | C | ILE | 114 | -44.554 | 16.338 | 44.383 | 1.00 | 13.59 |
| ATOM | 814 | O | ILE | 114 | -45.816 | 16.336 | 44.198 | 1.00 | 12.54 |
| ATOM | 815 | CB | ILE | 114 | -44.008 | 18.621 | 43.384 | 1.00 | 10.58 |
| ATOM | 816 | CG1 | ILE | 114 | -43.089 | 19.319 | 42.341 | 1.00 | 12.00 |
| ATOM | 817 | CG2 | ILE | 114 | -43.864 | 19.215 | 44.814 | 1.00 | 12.84 |
| ATOM | 818 | CD1 | ILE | 114 | -43.555 | 20.750 | 42.065 | 1.00 | 10.62 |
| ATOM | 819 | N | GLN | 115 | -43.977 | 15.668 | 45.379 | 1.00 | 12.39 |
| ATOM | 820 | NE2 | GLN | 115 | -43.951 | 10.378 | 45.759 | 1.00 | 33.00 |
| ATOM | 821 | OE1 | GLN | 115 | -42.098 | 11.415 | 46.407 | 1.00 | 34.76 |
| ATOM | 822 | CD | GLN | 115 | -43.243 | 11.496 | 45.943 | 1.00 | 30.30 |
| ATOM | 823 | CG | GLN | 115 | -43.993 | 12.758 | 45.524 | 1.00 | 18.83 |
| ATOM | 824 | CB | GLN | 115 | -44.077 | 13.606 | 46.811 | 1.00 | 11.43 |
| ATOM | 825 | CA | GLN | 115 | -44.732 | 14.936 | 46.396 | 1.00 | 11.59 |

| | | | | | | | | | |
|---|---|---|---|---|---|---|---|---|---|
| ATOM | 826 | C | GLN | 115 | -44.956 | 15.640 | 47.693 | 1.00 | 11.61 |
| ATOM | 827 | O | GLN | 115 | -46.105 | 15.494 | 48.196 | 1.00 | 14.96 |
| ATOM | 828 | N | ALA | 116 | -44.037 | 16.355 | 48.292 | 1.00 | 12.17 |
| ATOM | 829 | CA | ALA | 116 | -44.291 | 16.976 | 49.618 | 1.00 | 10.65 |
| ATOM | 830 | C | ALA | 116 | -43.263 | 18.055 | 49.863 | 1.00 | 9.88 |
| ATOM | 831 | O | ALA | 116 | -42.162 | 17.978 | 49.326 | 1.00 | 13.41 |
| ATOM | 832 | CB | ALA | 116 | -44.101 | 15.894 | 50.689 | 1.00 | 10.10 |
| ATOM | 833 | N | ARG | 117 | -43.586 | 19.020 | 50.636 | 1.00 | 9.81 |
| ATOM | 834 | NH2 | ARG | 117 | -43.870 | 23.560 | 45.115 | 1.00 | 13.10 |
| ATOM | 835 | NH1 | ARG | 117 | -45.496 | 23.020 | 46.568 | 1.00 | 17.40 |
| ATOM | 836 | CZ | ARG | 117 | -44.191 | 23.340 | 46.386 | 1.00 | 16.37 |
| ATOM | 837 | NE | ARG | 117 | -43.268 | 23.465 | 47.330 | 1.00 | 14.91 |
| ATOM | 838 | CD | ARG | 117 | -43.450 | 23.251 | 48.783 | 1.00 | 13.89 |
| ATOM | 839 | CG | ARG | 117 | -43.323 | 21.801 | 49.092 | 1.00 | 10.78 |
| ATOM | 840 | CB | ARG | 117 | -43.392 | 21.470 | 50.596 | 1.00 | 10.30 |
| ATOM | 841 | CA | ARG | 117 | -42.725 | 20.137 | 50.983 | 1.00 | 10.62 |
| ATOM | 842 | C | ARG | 117 | -42.465 | 20.023 | 52.496 | 1.00 | 12.42 |
| ATOM | 843 | O | ARG | 117 | -43.122 | 19.229 | 53.201 | 1.00 | 14.36 |
| ATOM | 844 | N | GLY | 118 | -41.566 | 20.803 | 52.999 | 1.00 | 10.94 |
| ATOM | 845 | CA | GLY | 118 | -41.246 | 20.891 | 54.430 | 1.00 | 14.46 |
| ATOM | 846 | C | GLY | 118 | -40.590 | 19.675 | 55.005 | 1.00 | 13.77 |
| ATOM | 847 | O | GLY | 118 | -40.761 | 19.531 | 56.229 | 1.00 | 14.95 |
| ATOM | 848 | N | GLN | 119 | -39.874 | 18.886 | 54.215 | 1.00 | 11.83 |
| ATOM | 849 | NE2 | GLN | 119 | -42.518 | 16.522 | 54.159 | 1.00 | 27.14 |
| ATOM | 850 | OE1 | GLN | 119 | -41.331 | 14.597 | 53.939 | 1.00 | 29.04 |
| ATOM | 851 | CD | GLN | 119 | -41.505 | 15.779 | 53.683 | 1.00 | 26.05 |
| ATOM | 852 | CG | GLN | 119 | -40.511 | 16.511 | 52.791 | 1.00 | 23.83 |
| ATOM | 853 | CB | GLN | 119 | -39.161 | 16.633 | 53.499 | 1.00 | 15.28 |
| ATOM | 854 | CA | GLN | 119 | -39.228 | 17.649 | 54.654 | 1.00 | 12.25 |
| ATOM | 855 | C | GLN | 119 | -37.819 | 17.866 | 55.191 | 1.00 | 13.13 |
| ATOM | 856 | O | GLN | 119 | -37.023 | 18.655 | 54.674 | 1.00 | 11.96 |
| ATOM | 857 | N | SER | 120 | -37.520 | 17.136 | 56.272 | 1.00 | 12.77 |
| ATOM | 858 | OG | SER | 120 | -36.874 | 16.674 | 59.024 | 0.50 | 13.43 |
| ATOM | 859 | CB | SER | 120 | -36.074 | 17.591 | 58.330 | 0.50 | 15.06 |
| ATOM | 862 | CA | SER | 120 | -36.147 | 17.234 | 56.873 | 1.00 | 11.79 |
| ATOM | 863 | C | SER | 120 | -35.513 | 15.938 | 56.438 | 1.00 | 14.19 |
| ATOM | 864 | O | SER | 120 | -36.167 | 14.855 | 56.352 | 1.00 | 14.17 |
| ATOM | 865 | N | VAL | 121 | -34.228 | 16.035 | 56.037 | 1.00 | 14.53 |
| ATOM | 866 | CG2 | VAL | 121 | -34.392 | 15.445 | 53.235 | 1.00 | 20.02 |
| ATOM | 867 | CG1 | VAL | 121 | -32.537 | 13.814 | 53.494 | 1.00 | 22.53 |
| ATOM | 868 | CB | VAL | 121 | -33.176 | 15.085 | 54.041 | 1.00 | 19.23 |
| ATOM | 869 | CA | VAL | 121 | -33.466 | 14.920 | 55.565 | 1.00 | 14.60 |
| ATOM | 870 | C | VAL | 121 | -32.106 | 14.892 | 56.248 | 1.00 | 17.85 |
| ATOM | 871 | O | VAL | 121 | -31.399 | 15.890 | 56.335 | 1.00 | 16.78 |
| ATOM | 872 | N | SER | 122 | -31.749 | 13.694 | 56.677 | 1.00 | 18.77 |
| ATOM | 873 | OG | SER | 122 | -31.320 | 13.436 | 59.447 | 1.00 | 35.50 |
| ATOM | 874 | CB | SER | 122 | -30.306 | 12.902 | 58.611 | 1.00 | 26.24 |
| ATOM | 875 | CA | SER | 122 | -30.397 | 13.594 | 57.262 | 1.00 | 20.95 |
| ATOM | 876 | C | SER | 122 | -29.504 | 12.911 | 56.238 | 1.00 | 20.78 |
| ATOM | 877 | O | SER | 122 | -29.704 | 11.746 | 55.840 | 1.00 | 25.20 |
| ATOM | 878 | N | TYR | 123 | -28.548 | 13.651 | 55.794 | 1.00 | 19.04 |
| ATOM | 879 | CA | TYR | 123 | -27.479 | 13.164 | 54.927 | 1.00 | 21.72 |
| ATOM | 880 | C | TYR | 123 | -26.478 | 12.615 | 55.995 | 1.00 | 25.29 |
| ATOM | 881 | O | TYR | 123 | -26.521 | 13.015 | 57.187 | 1.00 | 26.53 |

| | | | | | | | | |
|---|---|---|---|---|---|---|---|---|
| ATOM | 882 | CB | TYR | 123 | -26.981 | 14.342 | 54.135 | 1.00 18.93 |
| ATOM | 883 | CG | TYR | 123 | -27.915 | 14.920 | 53.100 | 1.00 18.61 |
| ATOM | 884 | CD1 | TYR | 123 | -27.849 | 16.273 | 52.784 | 1.00 15.70 |
| ATOM | 885 | CD2 | TYR | 123 | -28.840 | 14.144 | 52.381 | 1.00 21.00 |
| ATOM | 886 | CE1 | TYR | 123 | -28.658 | 16.844 | 51.808 | 1.00 15.37 |
| ATOM | 887 | CE2 | TYR | 123 | -29.712 | 14.700 | 51.423 | 1.00 18.34 |
| ATOM | 888 | CZ | TYR | 123 | -29.581 | 16.067 | 51.133 | 1.00 16.62 |
| ATOM | 889 | OH | TYR | 123 | -30.390 | 16.593 | 50.172 | 1.00 15.25 |
| ATOM | 890 | N | PRO | 124 | -25.578 | 11.721 | 55.647 | 1.00 28.48 |
| ATOM | 891 | CG | PRO | 124 | -24.105 | 10.334 | 54.354 | 1.00 32.40 |
| ATOM | 892 | CD | PRO | 124 | -25.391 | 11.155 | 54.297 | 1.00 30.53 |
| ATOM | 893 | CB | PRO | 124 | -23.748 | 10.168 | 55.828 | 1.00 32.32 |
| ATOM | 894 | CA | PRO | 124 | -24.583 | 11.183 | 56.598 | 1.00 31.44 |
| ATOM | 895 | C | PRO | 124 | -23.732 | 12.285 | 57.226 | 1.00 32.68 |
| ATOM | 896 | O | PRO | 124 | -23.355 | 12.124 | 58.408 | 1.00 33.64 |
| ATOM | 897 | N | GLU | 125 | -23.417 | 13.329 | 56.485 | 1.00 32.09 |
| ATOM | 898 | CA | GLU | 125 | -22.646 | 14.515 | 56.843 | 1.00 32.45 |
| ATOM | 899 | C | GLU | 125 | -23.410 | 15.484 | 57.766 | 1.00 33.22 |
| ATOM | 900 | O | GLU | 125 | -22.932 | 15.954 | 58.861 | 1.00 33.87 |
| ATOM | 901 | CB | GLU | 125 | -22.144 | 15.220 | 55.588 | 1.00 28.10 |
| ATOM | 902 | CG | GLU | 125 | -22.899 | 15.278 | 54.299 | 1.00 34.56 |
| ATOM | 903 | CD | GLU | 125 | -23.341 | 14.605 | 53.384 | 0.00 53.35 |
| ATOM | 904 | OE1 | GLU | 125 | -23.517 | 15.100 | 52.231 | 0.00 59.96 |
| ATOM | 905 | OE2 | GLU | 125 | -23.156 | 13.352 | 53.591 | 0.00 58.46 |
| ATOM | 906 | N | GLY | 126 | -24.666 | 15.793 | 57.397 | 1.00 31.75 |
| ATOM | 907 | CA | GLY | 126 | -25.549 | 16.682 | 58.182 | 1.00 28.35 |
| ATOM | 908 | C | GLY | 126 | -27.017 | 16.695 | 57.720 | 1.00 25.07 |
| ATOM | 909 | O | GLY | 126 | -27.393 | 16.107 | 56.682 | 1.00 25.93 |
| ATOM | 910 | N | THR | 127 | -27.811 | 17.417 | 58.486 | 1.00 19.30 |
| ATOM | 911 | CG2 | THR | 127 | -31.485 | 17.638 | 59.616 | 1.00 15.49 |
| ATOM | 912 | OG1 | THR | 127 | -29.548 | 16.190 | 60.199 | 1.00 22.50 |
| ATOM | 913 | CB | THR | 127 | -29.964 | 17.487 | 59.664 | 1.00 14.93 |
| ATOM | 914 | CA | THR | 127 | -29.242 | 17.558 | 58.256 | 1.00 13.91 |
| ATOM | 915 | C | THR | 127 | -29.689 | 18.791 | 57.491 | 1.00 11.25 |
| ATOM | 916 | O | THR | 127 | -29.203 | 19.885 | 57.803 | 1.00 10.59 |
| ATOM | 917 | N | VAL | 128 | -30.649 | 18.626 | 56.584 | 1.00 11.18 |
| ATOM | 918 | CA | VAL | 128 | -31.201 | 19.747 | 55.791 | 1.00 9.77 |
| ATOM | 919 | C | VAL | 128 | -32.688 | 19.787 | 56.164 | 1.00 8.45 |
| ATOM | 920 | O | VAL | 128 | -33.182 | 18.697 | 56.393 | 1.00 11.45 |
| ATOM | 921 | CB | VAL | 128 | -30.956 | 19.633 | 54.298 | 1.00 7.25 |
| ATOM | 922 | CG1 | VAL | 128 | -29.466 | 19.790 | 54.013 | 1.00 11.55 |
| ATOM | 923 | CG2 | VAL | 128 | -31.377 | 18.285 | 53.735 | 1.00 9.36 |
| ATOM | 924 | N | THR | 129 | -33.266 | 20.960 | 56.248 | 1.00 9.49 |
| ATOM | 925 | CG2 | THR | 129 | -34.182 | 21.202 | 59.125 | 1.00 18.71 |
| ATOM | 926 | OG1 | THR | 129 | -34.282 | 23.173 | 57.758 | 1.00 14.40 |
| ATOM | 927 | CB | THR | 129 | -34.884 | 21.913 | 57.959 | 1.00 8.96 |
| ATOM | 928 | CA | THR | 129 | -34.680 | 21.088 | 56.613 | 1.00 9.66 |
| ATOM | 929 | C | THR | 129 | -35.407 | 21.804 | 55.487 | 1.00 10.11 |
| ATOM | 930 | O | THR | 129 | -34.796 | 22.467 | 54.615 | 1.00 10.92 |
| ATOM | 931 | N | ASN | 130 | -36.709 | 21.619 | 55.563 | 1.00 10.84 |
| ATOM | 932 | ND2 | ASN | 130 | -38.570 | 25.717 | 53.765 | 1.00 35.10 |
| ATOM | 933 | OD1 | ASN | 130 | -39.854 | 23.969 | 54.369 | 1.00 28.19 |
| ATOM | 934 | CG | ASN | 130 | -38.739 | 24.527 | 54.362 | 1.00 30.11 |
| ATOM | 935 | CB | ASN | 130 | -37.496 | 23.827 | 54.952 | 1.00 17.09 |

| | | | | | | | | |
|---|---|---|---|---|---|---|---|---|
| ATOM | 936 | CA | ASN | 130 | -37.620 | 22.299 | 54.616 | 1.00 12.34 |
| ATOM | 937 | C | ASN | 130 | -37.388 | 21.988 | 53.136 | 1.00 11.59 |
| ATOM | 938 | O | ASN | 130 | -37.557 | 22.883 | 52.268 | 1.00 11.46 |
| ATOM | 939 | N | MET | 131 | -37.056 | 20.742 | 52.880 | 1.00  9.76 |
| ATOM | 940 | CE | MET | 131 | -33.020 | 20.248 | 50.187 | 1.00 16.57 |
| ATOM | 941 | SD | MET | 131 | -33.597 | 21.082 | 51.629 | 1.00 20.94 |
| ATOM | 942 | CG | MET | 131 | -34.411 | 19.573 | 52.379 | 1.00  9.59 |
| ATOM | 943 | CB | MET | 131 | -35.664 | 19.199 | 51.580 | 1.00  5.73 |
| ATOM | 944 | CA | MET | 131 | -36.732 | 20.297 | 51.529 | 1.00  9.93 |
| ATOM | 945 | C | MET | 131 | -38.007 | 19.797 | 50.840 | 1.00  9.00 |
| ATOM | 946 | O | MET | 131 | -38.962 | 19.372 | 51.519 | 1.00 10.48 |
| ATOM | 947 | N | THR | 132 | -37.995 | 19.869 | 49.527 | 1.00  8.82 |
| ATOM | 948 | CA | THR | 132 | -39.129 | 19.393 | 48.710 | 1.00  5.72 |
| ATOM | 949 | C | THR | 132 | -38.769 | 18.054 | 48.108 | 1.00  7.44 |
| ATOM | 950 | O | THR | 132 | -37.719 | 17.850 | 47.428 | 1.00  9.83 |
| ATOM | 951 | CB | THR | 132 | -39.497 | 20.516 | 47.675 | 1.00  6.44 |
| ATOM | 952 | OG1 | THR | 132 | -39.851 | 21.700 | 48.434 | 1.00  9.35 |
| ATOM | 953 | CG2 | THR | 132 | -40.681 | 20.100 | 46.737 | 1.00  7.59 |
| ATOM | 954 | N | ARG | 133 | -39.640 | 17.061 | 48.306 | 1.00  4.85 |
| ATOM | 955 | NH2 | ARG | 133 | -42.116 | 12.875 | 51.526 | 1.00 39.69 |
| ATOM | 956 | NH1 | ARG | 133 | -43.846 | 11.985 | 50.304 | 1.00 32.03 |
| ATOM | 957 | CZ | ARG | 133 | -42.539 | 12.272 | 50.397 | 1.00 36.90 |
| ATOM | 958 | NE | ARG | 133 | -41.666 | 11.948 | 49.418 | 1.00 28.98 |
| ATOM | 959 | CD | ARG | 133 | -40.253 | 12.204 | 49.398 | 1.00 20.06 |
| ATOM | 960 | CG | ARG | 133 | -39.832 | 13.218 | 48.354 | 1.00 11.77 |
| ATOM | 961 | CB | ARG | 133 | -40.079 | 14.660 | 48.801 | 1.00  6.59 |
| ATOM | 962 | CA | ARG | 133 | -39.443 | 15.674 | 47.833 | 1.00  6.76 |
| ATOM | 963 | C | ARG | 133 | -40.092 | 15.457 | 46.455 | 1.00  7.46 |
| ATOM | 964 | O | ARG | 133 | -41.227 | 15.963 | 46.241 | 1.00  9.38 |
| ATOM | 965 | N | THR | 134 | -39.360 | 14.793 | 45.552 | 1.00  9.68 |
| ATOM | 966 | CG2 | THR | 134 | -39.353 | 17.060 | 43.521 | 1.00  7.44 |
| ATOM | 967 | OG1 | THR | 134 | -38.110 | 15.030 | 42.788 | 1.00  8.17 |
| ATOM | 968 | CB | THR | 134 | -39.392 | 15.603 | 43.141 | 1.00  8.74 |
| ATOM | 969 | CA | THR | 134 | -39.921 | 14.565 | 44.202 | 1.00  8.24 |
| ATOM | 970 | C | THR | 134 | -39.576 | 13.135 | 43.785 | 1.00  8.06 |
| ATOM | 971 | O | THR | 134 | -38.694 | 12.518 | 44.396 | 1.00  9.92 |
| ATOM | 972 | N | THR | 135 | -40.301 | 12.622 | 42.770 | 1.00  7.24 |
| ATOM | 973 | CG2 | THR | 135 | -42.463 | 10.541 | 42.733 | 1.00 12.10 |
| ATOM | 974 | OG1 | THR | 135 | -41.763 | 11.403 | 40.497 | 1.00 11.13 |
| ATOM | 975 | CB | THR | 135 | -41.362 | 10.601 | 41.650 | 1.00 10.58 |
| ATOM | 976 | CA | THR | 135 | -40.037 | 11.294 | 42.228 | 1.00  8.03 |
| ATOM | 977 | C | THR | 135 | -38.974 | 11.340 | 41.147 | 1.00  7.98 |
| ATOM | 978 | O | THR | 135 | -38.731 | 10.327 | 40.471 | 1.00  9.10 |
| ATOM | 979 | N | VAL | 136 | -38.326 | 12.452 | 40.852 | 1.00 10.38 |
| ATOM | 980 | CG2 | VAL | 136 | -38.483 | 14.754 | 39.130 | 1.00  6.65 |
| ATOM | 981 | CG1 | VAL | 136 | -36.094 | 14.300 | 38.374 | 1.00 10.08 |
| ATOM | 982 | CB | VAL | 136 | -37.136 | 14.096 | 39.495 | 1.00  9.89 |
| ATOM | 983 | CA | VAL | 136 | -37.296 | 12.595 | 39.813 | 1.00  9.10 |
| ATOM | 984 | C | VAL | 136 | -35.990 | 11.927 | 40.235 | 1.00  9.23 |
| ATOM | 985 | O | VAL | 136 | -35.640 | 12.113 | 41.414 | 1.00 11.00 |
| ATOM | 986 | N | CYS | 137 | -35.273 | 11.188 | 39.408 | 1.00  7.90 |
| ATOM | 987 | CA | CYS | 137 | -33.997 | 10.564 | 39.780 | 1.00  8.61 |
| ATOM | 988 | C | CYS | 137 | -32.841 | 11.600 | 39.681 | 1.00  9.07 |
| ATOM | 989 | O | CYS | 137 | -33.024 | 12.659 | 39.015 | 1.00  9.87 |

| | | | | | | | | | |
|---|---|---|---|---|---|---|---|---|---|
| ATOM | 990 | CB | CYS | 137 | -33.702 | 9.452 | 38.761 | 1.00 | 8.35 |
| ATOM | 991 | SG | CYS | 137 | -33.425 | 10.011 | 37.031 | 1.00 | 11.68 |
| ATOM | 992 | N | ALA | 138 | -31.687 | 11.330 | 40.300 | 1.00 | 7.09 |
| ATOM | 993 | CB | ALA | 138 | -30.467 | 13.454 | 41.104 | 1.00 | 8.40 |
| ATOM | 994 | CA | ALA | 138 | -30.503 | 12.207 | 40.220 | 1.00 | 8.25 |
| ATOM | 995 | C | ALA | 138 | -29.294 | 11.352 | 40.568 | 1.00 | 8.58 |
| ATOM | 996 | O | ALA | 138 | -29.409 | 10.287 | 41.211 | 1.00 | 10.28 |
| ATOM | 997 | N | GLU | 139 | -28.105 | 11.803 | 40.178 | 1.00 | 9.17 |
| ATOM | 998 | OE2 | GLU | 139 | -27.880 | 7.597 | 37.175 | 1.00 | 10.81 |
| ATOM | 999 | OE1 | GLU | 139 | -25.864 | 8.348 | 37.135 | 1.00 | 10.87 |
| ATOM | 1000 | CD | GLU | 139 | -26.946 | 8.270 | 37.673 | 1.00 | 12.62 |
| ATOM | 1001 | CG | GLU | 139 | -27.289 | 9.053 | 38.912 | 1.00 | 10.79 |
| ATOM | 1002 | CB | GLU | 139 | -26.414 | 10.298 | 39.196 | 1.00 | 8.09 |
| ATOM | 1003 | CA | GLU | 139 | -26.818 | 11.099 | 40.431 | 1.00 | 9.02 |
| ATOM | 1004 | C | GLU | 139 | -25.776 | 12.156 | 40.775 | 1.00 | 9.85 |
| ATOM | 1005 | O | GLU | 139 | -25.966 | 13.362 | 40.507 | 1.00 | 9.59 |
| ATOM | 1006 | N | PRO | 140 | -24.677 | 11.769 | 41.394 | 1.00 | 11.00 |
| ATOM | 1007 | CG | PRO | 140 | -23.255 | 10.606 | 42.890 | 1.00 | 10.81 |
| ATOM | 1008 | CD | PRO | 140 | -24.305 | 10.376 | 41.788 | 1.00 | 10.23 |
| ATOM | 1009 | CB | PRO | 140 | -22.595 | 11.921 | 42.569 | 1.00 | 13.07 |
| ATOM | 1010 | CA | PRO | 140 | -23.611 | 12.741 | 41.794 | 1.00 | 10.28 |
| ATOM | 1011 | C | PRO | 140 | -23.095 | 13.561 | 40.611 | 1.00 | 9.93 |
| ATOM | 1012 | O | PRO | 140 | -22.846 | 13.081 | 39.498 | 1.00 | 11.30 |
| ATOM | 1013 | N | GLY | 141 | -23.015 | 14.865 | 40.884 | 1.00 | 7.17 |
| ATOM | 1014 | CA | GLY | 141 | -22.596 | 15.857 | 39.927 | 1.00 | 7.59 |
| ATOM | 1015 | C | GLY | 141 | -23.845 | 16.611 | 39.448 | 1.00 | 6.72 |
| ATOM | 1016 | O | GLY | 141 | -23.742 | 17.715 | 38.907 | 1.00 | 7.49 |
| ATOM | 1017 | N | ASP | 142 | -25.050 | 16.077 | 39.671 | 1.00 | 7.35 |
| ATOM | 1018 | CA | ASP | 142 | -26.325 | 16.710 | 39.296 | 1.00 | 6.21 |
| ATOM | 1019 | C | ASP | 142 | -26.663 | 17.752 | 40.369 | 1.00 | 5.40 |
| ATOM | 1020 | O | ASP | 142 | -27.522 | 18.627 | 40.062 | 1.00 | 3.95 |
| ATOM | 1021 | CB | ASP | 142 | -27.497 | 15.784 | 39.058 | 1.00 | 7.83 |
| ATOM | 1022 | CG | ASP | 142 | -27.531 | 14.867 | 37.860 | 1.00 | 7.53 |
| ATOM | 1023 | OD1 | ASP | 142 | -28.075 | 13.736 | 37.908 | 1.00 | 7.92 |
| ATOM | 1024 | OD2 | ASP | 142 | -27.048 | 15.355 | 36.863 | 1.00 | 6.85 |
| ATOM | 1025 | N | SER | 143 | -26.112 | 17.668 | 41.546 | 1.00 | 5.60 |
| ATOM | 1026 | CA | SER | 143 | -26.422 | 18.670 | 42.589 | 1.00 | 5.95 |
| ATOM | 1027 | C | SER | 143 | -26.287 | 20.098 | 42.102 | 1.00 | 7.22 |
| ATOM | 1028 | O | SER | 143 | -25.328 | 20.407 | 41.346 | 1.00 | 7.03 |
| ATOM | 1029 | CB | SER | 143 | -25.451 | 18.527 | 43.777 | 1.00 | 7.47 |
| ATOM | 1030 | OG | SER | 143 | -25.764 | 17.255 | 44.327 | 1.00 | 11.26 |
| ATOM | 1031 | N | GLY | 144 | -27.206 | 20.956 | 42.571 | 1.00 | 5.35 |
| ATOM | 1032 | CA | GLY | 144 | -27.301 | 22.370 | 42.249 | 1.00 | 5.48 |
| ATOM | 1033 | C | GLY | 144 | -28.051 | 22.665 | 40.945 | 1.00 | 6.00 |
| ATOM | 1034 | O | GLY | 144 | -28.334 | 23.858 | 40.698 | 1.00 | 7.24 |
| ATOM | 1035 | N | GLY | 145 | -28.295 | 21.671 | 40.140 | 1.00 | 5.00 |
| ATOM | 1036 | CA | GLY | 145 | -28.959 | 21.818 | 38.828 | 1.00 | 5.08 |
| ATOM | 1037 | C | GLY | 145 | -30.400 | 22.272 | 38.981 | 1.00 | 6.80 |
| ATOM | 1038 | O | GLY | 145 | -31.096 | 22.093 | 40.013 | 1.00 | 8.09 |
| ATOM | 1039 | N | SER | 146 | -31.016 | 22.823 | 37.953 | 1.00 | 4.98 |
| ATOM | 1040 | CA | SER | 146 | -32.375 | 23.344 | 37.961 | 1.00 | 4.54 |
| ATOM | 1041 | C | SER | 146 | -33.561 | 22.389 | 38.160 | 1.00 | 5.95 |
| ATOM | 1042 | O | SER | 146 | -33.513 | 21.305 | 37.566 | 1.00 | 6.69 |
| ATOM | 1043 | CB | SER | 146 | -32.609 | 23.870 | 36.500 | 1.00 | 4.69 |

| | | | | | | | | |
|---|---|---|---|---|---|---|---|---|
| ATOM | 1044 | OG | SER | 146 | -31.487 | 24.440 | 35.945 | 1.00 7.80 |
| ATOM | 1045 | N | TYR | 147 | -34.584 | 22.813 | 38.888 | 1.00 4.96 |
| ATOM | 1046 | OH | TYR | 147 | -34.686 | 16.409 | 41.718 | 1.00 15.17 |
| ATOM | 1047 | CD2 | TYR | 147 | -36.809 | 19.212 | 40.614 | 1.00 8.25 |
| ATOM | 1048 | CE2 | TYR | 147 | -36.419 | 17.910 | 40.955 | 1.00 10.83 |
| ATOM | 1049 | CZ | TYR | 147 | -35.130 | 17.695 | 41.413 | 1.00 13.00 |
| ATOM | 1050 | CE1 | TYR | 147 | -34.196 | 18.722 | 41.524 | 1.00 8.41 |
| ATOM | 1051 | CD1 | TYR | 147 | -34.601 | 20.028 | 41.200 | 1.00 7.28 |
| ATOM | 1052 | CG | TYR | 147 | -35.885 | 20.262 | 40.762 | 1.00 6.98 |
| ATOM | 1053 | CB | TYR | 147 | -36.258 | 21.677 | 40.422 | 1.00 5.48 |
| ATOM | 1054 | CA | TYR | 147 | -35.875 | 22.091 | 39.028 | 1.00 5.55 |
| ATOM | 1055 | C | TYR | 147 | -36.829 | 23.167 | 38.409 | 1.00 6.41 |
| ATOM | 1056 | O | TYR | 147 | -36.859 | 24.306 | 38.918 | 1.00 6.54 |
| ATOM | 1057 | N | ILE | 148 | -37.559 | 22.845 | 37.365 | 1.00 5.67 |
| ATOM | 1058 | CA | ILE | 148 | -38.454 | 23.821 | 36.710 | 1.00 6.64 |
| ATOM | 1059 | C | ILE | 148 | -39.776 | 23.154 | 36.317 | 1.00 6.20 |
| ATOM | 1060 | O | ILE | 148 | -39.743 | 21.993 | 35.834 | 1.00 6.60 |
| ATOM | 1061 | CB | ILE | 148 | -37.661 | 24.408 | 35.475 | 1.00 8.25 |
| ATOM | 1062 | CG1 | ILE | 148 | -38.445 | 25.567 | 34.843 | 1.00 10.19 |
| ATOM | 1063 | CG2 | ILE | 148 | -37.269 | 23.309 | 34.443 | 1.00 11.02 |
| ATOM | 1064 | CD1 | ILE | 148 | -37.739 | 26.438 | 33.738 | 1.00 11.12 |
| ATOM | 1065 | N | SER | 149 | -40.878 | 23.912 | 36.472 | 1.00 6.67 |
| ATOM | 1066 | OG | SER | 149 | -42.874 | 22.350 | 38.136 | 1.00 15.36 |
| ATOM | 1067 | CB | SER | 149 | -43.209 | 23.415 | 37.231 | 1.00 9.17 |
| ATOM | 1068 | CA | SER | 149 | -42.219 | 23.396 | 36.098 | 1.00 7.08 |
| ATOM | 1069 | C | SER | 149 | -42.712 | 24.364 | 35.000 | 1.00 7.85 |
| ATOM | 1070 | O | SER | 149 | -43.087 | 25.496 | 35.341 | 1.00 8.98 |
| ATOM | 1071 | N | GLY | 150 | -42.632 | 23.897 | 33.754 | 1.00 10.00 |
| ATOM | 1072 | CA | GLY | 150 | -43.066 | 24.798 | 32.663 | 1.00 11.86 |
| ATOM | 1073 | C | GLY | 150 | -41.990 | 25.883 | 32.482 | 1.00 8.97 |
| ATOM | 1074 | O | GLY | 150 | -40.850 | 25.591 | 32.148 | 1.00 12.79 |
| ATOM | 1075 | N | THR | 151 | -42.463 | 27.096 | 32.745 | 1.00 9.09 |
| ATOM | 1076 | CG2 | THR | 151 | -42.428 | 29.087 | 30.347 | 1.00 13.40 |
| ATOM | 1077 | OG1 | THR | 151 | -43.398 | 29.844 | 32.497 | 1.00 13.13 |
| ATOM | 1078 | CB | THR | 151 | -42.170 | 29.426 | 31.816 | 1.00 11.88 |
| ATOM | 1079 | CA | THR | 151 | -41.527 | 28.257 | 32.661 | 1.00 10.61 |
| ATOM | 1080 | C | THR | 151 | -41.196 | 28.758 | 34.085 | 1.00 9.76 |
| ATOM | 1081 | O | THR | 151 | -40.553 | 29.810 | 34.179 | 1.00 10.13 |
| ATOM | 1082 | N | GLN | 152 | -41.628 | 28.099 | 35.157 | 1.00 6.87 |
| ATOM | 1083 | CA | GLN | 152 | -41.440 | 28.600 | 36.494 | 1.00 7.20 |
| ATOM | 1084 | C | GLN | 152 | -40.304 | 27.909 | 37.266 | 1.00 8.56 |
| ATOM | 1085 | O | GLN | 152 | -40.488 | 26.681 | 37.461 | 1.00 12.38 |
| ATOM | 1086 | CB | GLN | 152 | -42.770 | 28.493 | 37.286 | 1.00 6.03 |
| ATOM | 1087 | CG | GLN | 152 | -43.935 | 29.238 | 36.607 | 1.00 9.11 |
| ATOM | 1088 | CD | GLN | 152 | -43.668 | 30.705 | 36.459 | 1.00 7.44 |
| ATOM | 1089 | OE1 | GLN | 152 | -43.411 | 31.422 | 37.422 | 1.00 11.18 |
| ATOM | 1090 | NE2 | GLN | 152 | -43.686 | 31.229 | 35.247 | 1.00 15.32 |
| ATOM | 1091 | N | ALA | 153 | -39.288 | 28.691 | 37.696 | 1.00 7.16 |
| ATOM | 1092 | CA | ALA | 153 | -38.166 | 28.065 | 38.442 | 1.00 6.99 |
| ATOM | 1093 | C | ALA | 153 | -38.696 | 27.572 | 39.786 | 1.00 6.78 |
| ATOM | 1094 | O | ALA | 153 | -39.432 | 28.329 | 40.450 | 1.00 8.03 |
| ATOM | 1095 | CB | ALA | 153 | -37.062 | 29.133 | 38.567 | 1.00 6.81 |
| ATOM | 1096 | N | GLN | 154 | -38.383 | 26.349 | 40.198 | 1.00 4.41 |
| ATOM | 1097 | CA | GLN | 154 | -38.827 | 25.782 | 41.460 | 1.00 6.90 |

| | | | | | | | | |
|---|---|---|---|---|---|---|---|---|
| ATOM | 1098 | C | GLN | 154 | -37.692 | 25.687 | 42.494 | 1.00 7.22 |
| ATOM | 1099 | O | GLN | 154 | -37.931 | 26.098 | 43.640 | 1.00 7.22 |
| ATOM | 1100 | CB | GLN | 154 | -39.459 | 24.374 | 41.221 | 1.00 6.12 |
| ATOM | 1101 | CG | GLN | 154 | -40.644 | 24.402 | 40.211 | 1.00 6.24 |
| ATOM | 1102 | CD | GLN | 154 | -41.732 | 25.321 | 40.671 | 1.00 9.04 |
| ATOM | 1103 | OE1 | GLN | 154 | -42.271 | 25.234 | 41.795 | 1.00 9.56 |
| ATOM | 1104 | NE2 | GLN | 154 | -42.164 | 26.267 | 39.859 | 1.00 4.50 |
| ATOM | 1105 | N | GLY | 155 | -36.547 | 25.153 | 42.078 | 1.00 7.56 |
| ATOM | 1106 | CA | GLY | 155 | -35.475 | 24.954 | 43.098 | 1.00 7.31 |
| ATOM | 1107 | C | GLY | 155 | -34.202 | 24.370 | 42.501 | 1.00 7.69 |
| ATOM | 1108 | O | GLY | 155 | -34.029 | 24.335 | 41.280 | 1.00 7.17 |
| ATOM | 1109 | N | VAL | 156 | -33.252 | 24.073 | 43.370 | 1.00 6.91 |
| ATOM | 1110 | CA | VAL | 156 | -31.925 | 23.515 | 42.968 | 1.00 7.24 |
| ATOM | 1111 | C | VAL | 156 | -31.760 | 22.136 | 43.631 | 1.00 5.91 |
| ATOM | 1112 | O | VAL | 156 | -32.096 | 21.942 | 44.815 | 1.00 6.78 |
| ATOM | 1113 | CB | VAL | 156 | -30.786 | 24.527 | 43.154 | 1.00 6.19 |
| ATOM | 1114 | CG1 | VAL | 156 | -31.048 | 25.862 | 42.407 | 1.00 5.61 |
| ATOM | 1115 | CG2 | VAL | 156 | -30.409 | 24.754 | 44.616 | 1.00 8.17 |
| ATOM | 1116 | N | THR | 157 | -31.186 | 21.164 | 42.911 | 1.00 3.82 |
| ATOM | 1117 | CG2 | THR | 157 | -30.184 | 17.395 | 42.515 | 1.00 4.16 |
| ATOM | 1118 | OG1 | THR | 157 | -30.991 | 19.138 | 41.073 | 1.00 8.01 |
| ATOM | 1119 | CB | THR | 157 | -30.243 | 18.893 | 42.293 | 1.00 3.37 |
| ATOM | 1120 | CA | THR | 157 | -30.971 | 19.799 | 43.383 | 1.00 4.97 |
| ATOM | 1121 | C | THR | 157 | -30.083 | 19.754 | 44.627 | 1.00 5.89 |
| ATOM | 1122 | O | THR | 157 | -28.979 | 20.281 | 44.589 | 1.00 5.74 |
| ATOM | 1123 | N | SER | 158 | -30.588 | 19.070 | 45.635 | 1.00 5.99 |
| ATOM | 1124 | CA | SER | 158 | -29.830 | 18.914 | 46.876 | 1.00 7.64 |
| ATOM | 1125 | C | SER | 158 | -29.316 | 17.473 | 46.969 | 1.00 10.26 |
| ATOM | 1126 | O | SER | 158 | -28.087 | 17.229 | 47.132 | 1.00 10.04 |
| ATOM | 1127 | CB | SER | 158 | -30.619 | 19.304 | 48.134 | 1.00 8.30 |
| ATOM | 1128 | OG | SER | 158 | -29.853 | 18.975 | 49.296 | 1.00 9.39 |
| ATOM | 1129 | N | GLY | 159 | -30.150 | 16.443 | 46.900 | 1.00 9.83 |
| ATOM | 1130 | CA | GLY | 159 | -29.635 | 15.060 | 47.040 | 1.00 9.90 |
| ATOM | 1131 | C | GLY | 159 | -30.756 | 14.048 | 47.006 | 1.00 12.82 |
| ATOM | 1132 | O | GLY | 159 | -31.878 | 14.478 | 46.680 | 1.00 13.31 |
| ATOM | 1133 | N | GLY | 160 | -30.510 | 12.792 | 47.352 | 1.00 12.00 |
| ATOM | 1134 | CA | GLY | 160 | -31.646 | 11.846 | 47.257 | 1.00 12.56 |
| ATOM | 1135 | C | GLY | 160 | -31.091 | 10.410 | 47.219 | 1.00 15.35 |
| ATOM | 1136 | O | GLY | 160 | -29.988 | 10.197 | 47.741 | 1.00 15.70 |
| ATOM | 1137 | N | SER | 161 | -31.869 | 9.497 | 46.679 | 1.00 13.10 |
| ATOM | 1138 | OG | SER | 161 | -33.410 | 7.381 | 47.752 | 1.00 18.73 |
| ATOM | 1139 | CB | SER | 161 | -31.996 | 7.324 | 47.833 | 1.00 16.84 |
| ATOM | 1140 | CA | SER | 161 | -31.379 | 8.089 | 46.671 | 1.00 14.66 |
| ATOM | 1141 | C | SER | 161 | -31.670 | 7.448 | 45.325 | 1.00 13.50 |
| ATOM | 1142 | O | SER | 161 | -32.491 | 8.066 | 44.640 | 1.00 13.10 |
| ATOM | 1143 | N | GLY | 162 | -31.078 | 6.310 | 45.040 | 1.00 11.84 |
| ATOM | 1144 | CA | GLY | 162 | -31.318 | 5.641 | 43.734 | 1.00 12.53 |
| ATOM | 1145 | C | GLY | 162 | -30.457 | 6.331 | 42.672 | 1.00 12.12 |
| ATOM | 1146 | O | GLY | 162 | -29.545 | 7.088 | 42.957 | 1.00 11.79 |
| ATOM | 1147 | N | ASN | 163 | -30.786 | 6.068 | 41.407 | 1.00 10.66 |
| ATOM | 1148 | CA | ASN | 163 | -30.058 | 6.588 | 40.269 | 1.00 8.29 |
| ATOM | 1149 | C | ASN | 163 | -31.033 | 6.671 | 39.088 | 1.00 11.02 |
| ATOM | 1150 | O | ASN | 163 | -32.220 | 6.293 | 39.233 | 1.00 10.33 |
| ATOM | 1151 | CB | ASN | 163 | -28.827 | 5.741 | 39.950 | 1.00 10.88 |

| | | | | | | | | |
|---|---|---|---|---|---|---|---|---|
| ATOM | 1152 | CG | ASN | 163 | -29.238 | 4.312 | 39.578 | 1.00 14.23 |
| ATOM | 1153 | OD1 | ASN | 163 | -29.966 | 3.979 | 38.660 | 1.00 11.31 |
| ATOM | 1154 | ND2 | ASN | 163 | -28.649 | 3.362 | 40.334 | 1.00 18.48 |
| ATOM | 1155 | N | CYS | 164 | -30.499 | 7.132 | 37.956 | 1.00 10.86 |
| ATOM | 1156 | CA | CYS | 164 | -31.420 | 7.271 | 36.806 | 1.00 11.83 |
| ATOM | 1157 | C | CYS | 164 | -31.687 | 6.006 | 35.998 | 1.00 13.69 |
| ATOM | 1158 | O | CYS | 164 | -32.428 | 6.145 | 34.993 | 1.00 15.15 |
| ATOM | 1159 | CB | CYS | 164 | -31.100 | 8.500 | 35.971 | 1.00 10.31 |
| ATOM | 1160 | SG | CYS | 164 | -31.448 | 10.097 | 36.795 | 1.00 9.57 |
| ATOM | 1161 | N | ARG | 165 | -31.110 | 4.919 | 36.364 | 1.00 11.68 |
| ATOM | 1162 | NH2 | ARG | 165 | -26.089 | 2.173 | 38.339 | 1.00 59.15 |
| ATOM | 1163 | NH1 | ARG | 165 | -25.617 | 4.096 | 37.196 | 1.00 58.35 |
| ATOM | 1164 | CZ | ARG | 165 | -26.258 | 2.909 | 37.212 | 1.00 55.39 |
| ATOM | 1165 | NE | ARG | 165 | -27.054 | 2.356 | 36.310 | 1.00 47.93 |
| ATOM | 1166 | CD | ARG | 165 | -27.631 | 2.632 | 35.037 | 1.00 40.44 |
| ATOM | 1167 | CG | ARG | 165 | -28.933 | 3.381 | 34.944 | 1.00 31.56 |
| ATOM | 1168 | CB | ARG | 165 | -30.065 | 2.765 | 35.785 | 1.00 18.33 |
| ATOM | 1169 | CA | ARG | 165 | -31.324 | 3.621 | 35.703 | 1.00 17.34 |
| ATOM | 1170 | C | ARG | 165 | -32.498 | 2.928 | 36.433 | 1.00 14.57 |
| ATOM | 1171 | O | ARG | 165 | -33.499 | 2.588 | 35.782 | 1.00 15.39 |
| ATOM | 1172 | N | THR | 166 | -32.347 | 2.784 | 37.751 | 1.00 12.62 |
| ATOM | 1173 | CG2 | THR | 166 | -31.557 | 0.620 | 39.350 | 1.00 18.19 |
| ATOM | 1174 | OG1 | THR | 166 | -32.296 | 2.562 | 40.679 | 1.00 17.67 |
| ATOM | 1175 | CB | THR | 166 | -32.716 | 1.474 | 39.795 | 1.00 16.75 |
| ATOM | 1176 | CA | THR | 166 | -33.407 | 2.140 | 38.540 | 1.00 13.18 |
| ATOM | 1177 | C | THR | 166 | -34.528 | 3.049 | 39.012 | 1.00 15.18 |
| ATOM | 1178 | O | THR | 166 | -35.581 | 2.528 | 39.436 | 1.00 16.50 |
| ATOM | 1179 | N | GLY | 167 | -34.296 | 4.347 | 39.040 | 1.00 13.17 |
| ATOM | 1180 | CA | GLY | 167 | -35.255 | 5.345 | 39.536 | 1.00 13.42 |
| ATOM | 1181 | C | GLY | 167 | -34.815 | 5.663 | 40.997 | 1.00 14.50 |
| ATOM | 1182 | O | GLY | 167 | -33.957 | 4.993 | 41.596 | 1.00 13.35 |
| ATOM | 1183 | N | GLY | 168 | -35.330 | 6.773 | 41.562 | 1.00 14.99 |
| ATOM | 1184 | CA | GLY | 168 | -34.923 | 7.118 | 42.940 | 1.00 12.40 |
| ATOM | 1185 | C | GLY | 168 | -35.852 | 8.241 | 43.371 | 1.00 15.29 |
| ATOM | 1186 | O | GLY | 168 | -36.909 | 8.509 | 42.754 | 1.00 14.71 |
| ATOM | 1187 | N | THR | 169 | -35.422 | 8.845 | 44.471 | 1.00 14.65 |
| ATOM | 1188 | CG2 | THR | 169 | -37.341 | 10.701 | 47.345 | 1.00 11.85 |
| ATOM | 1189 | OG1 | THR | 169 | -37.698 | 8.540 | 46.281 | 1.00 16.91 |
| ATOM | 1190 | CB | THR | 169 | -36.711 | 9.582 | 46.529 | 1.00 14.83 |
| ATOM | 1191 | CA | THR | 169 | -36.177 | 9.973 | 45.077 | 1.00 13.13 |
| ATOM | 1192 | C | THR | 169 | -35.165 | 11.121 | 45.248 | 1.00 11.43 |
| ATOM | 1193 | O | THR | 169 | -34.007 | 10.807 | 45.611 | 1.00 11.62 |
| ATOM | 1194 | N | THR | 170 | -35.621 | 12.315 | 44.946 | 1.00 8.52 |
| ATOM | 1195 | CG2 | THR | 170 | -33.232 | 12.956 | 43.075 | 1.00 6.44 |
| ATOM | 1196 | OG1 | THR | 170 | -35.355 | 14.161 | 43.068 | 1.00 19.35 |
| ATOM | 1197 | CB | THR | 170 | -34.090 | 13.942 | 43.798 | 1.00 12.63 |
| ATOM | 1198 | CA | THR | 170 | -34.667 | 13.406 | 45.165 | 1.00 8.99 |
| ATOM | 1199 | C | THR | 170 | -35.363 | 14.555 | 45.880 | 1.00 11.07 |
| ATOM | 1200 | O | THR | 170 | -36.582 | 14.758 | 45.736 | 1.00 12.91 |
| ATOM | 1201 | N | PHE | 171 | -34.531 | 15.291 | 46.609 | 1.00 9.07 |
| ATOM | 1202 | CD2 | PHE | 171 | -36.450 | 15.430 | 50.154 | 1.00 12.37 |
| ATOM | 1203 | CE2 | PHE | 171 | -37.017 | 14.281 | 50.750 | 1.00 12.72 |
| ATOM | 1204 | CZ | PHE | 171 | -36.332 | 13.053 | 50.718 | 1.00 14.13 |
| ATOM | 1205 | CE1 | PHE | 171 | -35.064 | 12.901 | 50.136 | 1.00 11.85 |

```
ATOM   1206  CD1  PHE  171   -34.501  14.041  49.547  1.00  12.01
ATOM   1207  CG   PHE  171   -35.187  15.262  49.538  1.00  14.42
ATOM   1208  CB   PHE  171   -34.500  16.430  48.855  1.00   8.65
ATOM   1209  CA   PHE  171   -34.946  16.484  47.353  1.00  10.31
ATOM   1210  C    PHE  171   -34.276  17.746  46.736  1.00   9.69
ATOM   1211  O    PHE  171   -33.096  17.749  46.336  1.00  10.28
ATOM   1212  N    TYR  172   -35.022  18.818  46.721  1.00   6.76
ATOM   1213  OH   TYR  172   -40.405  22.042  43.789  1.00  10.33
ATOM   1214  CD2  TYR  172   -37.368  19.978  44.053  1.00   7.13
ATOM   1215  CE2  TYR  172   -38.680  20.393  43.754  1.00   9.56
ATOM   1216  CZ   TYR  172   -39.128  21.645  44.088  1.00  11.06
ATOM   1217  CE1  TYR  172   -38.255  22.544  44.740  1.00   7.89
ATOM   1218  CD1  TYR  172   -36.943  22.125  44.984  1.00   5.66
ATOM   1219  CG   TYR  172   -36.496  20.849  44.693  1.00   5.21
ATOM   1220  CB   TYR  172   -35.049  20.462  44.892  1.00   6.84
ATOM   1221  CA   TYR  172   -34.465  20.077  46.256  1.00   7.19
ATOM   1222  C    TYR  172   -34.711  21.217  47.245  1.00   6.71
ATOM   1223  O    TYR  172   -35.673  21.172  48.064  1.00   8.96
ATOM   1224  N    GLN  173   -33.781  22.185  47.157  1.00   5.53
ATOM   1225  NE2  GLN  173   -33.746  26.714  50.033  1.00   6.96
ATOM   1226  OE1  GLN  173   -32.289  25.169  50.891  1.00  10.23
ATOM   1227  CD   GLN  173   -32.795  25.753  49.933  1.00   9.42
ATOM   1228  CG   GLN  173   -32.411  25.493  48.482  1.00   3.75
ATOM   1229  CB   GLN  173   -32.463  24.037  48.054  1.00   8.35
ATOM   1230  CA   GLN  173   -33.883  23.428  47.962  1.00   5.17
ATOM   1231  C    GLN  173   -34.741  24.402  47.187  1.00   6.61
ATOM   1232  O    GLN  173   -34.469  24.693  45.967  1.00   7.86
ATOM   1233  N    GLU  174   -35.814  24.921  47.782  1.00   6.75
ATOM   1234  OE2  GLU  174   -40.122  25.837  46.396  1.00   8.25
ATOM   1235  OE1  GLU  174   -40.521  23.919  47.243  1.00  10.88
ATOM   1236  CD   GLU  174   -39.899  24.969  47.265  1.00  10.25
ATOM   1237  CG   GLU  174   -38.863  25.164  48.362  1.00   8.85
ATOM   1238  CB   GLU  174   -37.861  26.313  48.083  1.00   9.36
ATOM   1239  CA   GLU  174   -36.686  25.892  47.108  1.00   7.86
ATOM   1240  C    GLU  174   -35.933  27.178  46.774  1.00   8.69
ATOM   1241  O    GLU  174   -35.082  27.712  47.515  1.00   9.98
ATOM   1242  N    VAL  175   -36.198  27.769  45.591  1.00   8.61
ATOM   1243  CG2  VAL  175   -34.568  29.950  43.032  1.00  11.90
ATOM   1244  CG1  VAL  175   -36.989  29.512  42.968  1.00  13.78
ATOM   1245  CB   VAL  175   -35.652  29.062  43.589  1.00  13.52
ATOM   1246  CA   VAL  175   -35.605  29.022  45.144  1.00   8.03
ATOM   1247  C    VAL  175   -36.196  30.221  45.869  1.00   8.45
ATOM   1248  O    VAL  175   -35.453  31.199  46.161  1.00   8.96
ATOM   1249  N    THR  176   -37.454  30.220  46.297  1.00   9.06
ATOM   1250  CG2  THR  176   -40.371  32.282  47.869  1.00  18.26
ATOM   1251  OG1  THR  176   -40.343  30.692  46.091  1.00  18.82
ATOM   1252  CB   THR  176   -39.648  31.030  47.350  1.00  15.35
ATOM   1253  CA   THR  176   -38.133  31.355  46.965  1.00  10.08
ATOM   1254  C    THR  176   -37.370  32.053  48.082  1.00  12.75
ATOM   1255  O    THR  176   -37.203  33.295  48.105  1.00  12.78
ATOM   1256  N    PRO  177   -36.827  31.275  49.019  1.00  13.60
ATOM   1257  CA   PRO  177   -36.059  31.831  50.137  1.00  14.56
ATOM   1258  C    PRO  177   -34.832  32.550  49.634  1.00  14.53
ATOM   1259  O    PRO  177   -34.405  33.537  50.205  1.00  14.33
```

```
ATOM   1260  CB   PRO  177    -35.684  30.599  50.967  1.00  15.59
ATOM   1261  CG   PRO  177    -36.607  29.488  50.587  1.00  15.55
ATOM   1262  CD   PRO  177    -37.028  29.818  49.155  1.00  14.17
ATOM   1263  N    MET  178    -34.177  32.085  48.557  1.00  11.26
ATOM   1264  CE   MET  178    -31.755  28.533  46.007  1.00  19.72
ATOM   1265  SD   MET  178    -30.708  29.927  46.237  1.00  22.73
ATOM   1266  CG   MET  178    -31.639  30.737  47.651  1.00  17.28
ATOM   1267  CB   MET  178    -32.343  31.919  46.980  1.00   9.92
ATOM   1268  CA   MET  178    -32.991  32.789  48.077  1.00  11.19
ATOM   1269  C    MET  178    -33.372  34.163  47.572  1.00  14.99
ATOM   1270  O    MET  178    -32.631  35.161  47.724  1.00  16.24
ATOM   1271  N    VAL  179    -34.492  34.273  46.870  1.00  12.66
ATOM   1272  CG2  VAL  179    -35.871  34.516  44.214  1.00  11.56
ATOM   1273  CG1  VAL  179    -36.995  36.540  45.154  1.00  16.31
ATOM   1274  CB   VAL  179    -36.242  35.254  45.495  1.00  14.06
ATOM   1275  CA   VAL  179    -34.973  35.549  46.347  1.00  14.10
ATOM   1276  C    VAL  179    -35.411  36.462  47.516  1.00  17.87
ATOM   1277  O    VAL  179    -35.152  37.674  47.535  1.00  18.01
ATOM   1278  N    ASN  180    -36.139  35.872  48.451  1.00  17.87
ATOM   1279  ND2  ASN  180    -39.996  35.004  49.792  1.00  34.66
ATOM   1280  OD1  ASN  180    -39.173  36.590  48.442  1.00  26.20
ATOM   1281  CG   ASN  180    -39.030  35.860  49.435  1.00  27.22
ATOM   1282  CB   ASN  180    -37.798  35.850  50.334  1.00  22.46
ATOM   1283  CA   ASN  180    -36.683  36.628  49.576  1.00  21.81
ATOM   1284  C    ASN  180    -35.663  37.122  50.588  1.00  22.21
ATOM   1285  O    ASN  180    -35.786  38.276  51.007  1.00  25.30
ATOM   1286  N    SER  181    -34.775  36.258  50.952  1.00  20.13
ATOM   1287  OG   SER  181    -34.362  34.891  53.477  1.00  46.23
ATOM   1288  CB   SER  181    -33.268  35.230  52.620  1.00  29.26
ATOM   1289  CA   SER  181    -33.740  36.530  51.921  1.00  20.62
ATOM   1290  C    SER  181    -32.474  37.109  51.355  1.00  20.10
ATOM   1291  O    SER  181    -31.914  37.915  52.104  1.00  20.08
ATOM   1292  N    TRP  182    -32.042  36.665  50.186  1.00  17.06
ATOM   1293  CD2  TRP  182    -28.744  33.771  49.582  1.00  20.91
ATOM   1294  CE3  TRP  182    -28.470  33.240  48.331  1.00  15.11
ATOM   1295  CZ3  TRP  182    -27.853  31.999  48.269  1.00  15.36
ATOM   1296  CH2  TRP  182    -27.529  31.313  49.436  1.00  15.65
ATOM   1297  CZ2  TRP  182    -27.769  31.806  50.713  1.00  19.64
ATOM   1298  CE2  TRP  182    -28.381  33.057  50.742  1.00  24.59
ATOM   1299  NE1  TRP  182    -28.738  33.820  51.828  1.00  27.77
ATOM   1300  CD1  TRP  182    -29.323  34.986  51.373  1.00  29.42
ATOM   1301  CG   TRP  182    -29.377  35.009  50.004  1.00  22.91
ATOM   1302  CB   TRP  182    -29.884  36.098  49.127  1.00  20.07
ATOM   1303  CA   TRP  182    -30.771  37.210  49.681  1.00  14.46
ATOM   1304  C    TRP  182    -30.992  38.306  48.680  1.00  14.45
ATOM   1305  O    TRP  182    -30.007  38.974  48.321  1.00  16.23
ATOM   1306  N    GLY  183    -32.203  38.445  48.182  1.00  13.61
ATOM   1307  CA   GLY  183    -32.431  39.519  47.179  1.00  13.59
ATOM   1308  C    GLY  183    -31.864  39.105  45.800  1.00  12.98
ATOM   1309  O    GLY  183    -31.478  40.015  45.005  1.00  11.51
ATOM   1310  N    VAL  184    -31.805  37.788  45.559  1.00  12.12
ATOM   1311  CG2  VAL  184    -31.741  34.892  44.375  1.00  20.41
ATOM   1312  CG1  VAL  184    -29.458  35.739  44.931  1.00  20.83
ATOM   1313  CB   VAL  184    -30.729  35.966  44.088  1.00  14.52
```

| ATOM | 1314 | CA | VAL | 184 | -31.288 | 37.397 | 44.216 | 1.00 | 13.35 |
|---|---|---|---|---|---|---|---|---|---|
| ATOM | 1315 | C | VAL | 184 | -32.431 | 37.647 | 43.201 | 1.00 | 13.39 |
| ATOM | 1316 | O | VAL | 184 | -33.619 | 37.490 | 43.538 | 1.00 | 13.79 |
| ATOM | 1317 | N | ARG | 185 | -32.041 | 37.991 | 41.974 | 1.00 | 11.85 |
| ATOM | 1318 | NH2 | ARG | 185 | -31.382 | 44.754 | 43.270 | 1.00 | 30.49 |
| ATOM | 1319 | NH1 | ARG | 185 | -30.633 | 44.370 | 41.110 | 1.00 | 29.76 |
| ATOM | 1320 | CZ | ARG | 185 | -31.320 | 43.982 | 42.177 | 1.00 | 30.81 |
| ATOM | 1321 | NE | ARG | 185 | -31.986 | 42.816 | 42.217 | 1.00 | 27.27 |
| ATOM | 1322 | CD | ARG | 185 | -31.978 | 41.937 | 41.036 | 1.00 | 23.48 |
| ATOM | 1323 | CG | ARG | 185 | -32.959 | 40.840 | 41.410 | 1.00 | 19.17 |
| ATOM | 1324 | CB | ARG | 185 | -32.789 | 39.732 | 40.349 | 1.00 | 14.23 |
| ATOM | 1325 | CA | ARG | 185 | -32.980 | 38.274 | 40.869 | 1.00 | 11.15 |
| ATOM | 1326 | C | ARG | 185 | -32.746 | 37.319 | 39.703 | 1.00 | 8.87 |
| ATOM | 1327 | O | ARG | 185 | -31.721 | 37.472 | 39.065 | 1.00 | 8.01 |
| ATOM | 1328 | N | LEU | 186 | -33.644 | 36.370 | 39.444 | 1.00 | 9.17 |
| ATOM | 1329 | CA | LEU | 186 | -33.463 | 35.447 | 38.328 | 1.00 | 9.78 |
| ATOM | 1330 | C | LEU | 186 | -33.503 | 36.225 | 36.995 | 1.00 | 10.75 |
| ATOM | 1331 | O | LEU | 186 | -34.316 | 37.132 | 36.787 | 1.00 | 10.04 |
| ATOM | 1332 | CB | LEU | 186 | -34.648 | 34.435 | 38.305 | 1.00 | 8.11 |
| ATOM | 1333 | CG | LEU | 186 | -34.760 | 33.549 | 39.546 | 1.00 | 16.49 |
| ATOM | 1334 | CD1 | LEU | 186 | -35.699 | 32.375 | 39.276 | 1.00 | 14.66 |
| ATOM | 1335 | CD2 | LEU | 186 | -33.400 | 32.928 | 39.887 | 1.00 | 16.56 |
| ATOM | 1336 | N | ARG | 187 | -32.652 | 35.750 | 36.102 | 1.00 | 7.79 |
| ATOM | 1337 | NH2 | ARG | 187 | -30.740 | 39.908 | 29.630 | 1.00 | 46.94 |
| ATOM | 1338 | NH1 | ARG | 187 | -29.232 | 39.169 | 31.188 | 1.00 | 49.29 |
| ATOM | 1339 | CZ | ARG | 187 | -30.477 | 39.174 | 30.718 | 1.00 | 44.29 |
| ATOM | 1340 | NE | ARG | 187 | -31.443 | 38.474 | 31.338 | 1.00 | 36.97 |
| ATOM | 1341 | CD | ARG | 187 | -31.199 | 37.750 | 32.536 | 1.00 | 28.81 |
| ATOM | 1342 | CG | ARG | 187 | -31.219 | 36.300 | 32.604 | 1.00 | 27.43 |
| ATOM | 1343 | CB | ARG | 187 | -31.340 | 35.889 | 34.068 | 1.00 | 12.14 |
| ATOM | 1344 | CA | ARG | 187 | -32.653 | 36.298 | 34.718 | 1.00 | 9.41 |
| ATOM | 1345 | C | ARG | 187 | -33.901 | 35.672 | 34.023 | 1.00 | 10.55 |
| ATOM | 1346 | O | ARG | 187 | -34.139 | 34.427 | 33.990 | 1.00 | 10.23 |
| ATOM | 1347 | N | THR | 188 | -34.769 | 36.530 | 33.478 | 1.00 | 9.32 |
| ATOM | 1348 | CA | THR | 188 | -35.996 | 36.175 | 32.723 | 1.00 | 10.52 |
| ATOM | 1349 | C | THR | 188 | -35.889 | 36.694 | 31.263 | 1.00 | 11.51 |
| ATOM | 1350 | O | THR | 188 | -34.786 | 37.058 | 30.810 | 1.00 | 10.45 |
| ATOM | 1351 | CB | THR | 188 | -37.361 | 36.593 | 33.422 | 1.00 | 7.88 |
| ATOM | 1352 | OG1 | THR | 188 | -37.427 | 38.057 | 33.443 | 1.00 | 7.10 |
| ATOM | 1353 | CG2 | THR | 188 | -37.581 | 36.118 | 34.850 | 1.00 | 8.10 |
| ATOM | 1354 | OXT | THR | 188 | -36.851 | 36.451 | 30.513 | 1.00 | 13.52 |

```
                          SEQUENCE LISTING

<160> NUMBER OF SEQ ID NOS: 21

<210> SEQ ID NO 1
<211> LENGTH: 1596
<212> TYPE: DNA
<213> ORGANISM: Nocardiopsis sp. NRRL 18262 ("Protease 10")
<220> FEATURE:
<221> NAME/KEY: CDS
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 1
acgtttggta cgggtaccgg tgtccgcatg tggccagaat gccccttgc gacagggaac        60 ggattcggtc ggtagcgcat cgactccgac aaccgcgagg tggccgttcg cgtcgccacg      120
ttctgcgacc gtcatgcgac ccatcatcgg gtgaccccac cgagctctga atggtccacc      180
gttctgacgg tctttccctc accaaaacgt gcacctatgt ttaggacgtt gtttaccgaa      240
tgtctcggtg aacgacaggg gccggacggt attcggcccc gatccccgt tgatccccc       300 aggagagtag ggacccc atg cga ccc tcc ccc gtt gtc tcc gcc atc  ggt       350
                   Met Arg Pro Ser Pro Val Val Ser Ala Ile  Gly
                                 -190                 -185 acg gga gcg ctg  gcc ttc ggt ctg gcg  ctg tcc ggt acc ccg  ggt        395
Thr Gly Ala Leu  Ala Phe Gly Leu Ala  Leu Ser Gly Thr Pro  Gly
             -180                 -175                 -170 gcc ctc gcg gcc  acc gga gcg ctc ccc  cag tca ccc acc ccg  gag        440
Ala Leu Ala Ala  Thr Gly Ala Leu Pro  Gln Ser Pro Thr Pro  Glu
             -165                 -160                 -155 gcc gac gcg gtc  tcc atg cag gag gcg  ctc cag cgc gac ctc  gac        485
Ala Asp Ala Val  Ser Met Gln Glu Ala  Leu Gln Arg Asp Leu  Asp
             -150                 -145                 -140 ctg acc tcc gcc  gag gcc gag gag ctg  ctg gcc gcc cag gac  acc        530
Leu Thr Ser Ala  Glu Ala Glu Glu Leu  Leu Ala Ala Gln Asp  Thr
             -135                 -130                 -125 gcc ttc gag gtc  gac gag gcc gcg gcc  gag gcc gcc ggg gac  gcc        575
Ala Phe Glu Val  Asp Glu Ala Ala Ala  Glu Ala Ala Gly Asp  Ala
             -120                 -115                 -110 tac ggc ggc tcc  gtc ttc gac acc gag  agc ctg gaa ctg acc gtc ctg     623
Tyr Gly Gly Ser  Val Phe Asp Thr Glu  Ser Leu Glu Leu Thr Val Leu
             -105                 -100                  -95 gtc acc gat gcc  gcc gcg gtc gag gcc  gtg gag gcc acc ggc gcc ggg     671
Val Thr Asp Ala  Ala Ala Val Glu Ala  Val Glu Ala Thr Gly Ala Gly
              -90                  -85                  -80 acc gag ctg gtc  tcc tac ggc atc gac  ggt ctc gac gag atc gtc cag     719
Thr Glu Leu Val  Ser Tyr Gly Ile Asp  Gly Leu Asp Glu Ile Val Gln
               -75                  -70                  -65 gag ctc aac gcc  gcc gac gcc gtt ccc  ggt gtg gtc ggc tgg tac ccg     767
Glu Leu Asn Ala  Ala Asp Ala Val Pro  Gly Val Val Gly Trp Tyr Pro
```

|  |  |
|---|---|
| gac gtg gcg ggt gac acc gtc gtc ctg gag gtc ctg gag ggt tcc gga<br>Asp Val Ala Gly Asp Thr Val Val Leu Glu Val Leu Glu Gly Ser Gly<br>            -40                           -35                        -30 | 815 |
| gcc gac gtc agc ggc ctg ctc gcg gac gcc ggc gtg gac gcc tcg gcc<br>Ala Asp Val Ser Gly Leu Leu Ala Asp Ala Gly Val Asp Ala Ser Ala<br>           -25                          -20                         -15 | 863 |
| gtc gag gtg acc acg agc gac cag ccc gag ctc tac gcc gac atc atc<br>Val Glu Val Thr Thr Ser Asp Gln Pro Glu Leu Tyr Ala Asp Ile Ile<br>     -10                       -5                           -1  1 | 911 |
| ggt ggt ctg gcc tac acc atg ggc ggc cgc tgt tcg gtc ggc ttc gcg<br>Gly Gly Leu Ala Tyr Thr Met Gly Gly Arg Cys Ser Val Gly Phe Ala<br>5                     10                       15                    20 | 959 |
| gcc acc aac gcc gcc ggt cag ccc ggg ttc gtc acc gcc ggt cac tgc<br>Ala Thr Asn Ala Ala Gly Gln Pro Gly Phe Val Thr Ala Gly His Cys<br>               25                     30                     35 | 1007 |
| ggc cgc gtg ggc acc cag gtg acc atc ggc aac ggc agg ggc gtc ttc<br>Gly Arg Val Gly Thr Gln Val Thr Ile Gly Asn Gly Arg Gly Val Phe<br>        40                          45                       50 | 1055 |
| gag cag tcc gtc ttc ccc ggc aac gac gcg gcc ttc gtc cgc ggt acg<br>Glu Gln Ser Val Phe Pro Gly Asn Asp Ala Ala Phe Val Arg Gly Thr<br>     55                       60                       65 | 1103 |
| tcc aac ttc acg ctg acc aac ctg gtc agc cgc tac aac acc ggc ggg<br>Ser Asn Phe Thr Leu Thr Asn Leu Val Ser Arg Tyr Asn Thr Gly Gly<br>    70                       75                     80 | 1151 |
| tac gcc acg gtc gcc ggt cac aac cag gcc ccc atc ggc tcc tcc gtc<br>Tyr Ala Thr Val Ala Gly His Asn Gln Ala Pro Ile Gly Ser Ser Val<br>85                     90                       95                   100 | 1199 |
| tgc cgc tcc ggc tcc acc acc ggt tgg cac tgc ggc acc atc cag gcc<br>Cys Arg Ser Gly Ser Thr Thr Gly Trp His Cys Gly Thr Ile Gln Ala<br>            105                     110                     115 | 1247 |
| cgc ggc cag tcg gtg agc tac ccc gag ggc acc gtc acc aac atg acc<br>Arg Gly Gln Ser Val Ser Tyr Pro Glu Gly Thr Val Thr Asn Met Thr<br>        120                         125                     130 | 1295 |
| cgg acc acc gtg tgc gcc gag ccc ggc gac tcc ggc ggc tcc tac atc<br>Arg Thr Thr Val Cys Ala Glu Pro Gly Asp Ser Gly Gly Ser Tyr Ile<br>         135                        140                     145 | 1343 |
| tcc ggc acc cag gcc cag ggc gtg acc tcc ggc ggc tcc ggc aac tgc<br>Ser Gly Thr Gln Ala Gln Gly Val Thr Ser Gly Gly Ser Gly Asn Cys<br>    150                      155                     160 | 1391 |
| cgc acc ggg acc acc ttc tac cag gag gtc acc ccc atg gtg aac<br>Arg Thr Gly Gly Thr Thr Phe Tyr Gln Glu Val Thr Pro Met Val Asn<br>165                   170                     175                180 | 1439 |
| tcc tgg ggc gtc cgt ctc cgg acc tgatccccgc ggttccaggc ggaccgacgg<br>Ser Trp Gly Val Arg Leu Arg Thr<br>               185 | 1493 |
| tcgtgacctg agtaccaggc gtccccgccg cttccagcgg cgtccgcacc ggggtgggac | 1553 |
| cgggcgtggc cacggcccca cccgtgaccg gaccgcccgg cta | 1596 |

<210> SEQ ID NO 2
<211> LENGTH: 382
<212> TYPE: PRT
<213> ORGANISM: Nocardiopsis sp. NRRL 18262 ("Protease 10")

<400> SEQUENCE: 2

Met Arg Pro Ser Pro  Val Val Ser Ala Ile  Gly Thr Gly Ala Leu
                -190                       -185                      -180

Ala Phe Gly Leu Ala  Leu Ser Gly Thr Pro  Gly Ala Leu Ala Ala
        -175                    -170                    -165

```
Thr Gly Ala Leu Pro   Gln Ser Pro Thr   Pro  Glu Ala Asp Ala Val
              -160                -155                     -150

Ser Met Gln Glu Ala   Leu Gln Arg Asp   Leu  Asp Leu Thr Ser Ala
              -145                -140                     -135

Glu Ala Glu Glu Leu   Leu Ala Ala Gln Asp    Thr Ala Phe Glu Val
              -130                -125                     -120

Asp Glu Ala Ala Ala   Glu Ala Ala Gly Asp    Ala Tyr Gly Gly Ser
              -115                -110                     -105

Val Phe Asp Thr Glu   Ser Leu Glu Leu   Thr  Val Leu Val Thr Asp Ala
              -100                -95                      -90

Ala Ala Val Glu Ala   Val Glu Ala Thr   Gly  Ala Gly Thr Glu Leu Val
               -85                 -80                      -75

Ser Tyr Gly Ile Asp   Gly Leu Asp Glu   Ile  Val Gln Glu Leu Asn Ala
               -70                 -65                      -60

Ala Asp Ala Val Pro   Gly Val Val Gly   Trp  Tyr Pro Asp Val Ala Gly
               -55                 -50                      -45

Asp Thr Val Val Leu   Glu Val Leu Glu   Gly  Ser Gly Ala Asp Val Ser
-40                    -35                 -30                      -25

Gly Leu Leu Ala Asp   Ala Gly Val Asp   Ala  Ser Ala Val Glu Val Thr
               -20                 -15                      -10

Thr Ser Asp Gln Pro   Glu Leu Tyr Ala   Asp  Ile Ile Gly Gly Leu Ala
                -5                  -1   1                     5

Tyr Thr Met Gly Gly   Arg Cys Ser Val   Gly  Phe Ala Ala Thr Asn Ala
                10                  15                      20

Ala Gly Gln Pro Gly   Phe Val Thr Ala   Gly  His Cys Gly Arg Val Gly
25                     30                  35                       40

Thr Gln Val Thr Ile   Gly Asn Gly Arg   Gly  Val Phe Glu Gln Ser Val
                45                  50                      55

Phe Pro Gly Asn Asp   Ala Ala Phe Val   Arg  Gly Thr Ser Asn Phe Thr
                60                  65                      70

Leu Thr Asn Leu Val   Ser Arg Tyr Asn   Thr  Gly Gly Tyr Ala Thr Val
                75                  80                      85

Ala Gly His Asn Gln   Ala Pro Ile Gly   Ser  Ser Val Cys Arg Ser Gly
                90                  95                     100

Ser Thr Thr Gly Trp   His Cys Gly Thr   Ile  Gln Ala Arg Gly Gln Ser
105                   110                 115                      120

Val Ser Tyr Pro Glu   Gly Thr Val Thr   Asn  Met Thr Arg Thr Thr Val
               125                  130                     135

Cys Ala Glu Pro Gly   Asp Ser Gly Gly   Ser  Tyr Ile Ser Gly Thr Gln
               140                  145                     150

Ala Gln Gly Val Thr   Ser Gly Gly Ser   Gly  Asn Cys Arg Thr Gly Gly
               155                  160                     165

Thr Thr Phe Tyr Gln   Glu Val Thr Pro   Met  Val Asn Ser Trp Gly Val
               170                  175                     180

Arg Leu Arg Thr
185

<210> SEQ ID NO 3
<211> LENGTH: 1065
<212> TYPE: DNA
<213> ORGANISM: Nocardiopsis dassonvillei subspecies dassonvillei DSM
      43235 ("Protease 18")
<220> FEATURE:
<221> NAME/KEY: CDS
<222> LOCATION: (1)..(1062)
```

-continued

```
<220> FEATURE:
<221> NAME/KEY: mat_peptide
<222> LOCATION: (499)..(1062)

<400> SEQUENCE: 3 gct ccg gcc ccc gtc ccc cag  acc ccc gtc gcc gac  gac agc gcc          45
Ala Pro Ala Pro Val Pro Gln  Thr Pro Val Ala Asp  Asp Ser Ala
    -165             -160                  -155 gcc agc atg acc gag gcg ctc  aag cgc gac ctc gac  ctc acc tcg          90
Ala Ser Met Thr Glu Ala Leu  Lys Arg Asp Leu Asp  Leu Thr Ser
    -150             -145                  -140 gcc gag gcc gag gag ctt ctc  tcg gcg cag gaa gcc  gcc atc gag         135
Ala Glu Ala Glu Glu Leu Leu  Ser Ala Gln Glu Ala  Ala Ile Glu
    -135             -130                  -125 acc gac gcc gag gcc acc gag  gcc gcg ggc gag gcc  tac ggc ggc         180
Thr Asp Ala Glu Ala Thr Glu  Ala Ala Gly Glu Ala  Tyr Gly Gly
    -120             -115                  -110 tca ctg ttc gac acc gag acc  ctc gaa ctc acc gtg  ctg gtc acc gac     228
Ser Leu Phe Asp Thr Glu Thr  Leu Glu Leu Thr Val  Leu Val Thr Asp
    -105             -100                  -95 gcc tcc gcc gtc gag gcg gtc  gag gcc acc gga gcc  cag gcc acc gtc     276
Ala Ser Ala Val Glu Ala Val  Glu Ala Thr Gly Ala  Gln Ala Thr Val
-90             -85                  -80                  -75 gtc tcc cac ggc acc gag ggc  ctg acc gag gtc gtg  gag gac ctc aac     324
Val Ser His Gly Thr Glu Gly  Leu Thr Glu Val Val  Glu Asp Leu Asn
            -70                  -65                  -60 ggc gcc gag gtt ccc gag agc  gtc ctc ggc tgg tac  ccg gac gtg gag     372
Gly Ala Glu Val Pro Glu Ser  Val Leu Gly Trp Tyr  Pro Asp Val Glu
            -55                  -50                  -45 agc gac acc gtc gtg gtc gag  gtg ctg gag ggc tcc  gac gcc gac gtc     420
Ser Asp Thr Val Val Val Glu  Val Leu Glu Gly Ser  Asp Ala Asp Val
        -40                  -35                  -30 gcc gcc ctg ctc gcc gac gcc  ggt gtg gac tcc tcg  gtc cgg gtg         468
Ala Ala Leu Leu Ala Asp Ala  Gly Val Asp Ser Ser  Val Arg Val
        -25                  -20                  -15 gag gag gcc gag gag gcc ccg  cag gtc tac gcc gac  atc atc ggc ggc     516
Glu Glu Ala Glu Glu Ala Pro  Gln Val Tyr Ala Asp  Ile Ile Gly Gly
-10                   -5                  -1  1                  5 ctg gcc tac tac atg ggc ggc  cgc tgc tcc gtc ggc  ttc gcc gcg acc     564
Leu Ala Tyr Tyr Met Gly Gly  Arg Cys Ser Val Gly  Phe Ala Ala Thr
            10                   15                  20 aac agc gcc ggt cag ccc ggt  ttc gtc acc gcc ggc  cac tgc ggc acc     612
Asn Ser Ala Gly Gln Pro Gly  Phe Val Thr Ala Gly  His Cys Gly Thr
            25                   30                  35 gtc ggc acc ggc gtg acc atc  ggc aac ggc acc ggc  acc ttc cag aac     660
Val Gly Thr Gly Val Thr Ile  Gly Asn Gly Thr Gly  Thr Phe Gln Asn
            40                   45                  50 tcg gtc ttc ccc ggc aac gac  gcc gcc ttc gtc cgc  ggc acc tcc aac     708
Ser Val Phe Pro Gly Asn Asp  Ala Ala Phe Val Arg  Gly Thr Ser Asn
55                   60                   65                  70 ttc acc ctg acc aac ctg gtc  tcg cgc tac aac tcg  ggc ggc tac cag     756
Phe Thr Leu Thr Asn Leu Val  Ser Arg Tyr Asn Ser  Gly Gly Tyr Gln
            75                   80                  85 tcg gtg acc ggt acc agc cag  gcc ccg gcc ggc tcg  gcc gtg tgc cgc     804
Ser Val Thr Gly Thr Ser Gln  Ala Pro Ala Gly Ser  Ala Val Cys Arg
            90                   95                  100 tcc ggc tcc acc acc ggc tgg  cac tgc ggc acc atc  cag gcc cgc aac     852
Ser Gly Ser Thr Thr Gly Trp  His Cys Gly Thr Ile  Gln Ala Arg Asn
            105                  110                 115 cag acc gtg cgc tac ccg cag  ggc acc gtc tac tcg  ctc acc cgc acc     900
```

```
                                                  -continued

Gln Thr Val Arg Tyr Pro Gln Gly Thr Val Tyr Ser Leu Thr Arg Thr
    120                 125                 130 aac gtg tgc gcc gag ccc ggc gac tcc ggc ggt tcg ttc atc tcc ggc      948
Asn Val Cys Ala Glu Pro Gly Asp Ser Gly Gly Ser Phe Ile Ser Gly
135                 140                 145                 150 tcg cag gcc cag ggc gtc acc tcc ggc ggc tcc ggc aac tgc tcc gtc      996
Ser Gln Ala Gln Gly Val Thr Ser Gly Gly Ser Gly Asn Cys Ser Val
                155                 160                 165 ggc ggc acg acc tac tac cag gag gtc acc ccg atg atc aac tcc tgg     1044
Gly Gly Thr Thr Tyr Tyr Gln Glu Val Thr Pro Met Ile Asn Ser Trp
        170                 175                 180 ggt gtc agg atc cgg acc taa                                         1065
Gly Val Arg Ile Arg Thr
        185

<210> SEQ ID NO 4
<211> LENGTH: 354
<212> TYPE: PRT
<213> ORGANISM: Nocardiopsis dassonvillei subspecies dassonvillei DSM
      43235 ("Protease 18")

<400> SEQUENCE: 4

Ala Pro  Ala Pro Val Pro Gln  Thr Pro Val Ala Asp  Asp Ser Ala
    -165              -160                 -155

Ala Ser  Met Thr Glu Ala Leu  Lys Arg Asp Leu Asp  Leu Thr Ser
    -150              -145                 -140

Ala Glu  Ala Glu Glu Leu Leu  Ser Ala Gln Glu Ala  Ala Ile Glu
    -135              -130                 -125

Thr Asp  Ala Glu Ala Thr Glu  Ala Ala Gly Glu Ala  Tyr Gly Gly
    -120              -115                 -110

Ser Leu  Phe Asp Thr Glu Thr  Leu Glu Leu Thr Val  Leu Val Thr Asp
    -105              -100                  -95

Ala Ser Ala Val Glu Ala Val Glu Ala Thr Gly Ala Gln Ala Thr Val
-90             -85              -80                  -75

Val Ser His Gly Thr Glu Gly Leu Thr Glu Val Val Glu Asp Leu Asn
                -70              -65                  -60

Gly Ala Glu Val Pro Glu Ser Val Leu Gly Trp Tyr Pro Asp Val Glu
            -55              -50                  -45

Ser Asp Thr Val Val Val Glu Val Leu Glu Gly Ser Asp Ala Asp Val
        -40              -35                  -30

Ala Ala Leu Leu Ala Asp Ala Gly Val Asp Ser Ser Val Arg Val
    -25              -20                  -15

Glu Glu Ala Glu Glu Ala Pro Gln Val Tyr Ala Asp Ile Ile Gly Gly
-10              -5                   -1  1                5

Leu Ala Tyr Tyr Met Gly Gly Arg Cys Ser Val Gly Phe Ala Ala Thr
                10                  15                  20

Asn Ser Ala Gly Gln Pro Gly Phe Val Thr Ala Gly His Cys Gly Thr
                25                  30                  35

Val Gly Thr Gly Val Thr Ile Gly Asn Gly Thr Gly Thr Phe Gln Asn
        40                  45                  50

Ser Val Phe Pro Gly Asn Asp Ala Ala Phe Val Arg Gly Thr Ser Asn
55                  60                  65                  70

Phe Thr Leu Thr Asn Leu Val Ser Arg Tyr Asn Ser Gly Gly Tyr Gln
                75                  80                  85

Ser Val Thr Gly Thr Ser Gln Ala Pro Ala Gly Ser Ala Val Cys Arg
            90                  95                  100
```

```
Ser Gly Ser Thr Thr Gly Trp His Cys Gly Thr Ile Gln Ala Arg Asn
        105                 110                 115

Gln Thr Val Arg Tyr Pro Gln Gly Thr Val Tyr Ser Leu Thr Arg Thr
    120                 125                 130

Asn Val Cys Ala Glu Pro Gly Asp Ser Gly Gly Ser Phe Ile Ser Gly
135                 140                 145                 150

Ser Gln Ala Gln Gly Val Thr Ser Gly Gly Ser Gly Asn Cys Ser Val
            155                 160                 165

Gly Gly Thr Thr Tyr Tyr Gln Glu Val Thr Pro Met Ile Asn Ser Trp
        170                 175                 180

Gly Val Arg Ile Arg Thr
        185

<210> SEQ ID NO 5
<211> LENGTH: 1062
<212> TYPE: DNA
<213> ORGANISM: Nocardiopsis prasina DSM 15648 ("Protease 11")
<220> FEATURE:
<221> NAME/KEY: CDS
<222> LOCATION: (1)..(1059)
<220> FEATURE:
<221> NAME/KEY: mat_peptide
<222> LOCATION: (496)..(1059)

<400> SEQUENCE: 5 gcc acc gga ccg ctc ccc cag tca ccc acc ccg gag gcc gac gcc        45
Ala Thr Gly Pro Leu Pro Gln Ser Pro Thr Pro Glu Ala Asp Ala
-165                -160                -155 gtc tcc atg cag gag gcg ctc cag cgc gac ctc ggc ctg acc ccg        90
Val Ser Met Gln Glu Ala Leu Gln Arg Asp Leu Gly Leu Thr Pro
-150                -145                -140 ctt gag gcc gat gaa ctg ctg gcc gcc cag gac  acc gcc ttc gag      135
Leu Glu Ala Asp Glu Leu Leu Ala Ala Gln Asp  Thr Ala Phe Glu
-135                -130                -125 gtc gac gag gcc gcg gcc gcg gcc gcc ggg gac  gcc tac ggc ggc      180
Val Asp Glu Ala Ala Ala Ala Ala Ala Gly Asp  Ala Tyr Gly Gly
-120                -115                -110 tcc gtc ttc gac acc gag  acc ctg gaa ctg acc gtc ctg gtc acc gac  228
Ser Val Phe Asp Thr Glu  Thr Leu Glu Leu Thr Val Leu Val Thr Asp
-105                -100                 -95                 -90 gcc gcc tcg gtc gag gct gtg gag gcc acc ggc gcg ggt acc gaa ctc  276
Ala Ala Ser Val Glu Ala Val Glu Ala Thr Gly Ala Gly Thr Glu Leu
                -85                 -80                 -75 gtc tcc tac ggc atc gag ggc ctc gac gag atc atc cag gat ctc aac  324
Val Ser Tyr Gly Ile Glu Gly Leu Asp Glu Ile Ile Gln Asp Leu Asn
            -70                 -65                 -60 gcc gcc gac gcc gtc ccc ggc gtg gtc ggc tgg tac ccg gac gtg gcg  372
Ala Ala Asp Ala Val Pro Gly Val Val Gly Trp Tyr Pro Asp Val Ala
        -55                 -50                 -45 ggt gac acc gtc gtc ctg gag gtc ctg gag ggt tcc gga gcc gac gtg  420
Gly Asp Thr Val Val Leu Glu Val Leu Glu Gly Ser Gly Ala Asp Val
    -40                 -35                 -30 agc ggc ctg ctc gcc gac gcc ggc gtg gac gcc tcg gcc gtc gag gtg  468
Ser Gly Leu Leu Ala Asp Ala Gly Val Asp Ala Ser Ala Val Glu Val
-25                 -20                 -15                 -10 acc agc agt gcg cag ccc gag ctc tac gcc gac atc atc ggc ggt ctg  516
Thr Ser Ser Ala Gln Pro Glu Leu Tyr Ala Asp Ile Ile Gly Gly Leu
                 -5                 -1  1                  5 gcc tac acc atg ggc ggc cgc tgt tcg gtc gga ttc gcg gcc acc aac  564
Ala Tyr Thr Met Gly Gly Arg Cys Ser Val Gly Phe Ala Ala Thr Asn
            10                  15                  20
```

-continued

```
gcc gcc ggt cag ccc gga ttc gtc acc gcc ggt cac tgt ggc cgc gtg        612
Ala Ala Gly Gln Pro Gly Phe Val Thr Ala Gly His Cys Gly Arg Val
    25                  30                  35 ggc acc cag gtg agc atc ggc aac ggc cag ggc gtc ttc gag cag tcc        660
Gly Thr Gln Val Ser Ile Gly Asn Gly Gln Gly Val Phe Glu Gln Ser
 40                  45                  50                  55 atc ttc ccg ggc aac gac gcc gcc ttc gtc cgc ggc acg tcc aac ttc        708
Ile Phe Pro Gly Asn Asp Ala Ala Phe Val Arg Gly Thr Ser Asn Phe
                 60                  65                  70 acg ctg acc aac ctg gtc agc cgc tac aac acc ggc ggt tac gcc acc        756
Thr Leu Thr Asn Leu Val Ser Arg Tyr Asn Thr Gly Gly Tyr Ala Thr
     75                  80                  85 gtc gcc ggc cac aac cag gcg ccc atc ggc tcc tcc gtc tgc cgc tcc        804
Val Ala Gly His Asn Gln Ala Pro Ile Gly Ser Ser Val Cys Arg Ser
 90                  95                 100 ggc tcc acc acc ggc tgg cac tgc ggc acc atc cag gcc cgc ggc cag        852
Gly Ser Thr Thr Gly Trp His Cys Gly Thr Ile Gln Ala Arg Gly Gln
105                 110                 115 tcg gtg agc tac ccc gag ggc acc gtc acc aac atg acc cgg acc acc        900
Ser Val Ser Tyr Pro Glu Gly Thr Val Thr Asn Met Thr Arg Thr Thr
120                 125                 130                 135 gtg tgc gcc gag ccc ggc gac tcc ggc ggc tcc tac atc tcc ggc aac        948
Val Cys Ala Glu Pro Gly Asp Ser Gly Gly Ser Tyr Ile Ser Gly Asn
                140                 145                 150 cag gcc cag ggc gtc acc tcc ggc ggc tcc ggc aac tgc cgc acc ggc        996
Gln Ala Gln Gly Val Thr Ser Gly Gly Ser Gly Asn Cys Arg Thr Gly
                155                 160                 165 ggg acc acc ttc tac cag gag gtc acc ccc atg gtg aac tcc tgg ggc       1044
Gly Thr Thr Phe Tyr Gln Glu Val Thr Pro Met Val Asn Ser Trp Gly
                170                 175                 180 gtc cgt ctc cgg acc taa                                                1062
Val Arg Leu Arg Thr
    185
```

<210> SEQ ID NO 6
<211> LENGTH: 353
<212> TYPE: PRT
<213> ORGANISM: Nocardiopsis prasina DSM 15648 ("Protease 11")

<400> SEQUENCE: 6

```
Ala  Thr Gly Pro Leu Pro  Gln Ser Pro Thr Pro  Glu Ala Asp Ala
-165                 -160                 -155

Val  Ser Met Gln Glu Ala  Leu Gln Arg Asp Leu  Gly Leu Thr Pro
-150                 -145                 -140

Leu  Glu Ala Asp Glu Leu  Leu Ala Ala Gln Asp  Thr Ala Phe Glu
-135                 -130                 -125

Val  Asp Glu Ala Ala Ala  Ala Ala Ala Gly Asp  Ala Tyr Gly Gly
-120                 -115                 -110

Ser  Val Phe Asp Thr Glu  Thr Leu Glu Leu Thr  Val Leu Val Thr Asp
-105                 -100                  -95                  -90

Ala Ala Ser Val Glu Ala Val Glu Ala Thr Gly Ala Gly Thr Glu Leu
                -85                  -80                  -75

Val Ser Tyr Gly Ile Glu Gly Leu Asp Glu Ile Ile Gln Asp Leu Asn
            -70                  -65                  -60

Ala Ala Asp Ala Val Pro Gly Val Gly Trp Tyr Pro Asp Val Ala
        -55                  -50                  -45

Gly Asp Thr Val Val Leu Glu Val Leu Glu Gly Ser Gly Ala Asp Val
    -40                  -35                  -30
```

```
Ser Gly Leu Leu Ala Asp Ala Gly Val Asp Ala Ser Ala Val Glu Val
-25             -20                 -15                 -10

Thr Ser Ser Ala Gln Pro Glu Leu Tyr Ala Asp Ile Ile Gly Gly Leu
            -5              -1   1               5

Ala Tyr Thr Met Gly Gly Arg Cys Ser Val Gly Phe Ala Ala Thr Asn
        10              15              20

Ala Ala Gly Gln Pro Gly Phe Val Thr Ala Gly His Cys Gly Arg Val
    25              30              35

Gly Thr Gln Val Ser Ile Gly Asn Gly Gln Gly Val Phe Glu Gln Ser
40              45              50              55

Ile Phe Pro Gly Asn Asp Ala Ala Phe Val Arg Gly Thr Ser Asn Phe
            60              65              70

Thr Leu Thr Asn Leu Val Ser Arg Tyr Asn Thr Gly Gly Tyr Ala Thr
            75              80              85

Val Ala Gly His Asn Gln Ala Pro Ile Gly Ser Ser Val Cys Arg Ser
            90              95              100

Gly Ser Thr Thr Gly Trp His Cys Gly Thr Ile Gln Ala Arg Gly Gln
    105             110             115

Ser Val Ser Tyr Pro Glu Gly Thr Val Thr Asn Met Thr Arg Thr Thr
120             125             130             135

Val Cys Ala Glu Pro Gly Asp Ser Gly Gly Ser Tyr Ile Ser Gly Asn
                140             145             150

Gln Ala Gln Gly Val Thr Ser Gly Gly Ser Gly Asn Cys Arg Thr Gly
            155             160             165

Gly Thr Thr Phe Tyr Gln Glu Val Thr Pro Met Val Asn Ser Trp Gly
        170             175             180

Val Arg Leu Arg Thr
    185

<210> SEQ ID NO 7
<211> LENGTH: 1062
<212> TYPE: DNA
<213> ORGANISM: Nocardiopsis prasina DSM 15649 ("Protease 35")
<220> FEATURE:
<221> NAME/KEY: CDS
<222> LOCATION: (1)..(1059)
<220> FEATURE:
<221> NAME/KEY: mat_peptide
<222> LOCATION: (496)..(1059)

<400> SEQUENCE: 7 gcc acc gga cca ctc ccc cag tca ccc acc ccg gag gcc gac gcc        45
Ala Thr Gly Pro Leu Pro Gln Ser Pro Thr Pro Glu Ala Asp Ala
-165            -160                -155 gtc tcc atg cag gag gcg ctc cag cgc gac ctc ggc ctg acc ccg        90
Val Ser Met Gln Glu Ala Leu Gln Arg Asp Leu Gly Leu Thr Pro
-150            -145                -140 ctt gag gcc gat gaa ctg ctg gcc gcc cag gac acc gcc ttc gag       135
Leu Glu Ala Asp Glu Leu Leu Ala Ala Gln Asp Thr Ala Phe Glu
-135            -130                -125 gtc gac gag gcc gcg gcc gag gcc gcc ggt gac gcc tac ggc ggc       180
Val Asp Glu Ala Ala Ala Glu Ala Ala Gly Asp Ala Tyr Gly Gly
-120            -115                -110 tcc gtc ttc gac acc gag acc ctg gaa ctg acc gtc ctg gtc acc gac   228
Ser Val Phe Asp Thr Glu Thr Leu Glu Leu Thr Val Leu Val Thr Asp
-105            -100                -95                 -90 tcc gcc gcg gtc gag gcg gtg gag gcc acc ggc gcc ggg acc gaa ctg   276
Ser Ala Ala Val Glu Ala Val Glu Ala Thr Gly Ala Gly Thr Glu Leu
```

```
                  -85                 -80                 -75
gtc tcc tac ggc atc acg ggc ctc gac gag atc gtc gag gag ctc aac      324
Val Ser Tyr Gly Ile Thr Gly Leu Asp Glu Ile Val Glu Glu Leu Asn
            -70                 -65                 -60 gcc gcc gac gcc gtt ccc ggc gtg gtc ggc tgg tac ccg gac gtc gcg      372
Ala Ala Asp Ala Val Pro Gly Val Val Gly Trp Tyr Pro Asp Val Ala
        -55                 -50                 -45 ggt gac acc gtc gtg ctg gag gtc ctg gag ggt tcc ggc gcc gac gtg      420
Gly Asp Thr Val Val Leu Glu Val Leu Glu Gly Ser Gly Ala Asp Val
    -40                 -35                 -30 ggc ggc ctg ctc gcc gac gcc ggc gtg gac gcc tcg gcg gtc gag gtg      468
Gly Gly Leu Leu Ala Asp Ala Gly Val Asp Ala Ser Ala Val Glu Val
-25                 -20                 -15                 -10 acc acc acc gag cag ccc gag ctg tac gcc gac atc atc ggc ggt ctg      516
Thr Thr Thr Glu Gln Pro Glu Leu Tyr Ala Asp Ile Ile Gly Gly Leu
                -5                  -1  1                   5 gcc tac acc atg ggc ggc cgc tgt tcg gtc ggc ttc gcg gcc acc aac      564
Ala Tyr Thr Met Gly Gly Arg Cys Ser Val Gly Phe Ala Ala Thr Asn
            10                  15                  20 gcc gcc ggt cag ccc ggg ttc gtc acc gcc ggt cac tgt ggc cgc gtg      612
Ala Ala Gly Gln Pro Gly Phe Val Thr Ala Gly His Cys Gly Arg Val
        25                  30                  35 ggc acc cag gtg acc atc ggc aac ggc cgg ggc gtc ttc gag cag tcc      660
Gly Thr Gln Val Thr Ile Gly Asn Gly Arg Gly Val Phe Glu Gln Ser
40                  45                  50                  55 atc ttc ccg ggc aac gac gcc gcc ttc gtc cgc gga acg tcc aac ttc      708
Ile Phe Pro Gly Asn Asp Ala Ala Phe Val Arg Gly Thr Ser Asn Phe
                60                  65                  70 acg ctg acc aac ctg gtc agc cgc tac aac acc ggc ggc tac gcc acc      756
Thr Leu Thr Asn Leu Val Ser Arg Tyr Asn Thr Gly Gly Tyr Ala Thr
            75                  80                  85 gtc gcc ggt cac aac cag gcg ccc atc ggc tcc tcc gtc tgc cgc tcc      804
Val Ala Gly His Asn Gln Ala Pro Ile Gly Ser Ser Val Cys Arg Ser
        90                  95                  100 ggc tcc acc acc ggt tgg cac tgc ggc acc atc cag gcc cgc ggc cag      852
Gly Ser Thr Thr Gly Trp His Cys Gly Thr Ile Gln Ala Arg Gly Gln
105                 110                 115 tcg gtg agc tac ccc gag ggc acc gtc acc aac atg acg cgg acc acc      900
Ser Val Ser Tyr Pro Glu Gly Thr Val Thr Asn Met Thr Arg Thr Thr
120                 125                 130                 135 gtg tgc gcc gag ccc ggc gac tcc ggc ggc tcc tac atc tcc ggc aac      948
Val Cys Ala Glu Pro Gly Asp Ser Gly Gly Ser Tyr Ile Ser Gly Asn
            140                 145                 150 cag gcc cag ggc gtc acc tcc ggc ggc tcc ggc aac tgc cgc acc ggc      996
Gln Ala Gln Gly Val Thr Ser Gly Gly Ser Gly Asn Cys Arg Thr Gly
        155                 160                 165 ggg acc acc ttc tac cag gag gtc acc ccc atg gtg aac tcc tgg ggc     1044
Gly Thr Thr Phe Tyr Gln Glu Val Thr Pro Met Val Asn Ser Trp Gly
    170                 175                 180 gtc cgt ctc cgg acc taa                                             1062
Val Arg Leu Arg Thr
    185
```

<210> SEQ ID NO 8
<211> LENGTH: 353
<212> TYPE: PRT
<213> ORGANISM: Nocardiopsis prasina DSM 15649 ("Protease 35")

<400> SEQUENCE: 8

Ala  Thr Gly Pro Leu Pro  Gln Ser Pro Thr Pro  Glu Ala Asp Ala

```
-165            -160            -155
Val Ser Met Gln Glu Ala Leu Gln Arg Asp Leu Gly Leu Thr Pro
-150            -145            -140

Leu Glu Ala Asp Glu Leu Leu Ala Ala Gln Asp Thr Ala Phe Glu
-135            -130            -125

Val Asp Glu Ala Ala Ala Glu Ala Ala Gly Asp Ala Tyr Gly Gly
-120            -115            -110

Ser Val Phe Asp Thr Glu Thr Leu Glu Leu Val Leu Val Thr Asp
-105            -100            -95             -90

Ser Ala Ala Val Glu Ala Val Glu Ala Thr Gly Ala Gly Thr Glu Leu
                -85             -80             -75

Val Ser Tyr Gly Ile Thr Gly Leu Asp Glu Ile Val Glu Glu Leu Asn
        -70             -65             -60

Ala Ala Asp Ala Val Pro Gly Val Gly Trp Tyr Pro Asp Val Ala
        -55             -50             -45

Gly Asp Thr Val Val Leu Glu Val Leu Glu Gly Ser Gly Ala Asp Val
    -40             -35             -30

Gly Gly Leu Leu Ala Asp Ala Gly Val Asp Ala Ser Ala Val Glu Val
-25             -20             -15             -10

Thr Thr Thr Glu Gln Pro Glu Leu Tyr Ala Asp Ile Ile Gly Gly Leu
                -5              -1  1           5

Ala Tyr Thr Met Gly Gly Arg Cys Ser Val Gly Phe Ala Ala Thr Asn
            10              15              20

Ala Ala Gly Gln Pro Gly Phe Val Thr Ala Gly His Cys Gly Arg Val
        25              30              35

Gly Thr Gln Val Thr Ile Gly Asn Gly Arg Gly Val Phe Glu Gln Ser
40              45              50              55

Ile Phe Pro Gly Asn Asp Ala Ala Phe Val Arg Gly Thr Ser Asn Phe
                60              65              70

Thr Leu Thr Asn Leu Val Ser Arg Tyr Asn Thr Gly Gly Tyr Ala Thr
                75              80              85

Val Ala Gly His Asn Gln Ala Pro Ile Gly Ser Ser Val Cys Arg Ser
            90              95              100

Gly Ser Thr Thr Gly Trp His Cys Gly Thr Ile Gln Ala Arg Gly Gln
105                 110             115

Ser Val Ser Tyr Pro Glu Gly Thr Val Thr Asn Met Thr Arg Thr Thr
120             125             130             135

Val Cys Ala Glu Pro Gly Asp Ser Gly Ser Tyr Ile Ser Gly Asn
                140             145             150

Gln Ala Gln Gly Val Thr Ser Gly Ser Gly Asn Cys Arg Thr Gly
            155             160             165

Gly Thr Thr Phe Tyr Gln Glu Val Thr Pro Met Val Asn Ser Trp Gly
        170             175             180

Val Arg Leu Arg Thr
        185

<210> SEQ ID NO 9
<211> LENGTH: 1068
<212> TYPE: DNA
<213> ORGANISM: Nocardiopsis alba DSM 15647 ("Protease 08")
<220> FEATURE:
<221> NAME/KEY: CDS
<222> LOCATION: (1)..(1065)
<220> FEATURE:
<221> NAME/KEY: mat_peptide
<222> LOCATION: (502)..(1065)
```

<400> SEQUENCE: 9

```
gcg acc ggc ccc ctc ccc cag tcc ccc acc ccg gat gaa gcc gag      45
Ala Thr Gly Pro Leu Pro Gln Ser Pro Thr Pro Asp Glu Ala Glu
        -165             -160             -155 gcc acc acc atg gtc gag gcc ctc cag cgc gac ctc ggc ctg tcc      90
Ala Thr Thr Met Val Glu Ala Leu Gln Arg Asp Leu Gly Leu Ser
        -150             -145             -140 ccc tct cag gcc gac gag ctc ctc gag gcg cag gcc gag tcc ttc     135
Pro Ser Gln Ala Asp Glu Leu Leu Glu Ala Gln Ala Glu Ser Phe
        -135             -130             -125 gag atc gac gag gcc gcc acc gcg gcc gca gcc gac tcc tac ggc     180
Glu Ile Asp Glu Ala Ala Thr Ala Ala Ala Ala Asp Ser Tyr Gly
        -120             -115             -110 ggc tcc atc ttc gac acc gac agc ctc acc ctg acc gtc ctg gtc acc 228
Gly Ser Ile Phe Asp Thr Asp Ser Leu Thr Leu Thr Val Leu Val Thr
        -105             -100              -95 gac gcc tcc gcc gtc gag gcg gtc gag gcc gcc ggc gcc gag gcc aag 276
Asp Ala Ser Ala Val Glu Ala Val Glu Ala Ala Gly Ala Glu Ala Lys
         -90              -85              -80 gtg gtc tcg cac ggc atg gag ggc ctg gag gag atc gtc gcc gac ctg 324
Val Val Ser His Gly Met Glu Gly Leu Glu Glu Ile Val Ala Asp Leu
-75              -70              -65              -60 aac gcg gcc gac gct cag ccc ggc gtc gtg ggc tgg tac ccc gac atc 372
Asn Ala Ala Asp Ala Gln Pro Gly Val Val Gly Trp Tyr Pro Asp Ile
                 -55              -50              -45 cac tcc gac acg gtc gtc ctc gag gtc ctc gag ggc tcc ggt gcc gac 420
His Ser Asp Thr Val Val Leu Glu Val Leu Glu Gly Ser Gly Ala Asp
             -40              -35              -30 gtg gac tcc ctg ctc gcc gac gcc ggt gtg gac acc gcc gac gtc aag 468
Val Asp Ser Leu Leu Ala Asp Ala Gly Val Asp Thr Ala Asp Val Lys
         -25              -20              -15 gtg gag agc acc acc gag cag ccc gag ctg tac gcc gac atc atc ggc 516
Val Glu Ser Thr Thr Glu Gln Pro Glu Leu Tyr Ala Asp Ile Ile Gly
         -10               -5               -1   1                5 ggt ctc gcc tac acc atg ggt ggg cgc tgc tcg gtc ggc ttc gcg gcc 564
Gly Leu Ala Tyr Thr Met Gly Gly Arg Cys Ser Val Gly Phe Ala Ala
                  10               15               20 acc aac gcc tcc ggc cag ccc ggg ttc gtc acc gcc ggc cac tgc ggc 612
Thr Asn Ala Ser Gly Gln Pro Gly Phe Val Thr Ala Gly His Cys Gly
              25               30               35 acc gtc ggc acc ccg gtc agc atc ggc aac ggc cag ggc gtc ttc gag 660
Thr Val Gly Thr Pro Val Ser Ile Gly Asn Gly Gln Gly Val Phe Glu
          40               45               50 cgt tcc gtc ttc ccc ggc aac gac tcc gcc ttc gtc cgc ggc acc tcg 708
Arg Ser Val Phe Pro Gly Asn Asp Ser Ala Phe Val Arg Gly Thr Ser
55               60               65 aac ttc acc ctg acc aac ctg gtc agc cgc tac aac acc ggt ggt tac 756
Asn Phe Thr Leu Thr Asn Leu Val Ser Arg Tyr Asn Thr Gly Gly Tyr
70               75               80               85 gcg acc gtc tcc ggc tcc tcg cag gcg gcg atc ggc tcg cag atc tgc 804
Ala Thr Val Ser Gly Ser Ser Gln Ala Ala Ile Gly Ser Gln Ile Cys
             90               95              100 cgt tcc ggc tcc acc acc ggc tgg cac tgc ggc acc gtc cag gcc cgc 852
Arg Ser Gly Ser Thr Thr Gly Trp His Cys Gly Thr Val Gln Ala Arg
             105              110              115 ggc cag acg gtg agc tac ccc cag ggc acc gtg cag aac ctg acc cgc 900
Gly Gln Thr Val Ser Tyr Pro Gln Gly Thr Val Gln Asn Leu Thr Arg
         120              125              130
```

```
acc aac gtc tgc gcc gag ccc ggt gac tcc ggc ggc tcc ttc atc tcc      948
Thr Asn Val Cys Ala Glu Pro Gly Asp Ser Gly Gly Ser Phe Ile Ser
    135                 140                 145 ggc agc cag gcc cag ggc gtc acc tcc ggt ggc tcc ggc aac tgc tcc      996
Gly Ser Gln Ala Gln Gly Val Thr Ser Gly Gly Ser Gly Asn Cys Ser
150                 155                 160                 165 ttc ggt ggc acc acc tac tac cag gag gtc aac ccg atg ctg agc agc     1044
Phe Gly Gly Thr Thr Tyr Tyr Gln Glu Val Asn Pro Met Leu Ser Ser
                170                 175                 180 tgg ggt ctg acc ctg cgc acc tga                                     1068
Trp Gly Leu Thr Leu Arg Thr
            185
```

<210> SEQ ID NO 10
<211> LENGTH: 355
<212> TYPE: PRT
<213> ORGANISM: Nocardiopsis alba DSM 15647 ("Protease 08")

<400> SEQUENCE: 10

```
Ala Thr Gly  Pro Leu Pro Gln Ser  Pro Thr Pro Asp Glu  Ala Glu
        -165                -160                 -155

Ala Thr Thr  Met Val Glu Ala Leu  Gln Arg Asp Leu Gly  Leu Ser
        -150                -145                 -140

Pro Ser Gln  Ala Asp Glu Leu Leu  Glu Ala Gln Ala Glu  Ser Phe
        -135                -130                 -125

Glu Ile Asp  Glu Ala Ala Thr Ala  Ala Ala Ala Asp Ser  Tyr Gly
        -120                -115                 -110

Gly Ser Ile  Phe Asp Thr Asp Ser  Leu Thr Leu Thr Val  Leu Val Thr
        -105                -100                 -95

Asp Ala Ser  Ala Val Glu Ala Val  Glu Ala Ala Gly Ala  Glu Ala Lys
         -90                 -85                 -80

Val Val Ser  His Gly Met Glu Gly  Leu Glu Glu Ile Val  Ala Asp Leu
-75                  -70                 -65                 -60

Asn Ala Ala  Asp Ala Gln Pro Gly  Val Val Gly Trp Tyr  Pro Asp Ile
         -55                 -50                 -45

His Ser Asp  Thr Val Val Leu Glu  Val Leu Glu Gly Ser  Gly Ala Asp
         -40                 -35                 -30

Val Asp Ser  Leu Leu Ala Asp Ala  Gly Val Asp Thr Ala  Asp Val Lys
         -25                 -20                 -15

Val Glu Ser  Thr Thr Glu Gln Pro  Glu Leu Tyr Ala Asp  Ile Ile Gly
-10                  -5                  -1   1                5

Gly Leu Ala  Tyr Thr Met Gly Gly  Arg Cys Ser Val Gly  Phe Ala Ala
              10                  15                  20

Thr Asn Ala  Ser Gly Gln Pro Gly  Phe Val Thr Ala Gly  His Cys Gly
              25                  30                  35

Thr Val Gly  Thr Pro Val Ser Ile  Gly Asn Gly Gln Gly  Val Phe Glu
              40                  45                  50

Arg Ser Val  Phe Pro Gly Asn Asp  Ser Ala Phe Val Arg  Gly Thr Ser
55                   60                  65

Asn Phe Thr  Leu Thr Asn Leu Val  Ser Arg Tyr Asn Thr  Gly Gly Tyr
70                   75                  80                  85

Ala Thr Val  Ser Gly Ser Gln Ala  Ala Ile Gly Ser Gln  Ile Cys
              90                  95                  100

Arg Ser Gly  Ser Thr Gly Trp His  Cys Gly Thr Val Gln  Ala Arg
              105                 110                 115

Gly Gln Thr  Val Ser Tyr Pro Gln  Gly Thr Val Gln Asn  Leu Thr Arg
```

-continued

```
                        120                 125                 130
Thr Asn Val Cys Ala Glu Pro Gly Asp Ser Gly Ser Phe Ile Ser
    135                 140                 145

Gly Ser Gln Ala Gln Gly Val Thr Ser Gly Gly Ser Gly Asn Cys Ser
150                 155                 160                 165

Phe Gly Gly Thr Thr Tyr Tyr Gln Glu Val Asn Pro Met Leu Ser Ser
                170                 175                 180

Trp Gly Leu Thr Leu Arg Thr
            185

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
ccgattatgg agcggattga acatgcg                                      27

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
gtgaccatcg gcgacggcag gggcgtcttc g                                 31

<210> SEQ ID NO 13
<211> LENGTH: 10172
<212> TYPE: DNA
<213> ORGANISM: Artificial Sequence
<220> FEATURE:
<223> OTHER INFORMATION: Expression Cassette
<220> FEATURE:
<221> NAME/KEY: source
<222> LOCATION: (1)..(3323)
<223> OTHER INFORMATION: Bacillus subtilis genome sequence including
      yfmH-yfmD-yfmC-yfmB-yfmA genes
<220> FEATURE:
<221> NAME/KEY: misc_recomb
<222> LOCATION: (3561)..(4208)
<223> OTHER INFORMATION: Cat gene providing chloramphenicol resistance
<220> FEATURE:
<221> NAME/KEY: promoter
<222> LOCATION: (4523)..(5633)
<223> OTHER INFORMATION: Triple PamyL-scBAN-CryIIIA promoter including
      mRNA stabilizing sequence
<220> FEATURE:
<221> NAME/KEY: sig_peptide
<222> LOCATION: (5658)..(5738)
<220> FEATURE:
<221> NAME/KEY: CDS
<222> LOCATION: (5658)..(6797)
<220> FEATURE:
<221> NAME/KEY: mat_peptide
<222> LOCATION: (6234)..(6797)
<220> FEATURE:
<221> NAME/KEY: source
<222> LOCATION: (6839)..(7540)
<223> OTHER INFORMATION: Part of Bacillus subtilis pectate lyase gene
<220> FEATURE:
<221> NAME/KEY: source
<222> LOCATION: (7541)..(10172)
<223> OTHER INFORMATION: Bacillus subtilis genome DNA inclding yflS-citM
      genes

<400> SEQUENCE: 13
```

-continued

```
gagtatcgcc agtaaggggc gttttTgttt tctggttgtt ttcttcattt caggtttcgc      60
cctttccttg ccaaatataa gaaaaacggc gttccgataa tcgcggtgac aatgccgacc     120
ggtgattcat aaggaaatgc aatccatctg gccagaacat ctgcgtacac cagcaaaatg     180
gcaccgaaca gtgccgaaaa cggaagcacg tattgataat gttctccgat cagcttgcgg     240
acaatatgcg ggacgagcag cccgacaaag ccaatcggcc cggcgacggc tacgaagcg      300 ccggaaagaa ttaaaataat caaactgatc agaatcctga tgccgttcat attttgtcca     360
agcccttttg ctgtttcgtc tccgagaccg agaacagaaa cagaaccgga aaatacgagg     420
gcaagcccga tgccaatgac agaaaaagga gcgatggtta tgacgtcctg ccagttgctg     480
ccgtcgattg cgcctgtcat ccagtacaga acatcctcac ctgactcatt taaaataatg     540
atggcctgtg tcatagagga gaggaacaag tgcacggcca ttcctgacag cgccagcttg     600
acaggcgtca ttccgccgga tgaggcaatc atatacacaa tcgcgccgcc tgctgccgca     660
cccgcaaaag cgaatataac agatgaatag ggcgatgccg gcagaatgac gagagaagca     720
acaacaaaaa gcgatgcacc cgcattcaca ccgaaaattt ggggtgaagc cagaggattt     780
ctggtcatag cctgcatcag cgcccctgct acagctaggc tggcgccgac aaaaacgccg     840
attaatgtgc ggggaaggcg aagagtagag atgatgagct gttcctttga accgtcccat     900
acaaaaagat atttcaatga atctatgatg ctgatgtctg aggctcctac tgaaagattc     960
agcccaagcc caaatataaa ataatcagtg caatgataa acatcatcag tcttgatgat    1020
gagcgccgtt tggctgaatg atacaacagt ctcacttcct tactgcgtct ggttgcaaaa    1080
acgaagaagc aaggattccc ctcgcttctc atttgtccta tttattatac actttTttaa    1140
gcacatcttt ggcgcttgtt tcactagact tgatgcctct gaatcttgtc caagtgtcac    1200
ggtccgcatc atagacttgt ccattTttca ccgctttgag attTttccag agcgggttcg    1260
ttttccactc atctacaatg gttttgcctt cgttggctga gatgaacaaa atatcaggat    1320
cgattttgct caattgctca aggctgacct cttgataggc gttatctgac ttcacagcgt    1380
gtgtaaagcc tagcattTta aagatttctc cgtcatagga tgatgatgta tgaagctgga    1440
aggaatccgc tcttgcaacg ccgagaacga tgttgcggtt ttcatctttc ggaagttcgg    1500
cttttagatc gttgatgact ttTttgtgct cggcaagctt ttcttttcct tcatcttctt    1560
tatttaatgc tttagcaatg gtcgtaaagc tgtcgatcgt ttcgtcatat gtcgcttcac    1620
ggcttTttaa ttcaatcgtc ggggcgattt ttTtcagctg tTtataaatg ttTttatggc    1680
gctcagcgtc agcgatgatt aaatcaggct tcaaggaact gatgacctca agattgggtt    1740
cgctgcgtgt gcctacagat gtgtaatcaa tggagctgcc gacaagcttt ttaatcatat    1800
cttttttgtt gtcatctgcg atgcccaccg gcgtaatgcc gagattgtga acggcatcca    1860
agaatgaaag ctcaagcaca accacccgct taggtgtgcc gcttactgtc gttttTcctt    1920
cttcgtcatg gatcactctg gaatccttag actcgctttt gccgcttccg ttgttattct    1980
ggcttgatga acagccggat acaatgaggc aggcgagcaa taaacactc atgatggcaa     2040 tcaacttgtt agaataggtg cgcatgtcat tcttccttTt ttcagattTa gtaatgagaa    2100
tcattatcac atgtaacact ataatagcat ggcttatcat gtcaatatTt ttTtagtaaa    2160
gaaagctgcg ttTttactgc ttTctcatga agcatcatc agacacaaat aagtggtatg     2220
cagcgttacc gtgtcttcga gacaaaaacg catgggcgtt ggcttagag gtttcgaaca     2280 tatcagcagt gacataagga aggagagtgc tgagataacc ggacaattTc ttTtctattt    2340
```

```
catctgttag tgcaaattca atgtcgccga tattcatgat aatcgagaaa acaaagtcga   2400
tatcgatatg aaaatgttcc tcggcaaaaa ccgcaagctc gtgaattcct ggtgaacatc   2460
cggcacgctt atggaaaatc tgtttgacta aatcactcac aatccaagca ttgtattgct   2520
gttctggtga aaagtattgc attagacata cctcctgctc gtacggataa aggcagcgtt   2580
tcatggtcgt gtgctccgtg cagcggcttc tccttaattt tgattttttct gaaaataggt   2640 cccgttccta tcactttacc atggacggaa acaaatagc tactaccatt cctcctgttt   2700
ttctcttcaa tgttctggaa tctgtttcag gtacagacga tcgggtatga aagaaatata   2760
gaaaacatga aggaggaata tcgacatgaa accagttgta aaagagtata caatgacga   2820 acagctcatg aaagatgtag aggaattgca gaaatgggt gttgcgaaag aggatgtata   2880
cgtcttagct cacgacgatg acagaacgga acgcctggct gacaacacga acgccaacac   2940
gatcggagcc aaagaaacag gtttcaagca cgcggtggga aatatcttca ataaaaaagg   3000
agacgagctc cgcaataaaa ttcacgaaat cggtttttct gaagatgaag ccgctcaatt   3060
tgaaaaacgc ttagatgaag gaaaagtgct tctctttgtg acagataacg aaaaagtgaa   3120
agcttgggca taaagcaagg aaaaaaccaa aaggccaatg tcggcctttt ggtttttttg   3180
cggtctttgc ggtgggattt tgcagaatgc cgcaatagga tagcggaaca ttttcggttc   3240
tgaatgtccc tcaatttgct attatatttt tgtgataaat tggaataaaa tctcacaaaa   3300
tagaaaatgg gggtacatag tggccatcat ggccagctag catgcacatg ggatctggga   3360
ccaataataa tgactagaga agaaagaatg aagattgttc atgaaattaa ggaacgaata   3420
ttggataaag tggggtattt ttaaaatata tatttatgtt acagtaatat tgacttttaa   3480
aaaaggattg attctaagaa gaaagcagac aagtaagcct cctaaattca ctttagataa   3540
aaatttagga ggcatatcaa atgaacttta ataaaattga tttagacaat tggaagagaa   3600
aagagatatt taatcattat ttgaaccaac aaacgacttt tagtataacc acagaaattg   3660
atattagtgt tttataccga aacataaaac aagaaggata taaattttac cctgcattta   3720
ttttcttagt gacaagggtg ataaactcaa atacagcttt tagaactggt tacaatagcg   3780
acggagagtt aggttattgg gataagttag agccacttta tacaattttt gatggtgtat   3840
ctaaaacatt ctctggtatt tggactcctg taaagaatga cttcaaagag ttttatgatt   3900 tataccttc tgatgtagag aaatataatg gttcggggaa attgtttccc aaaacaccta   3960
tacctgaaaa tgcttttttct ctttctatta ttccatggac ttcatttact gggtttaact   4020
taaatatcaa taataatagt aattaccttc tacccattat tacagcagga aaattcatta   4080
ataaaggtaa ttcaatatat ttaccgctat ctttacaggt acatcattct gtttgtgatg   4140
gttatcatgc aggattgttt atgaactcta ttcaggaatt gtcagatagg cctaatgact   4200 ggctttata atatgagata atgccgactg tacttttac agtcggtttt ctaacgatac   4260
attaataggt acgaaaaagc aactttttt gcgcttaaaa ccagtcatac caataactta   4320
agggtaacta gcctcgccgg aaagagcgaa aatgcctcac atttgtgcca cctaaaaagg   4380
agcgatttac atatgagtta tgcagtttgt agaatgcaaa aagtgaaatc agctggacta   4440
aaaggcatgg catgccttcg atagtttatt aatattagtg gagctcagtg agagcgaagc   4500
gaacacttga tttttttaatt ttctatcttt tataggtcat tagagtatac ttatttgtcc   4560
tataaactat ttagcagcat aatagattta ttgaataggt catttaagtt gagcatatta   4620
ggggaggaaa atcttggaga aatatttgaa gaacccgagg atctagatca ggtaccgcaa   4680
cgttcgcaga tgctgctgaa gagattatta aaaagctgaa agcaaaaggc tatcaattgg   4740
```

-continued

```
taactgtatc tcagcttgaa gaagtgaaga agcagagagg ctattgaata aatgagtaga    4800
aagcgccata tcggcgcttt tcttttggaa gaaaatatag ggaaaatggt acttgttaaa    4860
aattcggaat atttatacaa tatcatatgt atcacattga aaggaggggc ctgctgtcca    4920
gactgtccgc tgtgtaaaaa aaaggaataa agggggttg acattatttt actgatatgt     4980
ataatataat ttgtataaga aaatggaggg ccctcgaaa cgtaagatga aaccttagat      5040
aaaagtgctt tttttgttgc aattgaagaa ttattaatgt taagcttaat taaagataat    5100
atctttgaat tgtaacgccc ctcaaaagta agaactacaa aaaagaata cgttatatag     5160 aaatatgttt gaaccttctt cagattacaa atatattcgg acggactcta cctcaaatgc    5220
ttatctaact atagaatgac atacaagcac aaccttgaaa atttgaaaat taactacca    5280 atgaacttgt tcatgtgaat tatcgctgta tttaattttc tcaattcaat atataatatg    5340
ccaatacatt gttacaagta gaaattaaga caccccttgat agccttacta tacctaacat   5400
gatgtagtat taaatgaata tgtaaatata tttatgataa gaagcgactt atttataatc   5460
attacatatt tttctattgg aatgattaag attccaatag aatagtgtat aaattattta   5520
tcttgaaagg agggatgcct aaaaacgaag aacattaaaa acatatattt gcaccgtcta    5580
atggatttat gaaaaatcat tttatcagtt tgaaaattat gtattatgga gctctgaaaa    5640
aaaggagagg ataaaga atg aag aaa   ccg ttg ggg aaa att   gtc gca agc    5690
                    Met Lys Lys  Pro Leu Gly Lys Ile  Val Ala Ser
                         -190                -185 acc gca  cta ctc att tct gtt  gct ttt agt tca tcg  atc gca tcg         5735
Thr Ala  Leu Leu Ile Ser Val  Ala Phe Ser Ser Ser  Ile Ala Ser
    -180                -175                 -170 gct gcc  acc gga gcg ctc ccc  cag tca ccc acc ccg  gag gcc gac         5780
Ala Ala  Thr Gly Ala Leu Pro  Gln Ser Pro Thr Pro  Glu Ala Asp
    -165                -160                 -155 gcg gtc  tcc atg cag gag gcg  ctc cag cgc gac ctc  gac ctg acc         5825
Ala Val  Ser Met Gln Glu Ala  Leu Gln Arg Asp Leu  Asp Leu Thr
    -150                -145                 -140 tcc gcc  gag gcc gag gag ctg  ctg gcc gcc cag gac  acc gcc ttc         5870
Ser Ala  Glu Ala Glu Glu Leu  Leu Ala Ala Gln Asp  Thr Ala Phe
    -135                -130                 -125 gag gtc  gac gag gcc gcg gcc  gag gcc gcc ggg gac  gcc tac ggc         5915
Glu Val  Asp Glu Ala Ala Ala  Glu Ala Ala Gly Asp  Ala Tyr Gly
    -120                -115                 -110 ggc tcc  gtc ttc gac acc gag  agc ctg gaa ctg acc gtc ctg gtc acc      5963
Gly Ser  Val Phe Asp Thr Glu  Ser Leu Glu Leu Thr Val Leu Val Thr
    -105                -100                  -95 gat gcc gcc gcg gtc gag gcc gtg gag gcc acc ggc gcc ggg acc gag        6011
Asp Ala Ala Ala Val Glu Ala Val Glu Ala Thr Gly Ala Gly Thr Glu
-90                 -85                  -80                  -75 ctg gtc tcc tac ggc atc gac ggt ctc gac gag atc gtc cag gag ctc        6059
Leu Val Ser Tyr Gly Ile Asp Gly Leu Asp Glu Ile Val Gln Glu Leu
                -70                  -65                  -60 aac gcc gcc gac gcc gtt ccc ggt gtg gtc ggc tgg tac ccg gac gtg        6107
Asn Ala Ala Asp Ala Val Pro Gly Val Val Gly Trp Tyr Pro Asp Val
            -55                  -50                  -45 gcg ggt gac acc gtc gtc ctg gag gtc ctg gag ggt tcc gga gcc gac        6155
Ala Gly Asp Thr Val Val Leu Glu Val Leu Glu Gly Ser Gly Ala Asp
        -40                  -35                  -30 gtc agc ggc ctg ctc gcg gac gcc ggc gtg gac gcc tcg gcc gtc gag        6203
Val Ser Gly Leu Leu Ala Asp Ala Gly Val Asp Ala Ser Ala Val Glu
    -25                  -20                  -15
```

```
gtg acc acg agc gac cag ccc gag ctc tac gcc gac atc atc ggt ggt    6251
Val Thr Thr Ser Asp Gln Pro Glu Leu Tyr Ala Asp Ile Ile Gly Gly
-10              -5              -1  1               5 ctg gcc tac acc atg ggc ggc cgc tgt tcg gtc ggc ttc gcg gcc acc    6299
Leu Ala Tyr Thr Met Gly Gly Arg Cys Ser Val Gly Phe Ala Ala Thr
            10              15              20 aac gcc gcc ggt cag ccc ggg ttc gtc acc gcc ggt cac tgc ggc cgc    6347
Asn Ala Ala Gly Gln Pro Gly Phe Val Thr Ala Gly His Cys Gly Arg
        25              30              35 gtg ggc acc cag gtg acc atc ggc aac ggc agg ggc gtc ttc gag cag    6395
Val Gly Thr Gln Val Thr Ile Gly Asn Gly Arg Gly Val Phe Glu Gln
    40              45              50 tcc gtc ttc ccc ggc aac gac gcg gcc ttc gtc cgc ggt acg tcc aac    6443
Ser Val Phe Pro Gly Asn Asp Ala Ala Phe Val Arg Gly Thr Ser Asn
55              60              65              70 ttc acg ctg acc aac ctg gtc agc cgc tac aac acc ggc ggg tac gcc    6491
Phe Thr Leu Thr Asn Leu Val Ser Arg Tyr Asn Thr Gly Gly Tyr Ala
            75              80              85 acg gtc gcc ggt cac aac cag gcc ccc atc ggc tcc tcc gtc tgc cgc    6539
Thr Val Ala Gly His Asn Gln Ala Pro Ile Gly Ser Ser Val Cys Arg
        90              95              100 tcc ggc tcc acc acc ggt tgg cac tgc ggc acc atc cag gcc cgc ggc    6587
Ser Gly Ser Thr Thr Gly Trp His Cys Gly Thr Ile Gln Ala Arg Gly
    105             110             115 cag tcg gtg agc tac ccc gag ggc acc gtc acc aac atg acc cgg acc    6635
Gln Ser Val Ser Tyr Pro Glu Gly Thr Val Thr Asn Met Thr Arg Thr
120             125             130 acc gtg tgc gcc gag ccc ggc gac tcc ggc ggc tcc tac atc tcc ggc    6683
Thr Val Cys Ala Glu Pro Gly Asp Ser Gly Gly Ser Tyr Ile Ser Gly
135             140             145             150 acc cag gcc cag ggc gtg acc tcc ggc ggc tcc ggc aac tgc cgc acc    6731
Thr Gln Ala Gln Gly Val Thr Ser Gly Gly Ser Gly Asn Cys Arg Thr
            155             160             165 ggc ggg acc acc ttc tac cag gag gtc acc ccc atg gtg aac tcc tgg    6779
Gly Gly Thr Thr Phe Tyr Gln Glu Val Thr Pro Met Val Asn Ser Trp
170             175             180 ggc gtc cgt ctc cgg acc taatcgcatg ttcaatccgc tccataatcg            6827
Gly Val Arg Leu Arg Thr
185 gtcgacgcgg cggttcgcgt ccggacagca catcaccgaa atattatgga agaaaatatc   6887 agcaccatga cggccaaacg gatgcttcca acggtgctaa ctatatcacg atgtcctaca   6947 actattatca cgatcatgat aaaagctcca ttttcggatc aagtgacagc aaaacctccg   7007 atgacggcaa attaaaaatt acgctgcatc ataaccgcta taaaaatatt gtccagcgcg   7067 cgccgagagt ccgcttcggg caagtgcacg tatacaacaa ctattatgaa ggaagcacaa   7127 gctcttcaag ttatccttt agctatgcat ggggaatcgg aaagtcatct aaaatctatg    7187 cccaaaacaa tgtcattgac gtaccgggac tgtcagctgc taaaacgatc agcgtattca   7247 gcggggggaac ggctttatat gactccggca cgttgctgaa cggcacacag atcaacgcat  7307 cggctgcaaa cgggctgagc tcttctgtcg gctggacgcc gtctctgcat ggatcgattg   7367 atgcttctgc taatgtgaaa tcaaatgtta taaatcaagc gggtgcgggt aaattaaatt   7427 aagaaagtga aaaacacaaa gggtgctaac ctttgtgttt tttaattaat taaaatgttt   7487 attaacttag ttaaggagta gaatggaaaa ggggatcgga aaacaagtat ataggaggag   7547 acctattta t ggcttcagaa aaagacgcag gaaaacagtc agcagtaaag cttgttccat   7607 tgcttattac tgtcgctgtg ggactaatca tctggtttat tcccgctccg tccggacttg   7667
```

```
aacctaaagc ttggcattg tttgcgattt ttgtcgcaac aattatcggc tttatctcca    7727
agcccttgcc aatgggtgca attgcaattt ttgcattggc ggttactgca ctaactggaa    7787
cactatcaat tgaggataca ttaagcggat tcgggaataa gaccatttgg cttatcgtta    7847
tcgcattctt tatttcccgg ggatttatca aaaccggtct cggtgcgaga atttcgtatg    7907
tattcgttca gaaattcgga aaaaaaaccc ttggactttc ttattcactg ctattcagtg    7967
atttaatact ttcacctgct attccaagta atacggcgcg tgcaggaggc attatatttc    8027
ctattatcag atcattatcc gaaacattcg gatcaagccc ggcaaatgga acagagagaa    8087
aaatcggtgc attcttatta aaaccggtt ttcagggaa tctgatcaca tctgctatgt      8147
tcctgacagc gatggcggcg aacccgctga ttgccaagct ggcccatgat gtcgcagggg    8207
tggacttaac atgacaagc tgggcaattg ccgcgattgt accgggactt gtaagcttaa     8267
tcatcacgcc gcttgtgatt tacaaactgt atccgccgga aatcaaagaa acaccggatg    8327
cggcgaaaat cgcaacagaa aaactgaaag aaatgggacc gttcaaaaaa tcggagcttt    8387
ccatggttat cgtgtttctt ttggtgcttg tgctgtggat ttttggcggc agcttcaaca    8447
tcgacgctac cacaaccgca ttgatcggtt tggccgttct cttattatca caagttctga    8507
cttgggatga tatcaagaaa gaacagggcg cttgggatac gctcacttgg tttgcggcgc    8567
ttgtcatgct cgccaacttc ttgaatgaat taggcatggt gtcttggttc agtaatgcca    8627
tgaaatcatc cgtatcaggg ttctcttgga ttgtggcatt catcatttta attgttgtgt    8687
attattactc tcactatttc tttgcaagtg cgacagccca catcagtgcg atgtattcag    8747
catttttggc tgtcgtcgtg gcagcgggcg caccgccgct tttagcagcg ctgagcctcg    8807
cgttcatcag caacctgttc gggtcaacga ctcactacgg ttctggagcg gctccggtct    8867
tcttcggagc aggctacatc ccgcaaggca atggtggtc catcggattt atcctgtcga     8927
ttgttcatat catcgtatgg cttgtgatcg gcggattatg gtggaaagta ctaggaatat    8987
ggtagaaaga aaaaggcaga cgcggtctgc cttttttat tttcactcct tcgtaagaaa     9047
atggattttg aaaaatgaga aaattccctg tgaaaatgg tatgatctag gtagaaagga     9107
cggctggtgc tgtggtgaaa aagcggttcc attttttccct gcaaacaaaa ataatggggc   9167
tgattgcggc tctgctggtc tttgtcattg gtgtgctgac cattacgtta gccgttcagc    9227
atacacaggg agaacggaga caggcagagc agctggcggt tcaaacggcg agaaccatt     9287
cctatatgcc gccggttaaa gagctcattg agagaaaaga cggacatgcg gctcagacgc    9347
aagaggtcat tgaacaaatg aaagaacaga ctggtgcgtt tgccatttat gttttgaacg    9407
aaaaaggaga cattcgcagc gcctctggaa aaagcggatt aaagaaactg gagcgcagca    9467
gagaaatttt gtttggcggt tcgcatgttt ctgaaacaaa agcggatgga cgaagagtga    9527
tcagagggag cgcgccgatt ataaaagaac agaaggata cagccaagtg atcggcagcg      9587
tgtctgttga ttttctgcaa acggagacag agcaaagcat caaaaagcat ttgagaaatt    9647
tgagtgtgat tgctgtgctt gtactgctgc tcggatttat tggcgccgcc gtgctggcga    9707
aaagcatcag aaaggatacg ctcgggcttg aaccgcatga gatcgcggct ctatatcgtg    9767
agaggaacgc aatgctttc gcgattcgag aagggattat tgccaccaat cgtgaaggcg     9827
tcgtcaccat gatgaacgta tcggcggccg agatgctgaa gctgcccgag cctgtgatcc    9887
atcttcctat agatgacgtc atgccggag cagggctgat gtctgtgctt gaaaaggag      9947
aaatgctgcc gaaccaggaa gtaagcgtca acgatcaagt gttatattct aatacgaaag    10007
```

```
tgatgaatca aggcgggcag gcgtatggga ttgtcgtcag cttcagggag aaaacagagc   10067
tgaagaagct gatcgacaca ttgacagagg ttcgcaaata ttcagaggat ctcagggcgc   10127
agactcatga attttcaaat aagctttatg cgattttagg gctgc                   10172
```

```
<210> SEQ ID NO 14
<211> LENGTH: 380
<212> TYPE: PRT
<213> ORGANISM: Artificial Sequence
<220> FEATURE:
<223> OTHER INFORMATION: Synthetic Construct

<400> SEQUENCE: 14

Met Lys Lys  Pro Leu Gly Lys Ile  Val Ala Ser Thr  Ala Leu Leu
             -190           -185               -180

Ile Ser Val  Ala Phe Ser Ser Ser  Ile Ala Ser Ala Ala  Thr Gly
        -175           -170                 -165

Ala Leu Pro  Gln Ser Pro Thr Pro  Glu Ala Asp Ala Val  Ser Met
        -160           -155                 -150

Gln Glu Ala  Leu Gln Arg Asp Leu  Asp Leu Thr Ser Ala  Glu Ala
        -145           -140                 -135

Glu Glu Leu  Leu Ala Ala Gln Asp  Thr Ala Phe Glu Val  Asp Glu
        -130           -125                 -120

Ala Ala Ala  Glu Ala Ala Gly Asp  Ala Tyr Gly Gly Ser  Val Phe
        -115           -110                 -105

Asp Thr Glu  Ser Leu Glu Leu Thr  Val Leu Val Thr Asp  Ala Ala Ala
        -100           -95                  -90

Val Glu Ala  Val Glu Ala Thr Gly  Ala Gly Thr Glu Leu  Val Ser Tyr
        -85            -80                  -75

Gly Ile Asp  Gly Leu Asp Glu Ile  Val Gln Glu Leu Asn  Ala Ala Asp
-70                 -65                  -60                -55

Ala Val Pro  Gly Val Val Gly Trp  Tyr Pro Asp Val Ala  Gly Asp Thr
        -50            -45                  -40

Val Val Leu  Glu Val Leu Glu Gly  Ser Gly Ala Asp Val  Ser Gly Leu
        -35            -30                  -25

Leu Ala Asp  Ala Gly Val Asp Ala  Ser Ala Val Glu Val  Thr Thr Ser
        -20            -15                  -10

Asp Gln Pro  Glu Leu Tyr Ala Asp  Ile Ile Gly Gly Leu  Ala Tyr Thr
        -5             -1  1                5                 10

Met Gly Gly  Arg Cys Ser Val Gly  Phe Ala Ala Thr Asn  Ala Ala Gly
             15                  20                  25

Gln Pro Gly  Phe Val Thr Ala Gly  His Cys Gly Arg Val  Gly Thr Gln
             30                  35                  40

Val Thr Ile  Gly Asn Gly Arg Gly  Val Phe Glu Gln Ser  Val Phe Pro
             45                  50                  55

Gly Asn Asp  Ala Ala Phe Val Arg  Gly Thr Ser Asn Phe  Thr Leu Thr
             60                  65                  70

Asn Leu Val  Ser Arg Tyr Asn Thr  Gly Gly Tyr Ala Thr  Val Ala Gly
75                  80                  85                  90

His Asn Gln  Ala Pro Ile Gly Ser  Ser Val Cys Arg Ser  Gly Ser Thr
             95                  100                 105

Thr Gly Trp  His Cys Gly Thr Ile  Gln Ala Arg Gly Gln  Ser Val Ser
             110                 115                 120

Tyr Pro Glu  Gly Thr Val Thr Asn  Met Thr Arg Thr Thr  Val Cys Ala
             125                 130                 135
```

-continued

```
Glu Pro Gly Asp Ser Gly Ser Tyr Ile Ser Gly Thr Gln Ala Gln
    140                 145                 150

Gly Val Thr Ser Gly Gly Ser Gly Asn Cys Arg Thr Gly Gly Thr Thr
155                 160                 165                 170

Phe Tyr Gln Glu Val Thr Pro Met Val Asn Ser Trp Gly Val Arg Leu
                175                 180                 185

Arg Thr

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
ggagctctga aaaaaggag aggataaaga atgaa                              35

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
gcgttccgat aatcgcggtg acaatgccg                                    29

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
ttcatgagtc tgcgccctga gatcctctg                                    29

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
taatcgcatg ttcaatccgc tccataatcg                                   30

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19
cccaacggtt tcttcattct ttatcctctc cttttttttca gagc                  44

<210> SEQ ID NO 20
<211> LENGTH: 1164
<212> TYPE: DNA
<213> ORGANISM: Artificial Sequence
<220> FEATURE:
<223> OTHER INFORMATION: Protease 22
<220> FEATURE:
```

```
<221> NAME/KEY: CDS
<222> LOCATION: (1)..(1164)
<220> FEATURE:
<221> NAME/KEY: sig_peptide
<222> LOCATION: (1)..(81)
<220> FEATURE:
<221> NAME/KEY: mat_peptide
<222> LOCATION: (577)..(1164)

<400> SEQUENCE: 20
```

| | | | | | | | | | | | | | | | |
|---|---|---|---|---|---|---|---|---|---|---|---|---|---|---|---|
| atg | aaa | aaa | ccg | ctg | gga | aaa | att | gtc | gca | agc | aca | gca | ctt | ctt | 45 |
| Met | Lys | Lys | Pro | Leu | Gly | Lys | Ile | Val | Ala | Ser | Thr | Ala | Leu | Leu | |
| -190 | | | | | -185 | | | | | -180 | | | | | |
| att | tca | gtg | gca | ttt | agc | tca | tct | att | gca | tca | gca | gct | aca | gga | 90 |
| Ile | Ser | Val | Ala | Phe | Ser | Ser | Ser | Ile | Ala | Ser | Ala | Ala | Thr | Gly | |
| | -175 | | | | | -170 | | | | | -165 | | | | |
| gca | tta | ccg | cag | tct | ccg | aca | ccg | gaa | gca | gat | gca | gtc | tca | atg | 135 |
| Ala | Leu | Pro | Gln | Ser | Pro | Thr | Pro | Glu | Ala | Asp | Ala | Val | Ser | Met | |
| | | -160 | | | | | -155 | | | | | -150 | | | |
| caa | gaa | gca | ctg | caa | aga | gat | ctt | gat | ctt | aca | tca | gca | gaa | gca | 180 |
| Gln | Glu | Ala | Leu | Gln | Arg | Asp | Leu | Asp | Leu | Thr | Ser | Ala | Glu | Ala | |
| | | | -145 | | | | | -140 | | | | | -135 | | |
| gaa | gaa | ctt | ctt | gct | gca | caa | gat | aca | gca | ttt | gaa | gtg | gat | gaa | 225 |
| Glu | Glu | Leu | Leu | Ala | Ala | Gln | Asp | Thr | Ala | Phe | Glu | Val | Asp | Glu | |
| | | | | -130 | | | | | -125 | | | | | -120 | |
| gca | gcg | gca | gaa | gca | gca | gga | gat | gca | tat | ggc | ggc | tca | gtt | ttt | 270 |
| Ala | Ala | Ala | Glu | Ala | Ala | Gly | Asp | Ala | Tyr | Gly | Gly | Ser | Val | Phe | |
| | | | -115 | | | | | -110 | | | | | -105 | | |
| gat | aca | gaa | tca | ctt | gaa | ctt | aca | gtt | ctt | gtt | aca | gat | gca | gca | gca | 318 |
| Asp | Thr | Glu | Ser | Leu | Glu | Leu | Thr | Val | Leu | Val | Thr | Asp | Ala | Ala | Ala |
| | | -100 | | | | | -95 | | | | | -90 | | | |
| gtt | gaa | gca | gtt | gaa | gca | aca | gga | gca | gga | aca | gta | ctt | gtt | tca | tat | 366 |
| Val | Glu | Ala | Val | Glu | Ala | Thr | Gly | Ala | Gly | Thr | Val | Leu | Val | Ser | Tyr |
| | | -85 | | | | | -80 | | | | | -75 | | | |
| gga | att | gat | ggc | ctt | gat | gaa | att | gtt | caa | gaa | ctg | aat | gca | gct | gat | 414 |
| Gly | Ile | Asp | Gly | Leu | Asp | Glu | Ile | Val | Gln | Glu | Leu | Asn | Ala | Ala | Asp |
| -70 | | | | | -65 | | | | | -60 | | | | | -55 |
| gct | gtt | ccg | ggc | gtt | gtt | ggc | tgg | tat | ccg | gat | gtt | gct | gga | gat | aca | 462 |
| Ala | Val | Pro | Gly | Val | Val | Gly | Trp | Tyr | Pro | Asp | Val | Ala | Gly | Asp | Thr |
| | | | -50 | | | | | -45 | | | | | -40 | | |
| gtt | gtc | ctt | gaa | gtt | ctt | gaa | gga | tca | ggc | gca | gat | gtt | tca | ggc | ctg | 510 |
| Val | Val | Leu | Glu | Val | Leu | Glu | Gly | Ser | Gly | Ala | Asp | Val | Ser | Gly | Leu |
| | | | | -35 | | | | | -30 | | | | | -25 | |
| ctg | gca | gac | gca | gga | gtc | gat | gca | tca | gca | gtt | gaa | gtt | aca | aca | tca | 558 |
| Leu | Ala | Asp | Ala | Gly | Val | Asp | Ala | Ser | Ala | Val | Glu | Val | Thr | Thr | Ser |
| | -20 | | | | | -15 | | | | | -10 | | | | |
| gat | caa | ccg | gaa | ctt | tat | gca | gat | att | att | ggc | ggc | ctg | gca | tat | tat | 606 |
| Asp | Gln | Pro | Glu | Leu | Tyr | Ala | Asp | Ile | Ile | Gly | Gly | Leu | Ala | Tyr | Tyr |
| | -5 | | | | | -1 | 1 | | | | 5 | | | | 10 |
| atg | ggc | ggc | aga | tgc | agc | gtt | ggc | ttt | gca | gca | aca | aat | gca | tca | ggc | 654 |
| Met | Gly | Gly | Arg | Cys | Ser | Val | Gly | Phe | Ala | Ala | Thr | Asn | Ala | Ser | Gly |
| | | | 15 | | | | | 20 | | | | | 25 | | |
| caa | ccg | ggc | ttt | gtt | aca | gca | ggc | cat | tgc | ggc | aca | gtt | ggc | aca | cca | 702 |
| Gln | Pro | Gly | Phe | Val | Thr | Ala | Gly | His | Cys | Gly | Thr | Val | Gly | Thr | Pro |
| | | 30 | | | | | 35 | | | | | 40 | | | |
| gtt | tca | att | ggc | aat | ggc | aaa | ggc | gtt | ttt | gaa | cga | agc | att | ttt | ccg | 750 |
| Val | Ser | Ile | Gly | Asn | Gly | Lys | Gly | Val | Phe | Glu | Arg | Ser | Ile | Phe | Pro |
| | | | 45 | | | | | 50 | | | | | 55 | | |
| ggc | aat | gat | tca | gca | ttt | gtt | aga | ggc | aca | tca | aat | ttt | aca | ctt | aca | 798 |
| Gly | Asn | Asp | Ser | Ala | Phe | Val | Arg | Gly | Thr | Ser | Asn | Phe | Thr | Leu | Thr |
| 60 | | | | | 65 | | | | | 70 | | | | | |

```
aat ctg gtt tca aga tat aat tca ggc ggc tat gca aca gtt gca ggc      846
Asn Leu Val Ser Arg Tyr Asn Ser Gly Gly Tyr Ala Thr Val Ala Gly
 75              80                  85                  90 cat aat caa gca ccg att ggc tca gca gtt tgc aga tca ggc tca aca      894
His Asn Gln Ala Pro Ile Gly Ser Ala Val Cys Arg Ser Gly Ser Thr
             95                 100                 105 aca ggc tgg cat tgc ggc aca att caa gca aga aat caa aca gtt agg      942
Thr Gly Trp His Cys Gly Thr Ile Gln Ala Arg Asn Gln Thr Val Arg
        110                 115                 120 tat ccg caa ggc aca gtt tat agt ctg aca aga aca aca gtt tgt gca      990
Tyr Pro Gln Gly Thr Val Tyr Ser Leu Thr Arg Thr Thr Val Cys Ala
    125                 130                 135 gaa ccg ggc gat tca ggc ggc tca tat att agc ggc act caa gca caa     1038
Glu Pro Gly Asp Ser Gly Gly Ser Tyr Ile Ser Gly Thr Gln Ala Gln
140                 145                 150 ggc gtt aca tca ggc ggc tca ggc aat tgc agt gct ggc ggc aca aca     1086
Gly Val Thr Ser Gly Gly Ser Gly Asn Cys Ser Ala Gly Gly Thr Thr
155                 160                 165                 170 tat tac caa gaa gtt aat ccg atg ctt agt tca tgg ggc ctt aca ctt     1134
Tyr Tyr Gln Glu Val Asn Pro Met Leu Ser Ser Trp Gly Leu Thr Leu
            175                 180                 185 aga aca caa tcg cat gtt caa tcc gct cca                             1164
Arg Thr Gln Ser His Val Gln Ser Ala Pro
        190                 195

<210> SEQ ID NO 21
<211> LENGTH: 388
<212> TYPE: PRT
<213> ORGANISM: Artificial Sequence
<220> FEATURE:
<223> OTHER INFORMATION: Synthetic Construct

<400> SEQUENCE: 21

Met Lys Lys  Pro Leu Gly Lys  Ile Val Ala Ser Thr Ala  Leu Leu
         -190             -185                 -180

Ile Ser Val  Ala Phe Ser Ser  Ile Ala Ser Ala Ala  Thr Gly
         -175             -170                 -165

Ala Leu Pro  Gln Ser Pro Thr  Pro Glu Ala Asp Ala Val  Ser Met
         -160             -155                 -150

Gln Glu Ala  Leu Gln Arg Asp  Leu Asp Leu Thr Ser Ala  Glu Ala
         -145             -140                 -135

Glu Glu Leu  Leu Ala Ala Gln Asp  Thr Ala Phe Glu Val  Asp Glu
         -130             -125                 -120

Ala Ala Ala  Glu Ala Ala Gly Asp  Ala Tyr Gly Gly Ser  Val Phe
         -115             -110                 -105

Asp Thr Glu  Ser Leu Glu Leu  Thr Val Leu Val Thr Asp Ala Ala Ala
         -100             -95                  -90

Val Glu Ala  Val Glu Ala Thr  Gly Ala Gly Thr Val Leu Val Ser Tyr
          -85              -80                  -75

Gly Ile Asp Gly Leu Asp Glu Ile Val Gln Glu Leu Asn Ala Ala Asp
-70                  -65                  -60                  -55

Ala Val Pro Gly Val Val Gly Trp Tyr Pro Asp Val Ala Gly Asp Thr
                 -50                  -45                  -40

Val Val Leu Glu Val Leu Glu Gly Ser Gly Ala Asp Val Ser Gly Leu
             -35                  -30                  -25

Leu Ala Asp Ala Gly Val Asp Ala Ser Ala Val Glu Val Thr Thr Ser
         -20                  -15                  -10

Asp Gln Pro Glu Leu Tyr Ala Asp Ile Ile Gly Gly Leu Ala Tyr Tyr
```

-continued

```
      -5                  -1   1               5                  10
Met Gly Gly Arg Cys Ser Val Gly Phe Ala Ala Thr Asn Ala Ser Gly
                 15              20              25

Gln Pro Gly Phe Val Thr Ala Gly His Cys Gly Thr Val Gly Thr Pro
                 30              35              40

Val Ser Ile Gly Asn Gly Lys Gly Val Phe Glu Arg Ser Ile Phe Pro
             45              50              55

Gly Asn Asp Ser Ala Phe Val Arg Gly Thr Ser Asn Phe Thr Leu Thr
         60              65              70

Asn Leu Val Ser Arg Tyr Asn Ser Gly Gly Tyr Ala Thr Val Ala Gly
 75              80              85                          90

His Asn Gln Ala Pro Ile Gly Ser Ala Val Cys Arg Ser Gly Ser Thr
                 95             100             105

Thr Gly Trp His Cys Gly Thr Ile Gln Ala Arg Asn Gln Thr Val Arg
             110             115             120

Tyr Pro Gln Gly Thr Val Tyr Ser Leu Thr Arg Thr Thr Val Cys Ala
             125             130             135

Glu Pro Gly Asp Ser Gly Gly Ser Tyr Ile Ser Gly Thr Gln Ala Gln
         140             145             150

Gly Val Thr Ser Gly Gly Ser Gly Asn Cys Ser Ala Gly Gly Thr Thr
155             160             165                         170

Tyr Tyr Gln Glu Val Asn Pro Met Leu Ser Ser Trp Gly Leu Thr Leu
                 175             180             185

Arg Thr Gln Ser His Val Gln Ser Ala Pro
                 190             195
```

PROTEASE VARIANTS

CROSS-REFERENCE TO RELATED APPLICATIONS

This application is a 35 U.S.C. 371 national application of PCT/DK/2004/000688 filed Oct. 8, 2004, which claims priority or the benefit under 35 U.S.C. 119 of Danish application nos. PA 2003 01494 filed Oct. 10, 2003 and PA 2004 00333 filed Mar. 1, 2004 and U.S. provisional application nos. 60/549,347 filed Mar. 2, 2004 and 60/510,450 filed Oct. 10, 2003, the contents of which are fully incorporated herein by reference.

FIELD OF THE INVENTION

The present invention relates to a novel protease 3D structure, as well as variants of a parent protease, in particular variants of amended properties, such as improved thermostability and/or amended temperature activity profile. The invention also relates to DNA sequences encoding such variants, their production in a recombinant host cell, as well as methods of using the variants, in particular within the field of animal feed and detergents. The invention furthermore relates to methods of generating and preparing protease variants of amended properties. Preferred parent proteases are Nocardiopsis proteases, such as proteases comprising the mature peptide parts of SEQ ID NOs: 2, 4, 6, 8, 10, and 21.

BACKGROUND OF THE INVENTION

Protease sequences derived from strains of Nocardiopsis are disclosed in WO 88/03947, WO 01/58276, and DK 1996 00013 ("Protease 10," SEQ ID NOs: 1-2).

JP 2003284571-A discloses, as SEQ ID NOs: 2 and 1, the amino acid sequence and the corresponding DNA sequence, respectively, of a protease derived from Nocardiopsis sp. TOA-1 (FERM P-18676). The sequences have been entered in the GENESEQ database as GENESEQP no. ADF43564, and GENESEQN no. ADF43563, respectively.

JP 2-255081-A discloses a protease derived from Nocardiopsis sp. strain OPC-210 (FERM P-10508), however without sequence information. The strain is no longer available, as the deposit was withdrawn.

DD 20043218 discloses a proteolytic preparation derived from Nocardiopsis dassonvillei strain ZIMET 43647, however without sequence information. The strain appears to be no longer available.

Additional Nocardiopsis protease sequences are disclosed in PCT/DK04/000433 ("Protease 08," SEQ ID NOs: 9-10 herein); PCT/DK04/000434 ("Protease 11," SEQ ID NOs: 5-6 herein); PCT/DK04/000432 ("Protease 18," SEQ ID NOs: 3-4 herein); and PCT/DK04/000435 ("Protease 35," SEQ ID NOs: 7-8 herein).

It is an object of the present invention to provide alternative proteases, in particular for use in animal feed and/or detergents, in particular novel and improved protease variants, preferably of amended properties, such as improved thermostability and/or a higher or lower optimum temperature.

SUMMARY OF THE INVENTION

The present invention relates to a variant of a parent protease, comprising a substitution in at least one position of at least one region selected from the group of regions consisting of: 6-18; 22-28; 32-39; 42-58; 62-63; 66-76; 78-100; 103-106; 111-114; 118-131; 134-136; 139-141; 144-151; 155-156; 160-176; 179-181; and 184-188; wherein
(a) the variant has protease activity; and
(b) each position corresponds to a position of amino acids 1 to 188 of SEQ ID NO: 2; and
(c) the variant has a percentage of identity to amino acids 1 to 188 of SEQ ID NO: 2 of at least 60%.

The present invention also relates to isolated nucleic acid sequences encoding the protease variant and to nucleic acid constructs, vectors, and host cells comprising the nucleic acid sequences as well as methods for producing and using the protease variants.

BRIEF DESCRIPTION OF THE FIGURES

FIG. 1 is a multiple alignment of Protease 10, Protease 18, Protease 11, Protease 35 and Protease 08 (the mature peptide parts of SEQ ID NOs: 2, 4, 6, 8 and 10, respectively), also including a protease variant of the invention, viz. Protease 22 (amino acids 1-188 of SEQ ID NO: 21); and FIG. 2 provides the coordinates of the novel 3D structure of Protease 10 (amino acids 1 to 188 of SEQ ID NO: 2) derived from Nocardiopsis sp. NRRL 18262.

DETAILED DESCRIPTION OF THE INVENTION

Three-Dimensional Structure of Protease 10

The structure of Protease 10 was solved in accordance with the principles for X-ray crystallographic methods as given, for example, in X-Ray Structure Determination, Stout, G. K. and Jensen, L. H., John Wiley & Sons, Inc. NY, 1989. The structural coordinates for the crystal structure at 2.2 Å resolution using the isomorphous replacement method are given in FIG. 2 in standard PDB format (Protein Data Bank, Brookhaven National Laboratory, Brookhaven, Conn.). The PDB file of FIG. 2 relates to the mature peptide part of Protease 10 corresponding to residues 1-188 of SEQ ID NO: 2.

Molecular Dynamics (MD)

Molecular Dynamics (MD) simulations are indicative of the mobility of the amino acids in a protein structure (see McCammon, J A and Harvey, S C., (1987), "Dynamics of proteins and nucleic acids", Cambridge University Press). Such protein dynamics are often compared to the crystallographic B-factors (see Stout, G H and Jensen, L H, (1989), "X-ray structure determination", Wiley). By running the MD simulation at, e.g., different temperatures, the temperature related mobility of residues is simulated. Regions having the highest mobility or flexibility (here isotropic fluctuations) may be suggested for random mutagenesis. It is here understood that the high mobility found in certain areas of the protein, may be thermally improved by substituting these residues.

Using the programs CHARMM (Accelrys) and NAMD (University of Illinois at Urbana-Champaign) the Protease 10 structure described above was subjected to MD at 300 and 400K. Starting from the coordinates of FIG. 2 hydrogen and missing heavy atoms were built using CHARMM procedures HBUILD and IC BUILD respectively. Then the structure was minimized using CHARMM Conjugate Gradients (CONJ) minimization procedure for a total of 200 steps. The protein was then put on a 70×70×70 Angstrom box and solvated with TIP3 water molecules. A total of 11124 water molecules were added and then minimized, keeping the protein coordinates fixed, using CHARMM Adopted Basis Newton Raphson (ABNR) minimization procedure for 20000 steps. The system was then heated to the desired temperature at a rate of 1K every 100 steps using the NAMD software. After an equilibration of 50 picoseconds, an NVE ensemble MD was run for 1 nanosecond, both steps done with the software NAMD. A cut-off of 12 Angstrom was used for the non-bonded interactions. Periodic boundary conditions were used after the salvation step and for all the subsequent ones. The isotropic root mean square (RMS) fluctuations were calculated with the CHARMM procedure COOR DYNA.

The following suggested regions for mutagenesis result from MD simulations: From residue 160 to 170, from residue 78 to 90, from residue 43 to 50, from residue 66 to 75, and from residue 22 to 28.

Strategy for Preparing Variants

Regions of amino acid residues, as well as individual amino acid substitutions, were suggested for mutagenesis based on the 3D-structure of FIG. 2 and the alignment of the five known proteases (upper five rows of FIG. 1), mainly with a view to improving thermostability.

The following regions were suggested, cf. claim 1: 6-18; 22-28; 32-39; 42-58; 62-63; 66-76; 78-100; 103-106; 111-114; 118-131; 134-136; 139-141; 144-151; 155-156; 160-176; 179-181; and 184-188.

At least one of the following positions of the above regions are preferably subjected to mutagenesis, cf. claim 3; 6; 7; 8; 9; 10; 12; 13; 16; 17; 18; 22; 23; 24; 25; 26; 27; 28; 32; 33; 37; 38; 39; 42; 43; 44; 45; 46; 47; 48; 49; 50; 51; 52; 53; 54; 55; 56; 58; 62; 63; 66; 67; 68; 69; 70; 71; 72; 73; 74; 75; 76; 78; 79; 80; 81; 82; 83; 84; 85; 86; 87; 88; 89; 90; 91; 92; 93; 94; 95; 96; 97; 98; 99; 100; 103; 105; 106; 111; 113; 114; 118; 120; 122; 124; 125; 127; 129; 130; 131; 134; 135; 136; 139; 140; 141; 144; 145; 146; 147; 148; 149; 150; 151; 155; 156; 160; 161; 162; 163; 164; 165; 166; 167; 168; 169; 170; 171; 172; 173; 174; 175; 176; 179; 180; 181; 184; 185; 186; 187; and/or 188.

Contemplated specific variants are listed in the claims, viz. variants of Protease 10, Protease 18, Protease 11, Protease 35 as well as Protease 08 in claims 4 and 15; variants of Protease 10 in claim 16; variants of Protease 18 in claim 17; variants of Protease 11 in claim 18; variants of Protease 35 in claim 19; and variants of Protease 08 in claim 20.

The various concepts underlying the invention are also reflected in the claims as follows: Stabilization by disulfide-bridges in claims 5 and 6; proline-stabilization in claims 7-8; substitution of exposed neutral residues with negatively charged residues in claims 9-10; substitution of exposed neutral residues with positively charged residues in claims 11-12; substitution of small residues with bulkier residues inside the protein in claim 13; and regions proposed for mutagenesis following MD simulations in claim 14.

The term "at least one" means "one or more," viz., e.g. in the context of regions: One, two, three, four, five, six, seven, eight, nine, ten, eleven, twelve, thirteen, fourteen, fifteen, sixteen, or seventeen; or, in the context of positions or substitutions: One, two, three, four, five, and so on, up to e.g. ninety.

In a particular embodiment, the number of regions proposed for and/or subjected to mutagenesis is at least one, two, three, four, five, six, seven, eight, nine, ten, eleven, twelve, thirteen, fourteen, fifteen, sixteen, or at least seventeen.

In another particular embodiment, the number of regions proposed for and/or subjected to mutagenesis is no more than one, two, three, four, five, six, seven, eight, nine, ten, eleven, twelve, thirteen, fourteen, fifteen, sixteen, or no more than seventeen.

Polypeptides Having Protease Activity

Polypeptides having protease activity, or proteases, are sometimes also designated peptidases, proteinases, peptide hydrolases, or proteolytic enzymes. Proteases may be of the exo-type that hydrolyse peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Bio-chem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at chem.qmw.ac.uk/iubmb/enzyme/index.html.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In particular embodiments, the parent proteases and/or the protease variants of the invention and for use according to the invention are selected from the group consisting of:

(a) Proteases belonging to the EC 3.4.-.- - enzyme group;

(b) Serine proteases belonging to the S group of the above Handbook;

(c1) Serine proteases of peptidase family S2A; and (c2) Serine proteases of peptidase family S1E as described in Biochem.J. 290:205-218 (1993) and in MEROPS protease database, release 6.20, Mar. 24, 2003, (merops.ac.uk). The database is described in Rawlings, N. D., O'Brien, E. A. & Barrett, A. J. (2002) MEROPS: the protease database. Nucleic Acids Res. 30, 343-346.

For determining whether a given protease is a Serine protease, and a family S2A protease, reference is made to the above Handbook and the principles indicated therein. Such determination can be carried out for all types of proteases, be it naturally occurring or wild-type proteases; or genetically engineered or synthetic proteases.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Examples of protease substrates are casein, such as Azurine-Crosslinked Casein (AZCL-casein). Examples of suitable protease assays are described in the experimental part.

Parent Protease

The parent protease is a protease from which the protease variant is, or can be, derived. For the present purposes, any protease can be used as the parent protease, as long as the resulting protease variant is homologous to Protease 10, i.e.

the protease derived from Nocardiopsis sp. NRRL 18262 and comprising amino acids 1-188 of SEQ ID NO: 2.

In a particular embodiment the parent protease is also homologous to Protease 10.

In the present context, homologous means having an identity of at least 60% to SEQ ID NO: 2, viz. amino acids 1-188 of the mature peptide part of Protease 10. Homology is determined as generally described below in the section entitled Amino Acid Homology.

The parent protease may be a wild-type or naturally occurring polypeptide, or an allelic variant thereof, or a fragment thereof that has protease acticity, in particular a mature part thereof. It may also be a variant thereof and/or a genetically engineered or synthetic polypeptide.

In a particular embodiment the wild-type parent protease is i) a bacterial protease; ii) a protease of the phylum Actinobacteria; iii) of the class Actinobacteria; iv) of the order Actinomycetales v) of the family Nocardiopsaceae; vi) of the genus *Nocardiopsis*; and/or a protease derived from vii) *Nocardiopsis* species, such as *Nocardiopsis alba, Nocardiopsis antarctica, Nocardiopsis composta, Nocardiopsis dassonvillei, Nocardiopsis exhalans, Nocardiopsis halophila, Nocardiopsis halotolerans, Nocardiopsis kunsanensis, Nocardiopsis listeri, Nocardiopsis lucentensis, Nocardiopsis metallicus, Nocardiopsis prasina, Nocardiopsis sp., Nocardiopsis synnemataformans, Nocardiopsis trehalosi, Nocardiopsis tropica, Nocardiopsis umidischolae*, or *Nocardiopsis xinjiangensis*.

Examples of such strains are: *Nocardiopsis alba* DSM 15647 (wild-type producer of Protease 08), *Nocardiopsis dassonvillei* NRRL 18133 (wild-type producer of Protease M58-1 described in WO 88/03947), *Nocardiopsis dassonvillei* subsp. *dassonvillei* DSM 43235 (wild-type producer of Protease 18), *Nocardiopsis prasina* DSM 15648 (wild-type producer of Protease 11), *Nocardiopsis prasina* DSM 15649 (wild-type producer of Protease 35), *Nocardiopsis* sp. NRRL 18262 (wild-type producer of Protease 10), *Nocardiopsis* sp. FERM P-18676 (described in JP 2003284571-A).

Strains of these species are accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL), e.g. *Nocardiopsis dassonvillei* subsp. *dassonvillei* DSM 43235 is publicly available from DSMZ (Deutsche Sammlung von Mikroorganismen und Zelikulturen GmbH, Braunschweig, Germany).

Furthermore, such polypeptides may be identified and obtained from other sources including microorganisms or DNA isolated from nature (e.g., soil, composts, water, etc.) using suitable probes. Techniques for isolating microorganisms or DNA from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The parent protease may be a mature part of any of the amino acid sequences referred to above. A mature part means a mature amino acid sequence and refers to that part of an amino acid sequence which remains after a potential signal peptide part and/or pro-peptide part has been cleaved off. The mature parts of each of the proteases Protease 08, 10, 11, 18, 22 and 35 are specified in the appended sequence listing.

The parent protease may also be a fragment of a specified amino acid sequence, viz. a polypeptide having one or more amino acids deleted from the amino and/or carboxyl terminus of this amino acid sequence. In one embodiment, a fragment contains at least 80, or at least 90, or at least 100, or at least 110, or at least 120, or at least 130, or at least 140, or at least 150, or at least 160, or at least 170, or at least 180, or at least 185 amino acid residues.

The parent protease may also be an allelic variant, allelic referring to the existence of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In another embodiment, the parent protease may be a genetically engineered protease, e.g. a variant of the wild-type or natural parent proteases referred to above comprising a substitution, deletion, and/or insertion of one or more amino acids. In other words: The parent protease may itself be a protease variant, such as Protease 22. The amino acid sequence of such parent protease may differ from the amino acid sequence specified by an insertion or deletion of one or more amino acid residues and/or the substitution of one or more amino acid residues by different amino acid residues. The amino acid changes may be of a minor, or of a major, nature. Amino acid changes of a major nature are e.g. those resulting in a variant protease of the present invention with amended properties. In another particular embodiment, the amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/PrQ, Lys/Arg, Asp/Asn, Leu/Ile, Leu/Val, Ala/Glu, and Asp/Gly as well as these in reverse.

Still further examples of genetically engineered parent proteases are synthetic proteases, designed by man, and expectedly not occurring in nature. EP 897985 discloses a process of preparing a consensus protein. Shuffled proteases are other examples of synthetic or genetically engineered parent proteases, which can be prepared as is generally known in the art, eg by Site-directed Mutagenesis, by PCR (using a PCR fragment containing the desired mutation as one of the primers in the PCR reactions), or by Random Mutagenesis. Included in the concept of a synthetic protease is also any hybrid or chimeric protease, i.e. a protease which comprises a combination of partial amino acid sequences derived from at least two proteases. Gene shuffling is generally described in e.g. WO 95/22625 and WO 96/00343. Re-combination of protease genes can be made independently of the specific sequence of the parents by synthetic shuffling as described in Ness, J. E. et al, in Nature Biotechnology, Vol. 20 (12), pp. 1251-1255, 2002. Synthetic oligonucleotides degenerated in their DNA sequence to provide the possibility of all amino acids found in the set of parent proteases are designed and the genes assembled according to the reference. The shuffling can be carried out for the full length sequence or for only part of the sequence and then later combined with the rest of the gene to give a full length sequence. Two, three, four, five or all six of the the proteases designated Protease 10, 18, 11, 35, 08 and 22 (SEQ ID NOs: 2, 4, 6, 8, 10, and 21; in particular the mature parts thereof) are particular examples of such parent proteases which can be subjected to shuffling as described above, to provide additional proteases of the invention.

In further particular embodiments, the parent protease comprises, or consists of, respectively, the amino acid sequence specified, or an allelic variant thereof; or a fragment thereof that has protease activity.

In still further particular embodiments, the protease variant of the invention is not identical to: (i) amino acids 1-188 of SEQ ID NO: 2, amino acids 1-188 of SEQ ID NO: 4, amino acids 1-188 of SEQ ID NO: 6, amino acids 1-188 of SEQ ID NO: 8, and amino acids 1-188 of SEQ ID NO: 10; (ii) amino acids 1-188 of SEQ ID NO: 2; (iii) amino acids 1-188 of SEQ ID NO: 2 with the substitution T87A; (iv) amino acids 1-188 of SEQ ID NO: 4; (v) amino acids 1-188 of SEQ ID NO: 6; (vi) amino acids 1-188 of SEQ ID NO: 8; (vii) amino acids 1-188 of SEQ ID NO: 10; (viii) the protease derived from *Nocardiopsis dassonvillei* NRRL 18133; (ix) the protease having amino acids 1 to 188 of SEQ ID NO: 2 as disclosed in JP 2003284571-A; (x) the protease having the sequence entered in GENESEQP with no. ADF43564; (xi) the protease disclosed in DK patent application no. 2004 00969 as SEQ ID NO: 2, in particular the mature part thereof; (xii) the protease disclosed in DK patent application no. 2004 00969 as SEQ ID NO: 4, in particular the mature part thereof; (xiii) the protease disclosed in DK patent application no. 2004 00969 as SEQ ID NO: 6, in particular the mature part thereof; (xiv) the protease disclosed in DK patent application no. 2004 00969 as SEQ ID NO: 8, in particular the mature part thereof; (xv) the protease disclosed in DK patent application no. 2004 00969 as SEQ ID NO: 10, in particular the mature part thereof; (xvi) the protease disclosed in DK patent application no. 2004 00969 as SEQ ID NO: 12, in particular the mature part thereof; and/or (xvii) any prior art protease of a percentage of identity to SEQ ID NO: 2 of at least 60%.

Microorganism Taxonomy

Questions relating to taxonomy may be solved by consulting a taxonomy data base, such as the NCBI Taxonomy Browser which is available at the following internet site: ncbi.nlm.nih.gov/Taxonomy/taxonomyhome.html/, and/or by consulting Taxonomy handbooks. For the present purposes, the taxonomy is preferably according to the chapter: The road map to the Manual by G. M. Garrity & J. G. Holt in Bergey's Manual of Systematic Bacteriology, 2001, second edition, volume 1, David R. Bone, Richard W. Castenholz.

Amino Acid Homology

The present invention refers to proteases, viz. parent proteases, and/or protease variants, having a certain degree of identity to amino acids 1 to 188 of SEQ ID NO: 2, such parent and/or variant proteases being hereinafter designated "homologous proteases".

For purposes of the present invention the degree of identity between two amino acid sequences, as well as the degree of identity between two nucleotide sequences, is determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183: 63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Multiple alignments of protein sequences may be made using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680). Multiple alignment of DNA sequences may be done using the protein alignment as a template, replacing the amino acids with the corresponding codon from the DNA sequence.

In particular embodiments, the homologous protease has an amino acid sequence which has a degree of identity to amino acids 1 to 188 of SEQ ID NO: 2 of at least 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or of at least about 99%.

In alternative embodiments, the homologous protease has an amino acid sequence which has a degree of identity to SEQ ID NO: 2 of at least 50%, 51%, 52%, 53%, 54%, 55%, 56%, 57%, 58%, or at least 59%.

In another particular embodiment, the parent protease, and/or the protease variant, comprises a mature amino acid sequence which differs by no more than seventyfive, seventyfour, seventythree, seventytwo, seventyone, seventy, sixtynine, sixtyeight, sixtyseven, sixtysix, sixtyfive, sixtyfour, sixtythree, sixtytwo, sixtyone, sixty, fiftynine, fiftyeight, fiftyseven, fiftysix, fiftyfive, fiftyfour, fiftythree, fiftytwo, fiftyone, fifty, fortynine, fortyeight, fortyseven, fortysix, fortyfive, fortyfour, fortythree, fortytwo, fortyone, forty, thirtynine, thirtyeight, thirtyseven, thirtysix, thirtyfive, thirtyfour, thirtythree, thirtytwo, thirtyone, thirty, twentynine, twentyeight, twentyseven, twentysix, twentyfive, twentyfour, twentythree, twentytwo, twentyone, twenty, nineteen, eighteen, seventeen, sixteen, fifteen, fourteen, thirteen, twelve, eleven, ten, nine, eight, seven, six, five, four, three, by no more than two, or only by one amino acid(s) from the specified amino acid sequence, e.g. amino acids 1 to 188 of SEQ ID NO: 2.

In a still further particular embodiment, the parent protease, and/or the protease variant, comprises a mature amino acid sequence which differs by at least seventyfive, seventyfour, seventythree, seventytwo, seventyone, seventy, sixtynine, sixtyeight, sixtyseven, sixtysix, sixtyfive, sixtyfour, sixtythree, sixtytwo, sixtyone, sixty, fiftynine, fiftyeight, fiftyseven, fiftysix, fiftyfive, fiftyfour, fiftythree, fiftytwo, fiftyone, fifty, fortynine, fortyeight, fortyseven, fortysix, fortyfive, fortyfour, fortythree, fortytwo, fortyone, forty, thirtynine, thirtyeight, thirtyseven, thirtysix, thirtyfive, thirtyfour, thirtythree, thirtytwo, thirtyone, thirty, twentynine, twentyeight, twentyseven, twentysix, twentyfive, twentyfour, twentythree, twentytwo, twentyone, twenty, nineteen, eighteen, seventeen, sixteen, fifteen, fourteen, thirteen, twelve, eleven, ten, nine, eight, seven, six, five, four, three, by at least two, or by one amino acid(s) from the specified amino acid sequence, e.g. amino acids 1 to 188 of SEQ ID NO: 2.

Nucleic Acid Hybridization

In the alternative, homologous parent proteases, as well as variant proteases, may be defined as being encoded by a nucleic acid sequence which hybridizes under very low stringency conditions, preferably low stringency conditions, more preferably medium stringency conditions, more preferably medium-high stringency conditions, even more preferably high stringency conditions, and most preferably very high stringency conditions with nucleotides 900-1466, or 900-1463, of SEQ ID NO: 1, or a subsequence or a complementary strand thereof (J. Sambrook, E. F. Fritsch, and T. Maniatus, 1989, Molecular Cloning, A Laboratory Manual, 2d edition, Cold Spring Harbor, N.Y.). A subsequence may be at least 100 nucleotides, or at least 200, 300, 400, or at least 500 nucleotides. Moreover, the subsequence may encode a polypeptide fragment that has the relevant enzyme activity.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Position Numbering

In the present context, the basis for numbering positions is amino acids 1 to 188 of SEQ ID NO: 2, Protease 10, starting with A1 and ending with T188, see FIG. 1. A parent protease, as well as a variant protease, may comprise extensions as compared to SEQ ID NO: 2, i.e. in the N-terminal, and/or the C-terminal ends thereof. The amino acids of such extensions, if any, are to be numbered as is usual in the art, i.e. for a C-terminal extension: 189, 190, 191 and so forth, and for an N-terminal extension -1, -2, -3 and so forth.

Alterations, such as Substitutions, Deletions, Insertions

In the present context, the following are examples of various ways in which a protease variant can be designed or derived from a parent amino acid sequence: An amino acid can be substituted with another amino acid; an amino acid can be deleted; an amino acid can be inserted; as well as any combination of any number of such alterations.

For the present purposes, the term substitution is intended to include any number of any type of such alterations. This is a reasonable definition, because, for example, a deletion can be regarded as a substitution of an amino acid, AA, in a given position, nn, with nothing, ( ). Such substitution can be designated: AAnn( ). Likewise, an insertion of only one amino acid, BB, downstream an amino acid, M, in a given position, nn, can be designated: ( )nnaBB. And if two amino acids, BB and CC, are inserted downstream of amino acid AA in position nn, this substitution (combination of two substitutions) can be designated: ( )nnaBB+( )nnbCC, the thus created gaps between amino acids nn and nn+1 in the parent sequence being assigned lower case or subscript letters a, b, c etc. to the former position number, here nn. A similar numbering procedure is followed when aligning a new sequence to the multiple alignment of FIG. 1, in case of a gap being created by the alignment between amino acids nn and nn+1: Each position of the gap is assigned a number: nna, nnb etc. A comma (,) between substituents, as e.g. in the substitution T129E,D,Y,Q means "either or", i.e. that T129 is substituted with E, or D, or Y, or Q. A plus-sign (+) between substitutions, e.g. 129D+135P means "and", i.e. that these two single substitutions are combined in one and the same protease variant.

In the present context, the term "a" substitution" means at least one substitution. At least one means one or more, e.g. one, or two, or three, or four, or five, or six, or seven, or eight, or nine, or ten, or twelve, or fourteen, or fifteen, or sixteen, or eighteen, or twenty, or twentytwo or twentyfour, or twentyfive, or twenty eight, or thirty, and so on, to include in principle, any number of substitutions. The variants of the invention, however, still have to be, e.g., at least 60% identical to SEQ ID NO: 2, this percentage being determined by the above-mentioned program. The substitutions can be applied to any position encompassed by any region mentioned in claim 1, and variants comprising combinations of any number and type of such substitutions are also included. The term substitution as used herein also include deletions, as well as extensions, or insertions, that may add to the length of the sequence corresponding to amino acids 1 to 188 of SEQ ID NO: 2.

Furthermore, the term "a substitution" embraces a substitution into any one of the other nineteen natural amino acids, or into other amino acids, such as non-natural amino acids. For example, a substitution of amino acid T in position 22 includes each of the following substitutions: 22A, 22C, 22D, 22E, 22F, 22G, 22H, 22I, 22K, 22L, 22M, 22N, 22P, 22Q, 22R, 22S, 22V, 22W, and 22Y. This is, by the way, equivalent to the designation 22X, wherein X designates any amino acid. These substitutions can also be designated T22A, T22C, T22X, etc. The same applies by analogy to each and every position mentioned herein, to specifically include herein any one of such substitutions.

Identifying Corresponding Position Numbers

For each amino acid residue in each parent, or variant, protease of the invention, and/or for use according to the Invention, it is possible to directly and unambiguously assign an amino acid residue in the sequence of amino acids 1 to 188 of SEQ ID NO: 2 to which it corresponds. Corresponding residues are assigned the same number, by reference to the Protease 10 sequence.

As it appears from the numbering of FIG. 1, in conjunction with the numbering of the sequence listing, for each amino acid residue of each of the proteases Protease 10, Protease 18, Protease 11, Protease 35, Protease 08, and Protease 22, the corresponding amino acid residue in SEQ ID NO: 2 has the same number. This number is easily derivable from FIG. 1. At least in case of these six proteases, the number is the same as the number assigned to this amino acid residue in the sequence listing for the mature part of the respective protease.

For a given position in another protease—be it a parent or a variant protease—a corresponding position of SEQ ID NO: 2 can always be found, as follows:

The amino acid sequence of another parent protease, or, in turn, of a variant protease amino acid sequence, is designated SEQ-X. A position corresponding to position N of SEQ ID NO: 2 is found as follows: The parent or variant protease amino acid sequence SEQ-X is aligned with SEQ ID NO: 2 as specified above in the section entitled Amino Acid Homology. From the alignment, the position in sequence SEQ-X corresponding to position N of SEQ ID NO: 2 can be clearly and unambiguously derived, using the principles described below.

SEQ-X is the mature part of the protease in question. In the alternative, it may also include a signal peptide part, and/or a propeptide part, or it may be a fragment of the mature protease which has protease activity, e.g. a fragment of the same length as SEQ ID NO: 2, and/or it may be the fragment which extends from A1 to T188 when aligned with SEQ ID NO: 2 as described herein.

Region and Position

In the present context, the term region means at least one position of a parent protease amino acid sequence, the term position designating an amino acid residue of such amino acid sequence. In one embodiment, region means one or more successive positions of the parent protease amino acid sequence, e.g. one, two, three, four, five, six, seven, eight, etc., up to any number of consecutive positions of the sequence. Accordingly, a region may consist of one position only, or it may consist of any number of consecutive positions, such as, e.g., position no. 62 and 63; or position no. 111, 112, 113 and 114. For the present purposes, these two regions are designated 62-63, and 111-114, respectively. The boundaries of these regions or ranges are included in the region.

A region encompasses specifically each and every position it embraces. For example, region 111-114 specifically encompasses each of the positions 111, 112, 113, and 114. The same applies by analogy for the other regions mentioned herein.

Thermostability

For the present purposes, the term thermostable as applied in the context of a certain polypeptide, refers to the melting temperature, Tm, of such polypeptide, as determined using Differential Scanning Calorimetry (DSC) in 10 mM sodium phosphate, 50 mM sodium chloride, pH 7.0, using a constant scan rate of 1.5° C./min.

The following Tm's were determined under the above conditions: 76.5° C. (Protease 10), 83.0° C. (Protease 18), 78.3° C. (Protease 08), 76.6° C. (Protease 35), 73.7° C. (Protease 11), and 83.5° C. (Protease 22).

For a thermostable polypeptide, the Tm is at least 83.1° C. In particular embodiments, the Tm is at least 84, 85, 86, 87, 88, 89, 90, 91, 92, 93, 94, 95, 96, 97, 98, 99 or at least 100° C.

In the alternative, the term thermostable refers to a melting temperature of at least 73.8, or at least 76.7° C., or at least 78.4° C., preferably at least 74, 75, 76, 77, 78, 79, 80, 81, 82, or at least 83° C., still as determined using DSC at a pH of 7.0.

For the determination of Tm, a sample of the polypeptide with a purity of at least 90% (or 91, 92, 93, 94, 95, 96, 97, or 98%) as determined by SDS-PAGE may be used. Still further, the enzyme sample may have a concentration of between 0.5 and 2.5 mg/ml protein (or between 0.6 and 2.4, or between 0.7 and 2.2, or between 0.8 and 2.0 mg/ml protein), as determined from absorbance at 280 nm and based on an extinction coefficient calculated from the amino acid sequence of the enzyme in question.

The DSC takes place at the desired pH (e.g. pH 5.5, 7.0, 3.0, or 2.5) and with a constant heating rate, e.g. of 1, 1.5, 2, 3, 4, 5, 6, 7, 8, 9 or 10° C./min.

In a particular embodiment, the protease variant of the invention is thermostable, preferably more thermostable than the parent protease. In this context, preferred parent proteases are Protease 18, or Protease 10.

In another particular embodiment, a culture supernatant of the protease variant of the invention, appropriately diluted, exhibits a residual activity after incubation for four hours at 65° C. in a 0.2M $Na_2HPO_4$ buffer, titrated with 0.1M citric acid to i) pH 6.0, or ii) pH 4.0, of at least 20%, relative to an un-incubated (frozen) control, the activity being measured using the Protazyme AK assay at pH 8.5 and 37° C., as described in Example 2. In further particular embodiments, the residual activity is at least 25, 30, 35, 40, 45, 50, 55, 60, 65, 70, 75, or at least 77%.

Temperature Activity Profile

In a particular embodiment, the protease variant of the invention exhibits an amended temperature activity profile as compared to, e.g., Protease 10 (or Protease 18, Protease 11, Protease 35, or Protease 08). For example, the protease variant of the invention may exhibit a relative activity at pH 9 and 80° C. of at least 0.40, preferably at least 0.45, 0.50, 0.55, 0.60, 0.65, 0.70, 0.75, 0.80, 0.85, 0.90, or at least 0.95, the term "relative" referring to the maximum activity measured for the protease in question. For Protease 22, the activity is relative to the activity at 80° C. which is set to 1.000 (100%), and for Protease 10, the activity at 70° C. is set to 1.000 (100%), see Example 3. As another example, the protease variant of the invention exhibits a relative activity at pH 9 and 90° C. of at least 0.10, preferably at least 0.15, 0.20, 0.25, 0.30, or of at least 0.35. In a particular embodiment, the protease activity is measured using the Protazyme AK assay of Example 1.

Low-Allergenic Variants

In a specific embodiment, the protease variants of the present invention are (also) low-allergenic variants, designed to invoke a reduced immunological response when exposed to animals, including man. The term immunological response is to be understood as any reaction by the immune system of an animal exposed to the protease variant. One type of immunological response is an allergic response leading to increased levels of IgE in the exposed animal. Low-allergenic variants may be prepared using techniques known in the art. For example the protease variant may be conjugated with polymer moieties shielding portions or epitopes of the protease variant involved in an immunological response. Conjugation with polymers may involve in vitro chemical coupling of polymer to the protease variant, e.g. as described in WO 96/17929, WO 98/30682, WO 98/35026, and/or WO 99/00489. Conjugation may in addition or alternatively thereto involve in vivo coupling of polymers to the protease variant. Such conjugation may be achieved by genetic engineering of the nucleotide sequence encoding the protease variant, inserting consensus sequences encoding additional glycosylation sites in the protease variant and expressing the protease variant in a host capable of glycosylating the protease variant, see e.g. WO 00/26354. Another way of providing low-allergenic variants is genetic engineering of the nucleotide sequence encoding the protease variant so as to cause the protease variants to self-oligomerize, effecting that protease variant monomers may shield the epitopes of other protease variant monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the protease variant by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

Nucleic Acid Sequences and Constructs

The present invention also relates to nucleic acid sequences comprising a nucleic acid sequence which encodes a protease variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into the parent protease coding sequence or a subsequence thereof, wherein the mutant nucleic acid sequence encodes a variant protease. The introduction of a mutation into the nucleic acid sequence to exchange one nucleotide for another nucleotide may be accomplished by site-directed mutagenesis using any of the methods known in the art, e.g. by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the protease enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent protease in question. This may, e.g., be advantageous when certain regions of the enzyme have been identified to be of particular importance for a given property of the enzyme.

Alternative methods for providing variants of the invention include gene shuffling e.g. as described in WO 95/22625 or in WO 96/00343, and the consensus derivation process as described in EP 897985 (see the section "Parent Protease" for more details).

In particular embodiments, the nucleic acid sequence of the invention is not identical to: (i) Nucleotides 900-1466, or 900-1463, of SEQ ID NO: 1, nucleotides 499-1062 of SEQ ID NO: 3, nucleotides 496-1059 of SEQ ID NO: 5, nucleotides 496-1059 of SEQ ID NO: 7, and nucleotides 502-1065 of SEQ ID NO: 9; (ii) nucleotides 900-1466 of SEQ ID NO: 1; (iii) nucleotides 900-1463 of SEQ ID NO: 1; (iv) nucleotides 900-1463 of SEQ ID NO: 1 as disclosed in DK 1996 00013; (v) nucleotides 499-1062 of SEQ ID NO: 3; (vi) nucleotides 496-1059 of SEQ ID NO: 5; (vii) nucleotides 496-1059 of SEQ ID NO: 7; (viii) nucleotides 502-1065 of SEQ ID NO: 9; (xi) the nucleic acid sequence encoding the mature peptide part of the protease derived from *Nocardiopsis dassonvillei* NRRL 18133; (x) the nucleic acid sequence having SEQ ID NO: 1 as disclosed in JP 2003284571-A; (xi) the nucleic acid sequence GENESEQN no. ADF43563; (xii) the nucleic acid sequence disclosed in DK patent application no. 2004 00969 as SEQ ID NO: 1, in particular the mature peptide encoding part thereof; (xiii) the nucleic acid sequencep disclosed in DK patent application no. 2004 00969 as SEQ ID NO: 3, in particular the mature peptide encoding part thereof; (xiv) the nucleic acid sequence disclosed in DK patent application no. 2004 00969 as SEQ ID NO: 5, in particular the mature peptide encoding part thereof; (xv) the nucleic acid sequence disclosed in DK patent application no. 2004 00969 as SEQ ID NO: 7, in particular the mature peptide encoding part thereof; (xvi) the nucleic acid sequence disclosed in DK patent application no. 2004 00969 as SEQ ID NO: 9, in particular the mature peptide encoding part thereof; (xvii) the nucleic acid sequence disclosed in DK patent application no. 2004 00969 as SEQ ID NO: 11, in particular the mature peptide encoding part thereof; and/or (xviii) nucleic acid sequences encoding any prior art proteases of at least 60% identity to amino acids 1 to 188 of SEQ ID NO: 2.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

Expression Vector

A nucleic acid sequence encoding a protease variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a protease variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The protease variant may also be co-expressed together with at least one other enzyme of animal feed interest, such as an alpha-amylase, a phytase, a galactanase, a xylanase, an endoglucanase, an endo-1,3(4)-beta-glucanase, an alpha-galactosidase, and/or a protease. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The protease variant may also be expressed as a fusion protein, i.e. that the gene encoding the protease variant has been fused in frame to the gene encoding another protein. This protein may be another enzyme or a functional domain from another enzyme.

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote cell, such as an animal, a mammalian, an insect, a plant, or a fungal cell. Preferred animal cells are non-human animal cells.

In a preferred embodiment, the host cell is a fungal cell, or a yeast cell, such as a *Candida, Hansenula, Kluyveromyces, Pichia, Saccharomyces, Schizosaccharomyces*, or *Yarrowia* cell. The fungal host cell may be a filamentous fungal cell, such as a cell of a species of, but not limited to, *Acremonium, Aspergillus, Fusarium, Humicola, Mucor, Myceliophthora, Neurospora, Penicillium, Thielavia, Tolypocladium*, or *Trichoderma*. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*, or a *Streptomyces* cell, such as *Streptomyces lividans* or *Streptomyces murinus*, or a *Nocardiopsis* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus*, and *Enterococcus*.

Methods of Production

The present invention also relates to methods for producing a protease variant of the present invention comprising (a) cultivating a host cell under conditions conducive for production of the protease variant; and (b) recovering the protease variant.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the protease is secreted into the nutrient medium, it can be recovered directly from the medium. If it is not secreted, it can be recovered from cell lysates.

The resulting protease may be recovered by methods known in the art. For example, it can be recovered from the nutrient medium by conventional procedures including, but not limited to, centrifugation, filtration, extraction, spray-drying, evaporation, or precipitation.

The proteases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an anti-nutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca*, *Lolium*, temperate grass, such as Agrostis, and cereals, e.g., wheat, oats, rye, barley, rice, sorghum, triticale (stabilized hybrid of wheat (*Triticum*) and rye (*Secale*), and maize (corn). Examples of dicot plants are tobacco, legumes, such as sunflower (*Helianthus*), cotton (*Gossypium*), lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants.

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants. Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, Plant Physiology 86: 506.

For constitutive expression, the following promoters may be used: The 35S-CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675-689.; Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or alterations in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are generally preferred for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21:415428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a protease variant of the present invention under conditions conducive for production of the protease variant; and (b) recovering the protease variant.

Animals as Expression Hosts

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a protease variant of the present invention so as to express and produce the protease variant. The protease variant may be recovered from the animal, e.g. from the milk of female animals, or it may be expressed to the benefit of the animal itself, e.g. to assist the animal's digestion. Examples of animals are mentioned below in the section headed Animal Feed and Animal Feed Additives.

To produce a transgenic animal with a view to recovering the protease variant from the milk of the animal, a gene encoding the protease variant may be inserted into the fertilized eggs of an animal in question, e.g. by use of a transgene expression vector which comprises a suitable milk protein promoter, and the gene encoding the protease variant. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The protease variant may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the protease variant, the transgene may be operably linked to a first regulatory sequence for salivary gland specific expression of the protease variant, as disclosed in WO 2000064247.

Animal Feed and Animal Feed Additives

For the present purposes, the term animal includes all animals, including human beings. In a particular embodiment, the protease variants and compositions of the invention can be used as a feed additive for non-human animals. Examples of animals are non-ruminants, and ruminants, such as sheep, goats, horses, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns)).

The term feed or feed composition means any compound, preparation, mixture, or composition suitable for, or intended for intake by an animal. The feed can be fed to the animal before, after, or simultaneously with the diet. The latter is preferred.

The composition of the invention, when intended for addition to animal feed, may be designated an animal feed additive. Such additive always comprises the protease variant in question, preferably in the form of stabilized liquid or dry compositions. The additive may comprise other components or ingredients of animal feed. The so-called pre-mixes for animal feed are particular examples of such animal feed additives. Pre-mixes may contain the enzyme(s) in question, and in addition at least one vitamin and/or at least one mineral.

Accordingly, in a particular embodiment, in addition to the component polypeptides, the composition of the invention may comprise or contain at least one fat-soluble vitamin, and/or at least one water-soluble vitamin, and/or at least one trace mineral. Also at least one macro mineral may be included.

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

Further, optional, feed-additive ingredients are colouring agents, e.g. carotenoids such as beta-carotene, astaxanthin, and lutein; aroma compounds; stabilizers; polyunsaturated fatty acids; reactive oxygen generating species; antimicrobial peptides; and/or at least one additional enzyme.

Additional enzyme components of the invention include at least one polypeptide having amylase, preferably alpha-amylase, activity, and/or at least one polypeptide having xylanase activity; and/or at least one polypeptide having endoglucanase activity; and/or at least one polypeptide having endo-1, 3(4)-beta-glucanase activity; and/or at least one polypeptide having phytase activity; and/or at least one polypeptide having galactanase activity; and/or at least one polypeptide having alpha-galactosidase activity; and/or at least one other polypeptide having protease activity (EC 3.4.-.- - ); and/or at least one polypeptide having phospholipase A1 (EC 3.1.1.32), phospholipase A2 (EC 3.1.1.4), lysophospholipase (EC 3.1.1.5), phospholipase C (EC 3.1.4.3), and/or phospholipase D (EC 3.1.4.4) activity.

Alpha-amylase activity can be measured as is known in the art, e.g. using a starch-based substrate.

Xylanase activity can be measured using any assay, in which a substrate is employed, that includes 1,4-beta-D-xylosidic endo-linkages in xylans. Different types of substrates are available for the determination of xylanase activity e.g. Xylazyme cross-linked arabinoxylan tablets (from Mega-Zyme), or insoluble powder dispersions and solutions of azo-dyed arabinoxylan.

Endoglucanase activity can be determined using any endoglucanase assay known in the art. For example, various cellulose- or beta-glucan-containing substrates can be applied. An endoglucanase assay may use AZCL-Barley beta-Glucan, or preferably (1) AZCL-HE-Cellulose, or (2) Azo-CM-cellulose as a substrate. In both cases, the degradation of the substrate is followed spectrophotometrically at $OD_{595}$ (see the Megazyme method for AZCL-polysaccharides for the assay of endo-hydrolases at megazyme.com/booklets/AZCLPOL.pdf.

Endo-1,3(4)-beta-glucanase activity can be determined using any endo-1,3(4)-beta-glucanase assay known in the art.

A preferred substrate for endo-1,3(4)-beta-glucanase activity measurements is a cross-linked azo-coloured beta-glucan Barley substrate, wherein the measurements are based on spectrophotometric determination principles.

Phytase activity can be measured using any suitable assay, e.g. the FYT assay described in Example 4 of WO 98/28408.

Galactanase can be assayed e.g. with AZCL galactan from Megazyme, and alpha-galactosidase can be assayed e.g. with pNP-alpha-galactoside.

For assaying these enzyme activities the assay-pH and the assay-temperature are to be adapted to the enzyme in question (preferably a pH close to the optimum pH, and a temperature close to the optimum temperature). A preferred assay pH is in the range of 2-10, preferably 3-9, more preferably pH 3 or 4 or 5 or 6 or 7 or 8, for example pH 3 or pH 7. A preferred assay temperature is in the range of 20-90° C., preferably 30-90° C., more preferably 40-80° C., even more preferably 40-70° C., preferably 40 or 45 or 50° C. The enzyme activity is defined by reference to appropriate blinds, e.g. a buffer blind.

Examples of antimicrobial peptides (AMP's) are CAP18, Leucocin A, Tritrpticin, Pro-tegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat and water soluble vitamins, as well as trace minerals form part of a so-called premix intended for addition to the feed, whereas macro minerals are usually separately added to the feed. A premix enriched with a protease of the invention, is an example of an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg. WO 01/58275 corresponds to U.S. Ser. No. 09/779334 which is hereby incorporated by reference.

An animal feed composition according to the invention has a crude protein content of 50-800 g/kg, and furthermore comprises at least one protease variant as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or, in a particular embodiment, it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 040% soybean meal; and/or 0-25%, preferably 0-10%, fish meal; 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease variant should of course be applied in an effective amount, i.e. in an amount adequate for improving solubilisation and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease enzyme protein per kg feed (ppm).

For determining mg enzyme protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg enzyme protein per kg feed is calculated.

The same principles apply for determining mg enzyme protein in feed additives. Of course, if a sample is available of the protease used for preparing the feed additive or the feed, the specific activity is determined from this sample (no need to purify the protease from the feed composition or the additive).

Detergent Compositions

The protease variant of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease variant of the invention. The detergent additive as well as the detergent composition may comprise one or more other enzymes such as another protease, such as alkaline proteases from Bacillus, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym Thermomyces), e.g. from *H. lanuginosa* (*T. lanuginosus*) as described in EP 258068 and EP 305216 or from *H. insolens* as described in WO 96/13580, a Pseudomonas lipase, e.g. from *P. alcaligenes* or *P. pseudoalcaligenes* (EP 218272), *P. cepacia* (EP 331376), *P. stutzeri* (GB 1,372, 034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S).

Suitable amylases (alpha- and/or beta-) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839. Examples of useful amylases are the variants described in WO 94/02597, WO 94/18314, WO 95/26397, WO 96/23873, WO 97/43424, WO 00/60060, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are Natalase™, Supramyl™, Stainzyme™, Duramyl™, Termamyl™, Fungamyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495257, EP 531372, WO 96/11262, WO 96/29397, WO 98/08940. Other examples are cellulase variants such as those described in WO 94/07998, EP 0 531 315, U.S. Pat. Nos. 5,457,046, 5,686,593, 5,763, 254, WO 95/24471, WO 98/12307 and WO 99/01544. Commercially available cellulases include Celluzyme™, and Carezyme™ (Novozymes A/S), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liqour, preferably 0.05-5 mg of enzyme protein per liter of wash liqour, in particular 0.1-1 mg of enzyme protein per liter of wash liqour.

The enzyme of the invention may additionally be incorporated in the detergent formulations disclosed in WO 97/07202.

Method for Generating Protease Variants

The invention also relates to a method for generating a protease variant of an improved property, the method comprising the following steps:

(a) selecting a parent protease of at least 60% identity to amino acids 1 to 188 of SEQ ID NO: 2;

(b) establishing a 3D structure of the parent protease by homology modelling using the FIG. 2 structure as a model; and/or aligning the parent protease according to the alignment of FIG. 1;

(c) proposing at least one amino acid substitution, e.g. by:
  (i) subjecting the 3D structure of (b) to MD simulations at increased temperatures, and identifying regions in the amino acid sequence of the parent protease of high mobility (isotropic fluctuations);
  (ii) introducing disulfid bridges by way of cysteine substitutions (C-C);
  (iii) introducing proline substitutions (P);
  (iv) replacing exposed neutral amino acid residues with negatively charged amino acid residues (E,D);
  (v) replacing exposed neutral amino acid residues with positively charged amino acid residues (R,K);
  (vi) replacing small amino acid residues inside the protein with bulkier amino acid residues (W);
  (vii) comparing by homology alignment and/or homology modelling according to step (c)(i) at least two related parent proteases and transferring amino acid residue differences inbetween these protease backbones, preferably from a backbone having the improved property to a backbone not having this improved property;

(d) preparing a DNA sequence encoding the parent protease but for inclusion of a DNA codon of the at least one amino acid substitution proposed in steps (c)(ii)-(c)(vii), or subjecting the parent DNA sequence to random mutagenesis, targeting at least one of the regions identified in step (c)(i);

(e) expressing the DNA sequence obtained in step (d) in a host cell, and (h) selecting a host cell expressing a protease variant with an improved property.

The invention furthermore relates to a method for producing a protease variant obtainable or obtained by the method of generating protease variants described above, comprising (a) cultivating the host cell to produce a supernatant comprising the variant; and (b) recovering the variant.

The invention also relates to isolated nucleic acid sequences comprising a nucleic acid sequence which encodes the protease variant obtainable according to this method, as well as methods for producing it by (a) cultivating the host cell to produce a supernatant comprising the variant; and (b) recovering the variant; a transgenic plant, or plant part, capable of expressing it; transgenic, non-human animals, or products, or elements thereof, being capable of expressing it; animal feeds, as well as animal feed additives, comprising it; methods for improving the nutritional value of an animal feed by use thereof; methods for the treatment of proteins, such as vegetable proteins, by use thereof; as well s the use thereof (i) in animal feed; (ii) in the preparation of animal feed; (iii) for improving the nutritional value of animal feed; and/or (iv) for the treatment of proteins; and/or in detergents.

Alternative Embodiment

In an alternative embodiment, the term "alteration" is used instead of "substitution" as the general term for amendments in the protease molecule. This alternative embodiment includes each of the claims formulated as exemplified below for claim 1, and also specifically includes everything what is stated herein, e.g. definitions (other than the definition of substitution), i.e. the various aspects, particular embodiments etc.

A variant of a parent protease, comprising an alteration in at least one position of at least one region selected from the group of regions consisting of:

6-18; 22-28; 32-39; 42-58; 62-63; 66-76; 78-100; 103-106; 111-114; 118-131; 134-136; 139-141; 144-151; 155-156; 160-176; 179-181; and 184-188; wherein (a) the alteration(s) are independently (i) an insertion of an amino acid immediately downstream of the position, (ii) a deletion of the amino acid which occupies the position, and/or (iii) a substitution of the amino acid which occupies the position;

(b) the variant has protease activity; and (c) each position corresponds to a position of SEQ ID NO: 2, preferably amino acids 1 to 188 thereof; and (d) the variant has a percentage of identity to SEQ ID NO: 2, preferably to amino acids 1 to 188 thereof, of at least 60%.

The term "polypeptide variant", "protein variant", "enzyme variant", "protease variant" or simply "variant" refers to a polypeptide of the invention comprising one or more alteration(s), such as substitution(s), insertion(s), deletion(s), and/or truncation(s) of one or more specific amino acid residue(s) in one or more specific position(s) in the polypeptide.

The term "parent polypeptide", "parent protein", "parent enzyme", "standard enzyme", "parent protease" or simply "parent" refers to the polypeptide on which the variant was based. This term also refers to the polypeptide with which a variant is compared and aligned.

The term "randomized library", "variant library", or simply "library" refers to a library of variant polypeptides. Diversity in the variant library can be generated via mutagenesis of the genes encoding the variants at the DNA triplet level, such that individual codons are variegated e.g. by using primers of partially randomized sequence in a PCR reaction. Several techniques have been described, by which one can create a diverse combinatorial library by variegating several nucleotide positions in a gene and recombining them, for instance where these positions are too far apart to be covered by a single (spiked or doped) oligonucleotide primer. These techniques include the use of in vivo recombination of the individually diversified gene segments as described in WO 97/07205 on page 3, lines 8 to 29 (Novozymes A/S). They also include the use of DNA shuffling techniques to create a library of full length genes, wherein several gene segments are combined, and wherein each segment may be diversified e.g. by spiked mutagenesis (Stemmer, Nature 370, pp. 389-391, 1994 and U.S. Pat. Nos. 5,811,238; 5,605,793; and 5,830,721); One can use a gene encoding a protein "backbone" (wildtype parent polypeptide) as a template polynucleotide, and combine this with one or more single or double-stranded oligonucleotides as described in WO 98/41623 and in WO 98/41622 (Novozymes A/S). The single-stranded oligonucleotides could be partially randomized during synthesis. The double-stranded oligonucleotides could be PCR products incorporating diversity in a specific region. In both cases, one can dilute the diversity with corresponding segments encoding the sequence of the backbone protein in order to limit the average number of changes that are introduced.

Methods have also been established for designing the ratios of nucleotide mixtures (A; C; T; G) to be inserted in specific codon positions during oligo- or polynucleotide synthesis, so as to introduce a bias in order to approximate a desired frequency distribution towards a set of one or more desired amino acids that will be encoded by the particular codons. It may be of interest to produce a variant library, that comprises permutations of a number of known amino acid modifications in different locations in the primary sequence of the polypeptide. These could be introduced post-translationally or by chemical modification sites, or they could be introduced through mutations in the encoding genes. The modifications by themselves may previously have been proven beneficial for one reason or another (e.g. decreasing antigenicity, or improving specific activity, performance, stability, or other characteristics). In such instances, it may be desirable first to create a library of diverse combinations of known sequences. For example, if twelve individual mutations are known, one could combine (at least) twelve segments of the parent protein encoding gene, wherein each segment is present in two forms: one with, and one without the desired mutation. By varying the relative amounts of those segments, one could design a library (of size 212) for which the average number of mutations per gene can be predicted. This can be a useful way of combining mutations, that by themselves give some, but not sufficient effect, without resorting to very large libraries, as is often the case when using 'spiked mutagenesis'. Another way to combine these 'known mutations' could be by using family shuffling of oligomeric DNA encoding the known mutations with fragments of the full length wild type sequence.

In describing the various variants produced or contemplated according to the invention, a number of nomenclatures and conventions are used which are described in detail below. A frame of reference is first defined by aligning the variant polypeptide with a parent enzyme. A preferred parent enzyme is Protease 10 (amino acids 1 to 188 of SEQ ID NO: 2). Thereby a number of alterations will be defined in relation to the amino acid sequence of amino acids 1 to 188 of SEQ ID NO: 2.

A substitution in a variant is indicated as:

Original amino acid—position—substituted amino acid;

The three or one letter codes are used, including the codes Xaa and X to indicate any amino acid residue. Accordingly, the notation "T82S" or "Thr82Ser" means, that the variant comprises a substitution of threonine with serine in the variant amino acid position corresponding to the amino acid in position 82 in the parent enzyme, when the two are aligned as indicated above.

Where the original amino acid residue may be any amino acid residue, a short hand notation may at times be used indicating only the position, and the substituted amino acid, for example:

Position—substituted amino acid; or "82S",

Such a notation is particular relevant in connection with modification(s) in a series of homologous polypeptides.

Similarly when the identity of the substituting amino acid residue(s) is immaterial:

Original amino acid—position; or "T82"

When both the original amino acid(s) and substituted amino acid(s) may be any amino acid, then only the position is indicated, e.g.: "82".

When the original amino acid(s) and/or substituted amino acid(s) may comprise more than one, but not all amino acid(s), then the amino acids are listed separated by commas:

Original amino acids—position no.—substituted amino acids; or "T10E, D, Y".

A number of examples of this nomenclature are listed below:

The substitution of threonine for histidine in position 91 is designated as: "His91Thr" or "H91T"; or the substitution of any amino acid residue acid for histidine in position 91 is designated as: "His91Xaa" or "H91X" or "His91" or "H91".

For a modification where the original amino acid(s) and/or substituted amino acid(s) may comprise more than one, but not all amino acid(s), the substitution of glutamic acid, aspartic acid, or tyrosine for threonine in position 10:

"Thr10Glu, Asp, Tyr" or "T10E, D, Y"; which indicates the specific variants: "T10E", "T10D", and "T10Y".

A deletion of glycine in position 26 will be indicated by: "Gly26*" or "G26*"

Correspondingly, the deletion of more than one amino acid residue, such as the deletion of glycine and glutamine in positions 26 and 27 will be designated "Gly26*+Gln27*" or "G26*+Q27*"

The insertion of an additional amino acid residue such as e.g. a lysine after G26 is indicated by: "Gly26GlyLys" or "G26GK"; or, when more than one amino acid residue is inserted, such as e.g. a Lys, and Ala after G26 this will be indicated as: "Gly26GlyLysAla" or "G26GKA".

In such cases the inserted amino acid residue(s) are numbered by the addition of lower case letters to the position number of the amino acid residue preceding the inserted amino acid residue(s). In the above example the sequences would thus be:

| Parent: | | Variant: | |
|---|---|---|---|
| 26 | 26 | 26a | 26b |
| G | G | K | A |

In cases where an amino acid residue identical to the existing amino acid residue is inserted, it is clear that degeneracy in the nomenclature arises. If for example a glycine is inserted after the glycine in the above example this would be indicated by "G26GG".

Given that an alanine were present in position 25, the same actual change could just as well be indicated as "A25AG":

| | Parent: | | Variant: | | |
|---|---|---|---|---|---|
| Numbering I: | 25 | 26 | 25 | 26 | 26a |
| Sequence: | A | G | A | G | G |
| Numbering II: | | | 25 | 25a | 26 |

Such instances will be apparent to the skilled person, and the indication "G26GG" and corresponding indications for this type of insertions is thus meant to comprise such equivalent degenerate indications.

By analogy, if amino acid sequence segments are repeated in the parent polypeptide and/or in the variant, it will be apparent to the skilled person that equivalent degenerate indications are comprised, also when other alterations than insertions are listed such as deletions and/or substitutions. For instance, the deletion of two consecutive amino acids "AG" in the sequence "AGAG" from position 194-197, may be written as "A194*+G1956*" or "A196*+G197*":

| | Parent: | | | | Variant: | |
|---|---|---|---|---|---|---|
| Numbering I: | 194 | 195 | 196 | 197 | 194 | 195 |
| Sequence: | A | G | A | G | A | G |
| Numbering II: | | | | | 196 | 197 |

Variants comprising multiple modifications are separated by pluses, e.g.:

"Arg170Tyr+Gly195Glu" or "R170Y+G195E", representing modifications in positions 170 and 195 substituting tyrosine and glutamic acid for arginine and glycine, respectively. Thus, "Tyr167Gly, Ala, Ser, Thr+Arg170Gly, Ala, Ser, Thr" designates the following variants:

"Tyr167Gly+Arg170Gly", "Tyr167Gly+Arg170Ala",
"Tyr167Gly+Arg170Ser", "Tyr167Gly+Arg170Thr",
"Tyr167Ala+Arg170Gly", "Tyr167Ala+Arg170Ala",
"Tyr167Ala+Arg170Ser", "Tyr167Ala+Arg170Thr",
"Tyr167Ser+Arg170Gly", "Tyr167Ser+Arg170Ala",
"Tyr167Ser+Arg170Ser", "Tyr167Ser+Arg170Thr",
"Tyr167Thr+Arg170Gly", "Tyr167Thr+Arg170Ala",
"Tyr167Thr+Arg170Ser", and "Tyr167Thr+Arg170Thr".

This nomenclature is particular relevant relating to modifications aimed at substituting, inserting or deleting amino acid residues having specific common properties, such modifications are referred to as conservative amino acid modification(s).

Various Embodiments

These are additional various embodiments of the invention:

The variant of any one of claims 1-16 and 18-20 which comprises at least one of the following substitutions: T10Y, A24S, V51T, E53Q, T82Q, A86Q, T87S, I96A, G118N, S122R, N130S, L186I.

The variant of any one of claims 1-16 and 18-19 which comprises at least one of the following substitutions: R38T; Q42G, P; R49T, Q; Q54N, R; A89S, T; H91S, T; N92S; S99A, Q; A120T; E125Q; T129Y,Q; M131L; T135N; Y147F; N151S; R165S; T166V, F; F171Y; V179I, L; preferably at least one of the following substitutions: R38T; N92S; A120T; E125Q; M131L; T135N; Y147F; N151S; R165S; and/or F171Y.

The variant of any one of claims 1-19 which comprises at least one of the following substitutions: A25S, T44S, A62S, P95A, V100I, I114V, T176N, N180S, V184L, R185T.

The variant of any one of claims 1-20 which has amended properties, such as an improved thermostability and/or a higher or lower optimum temperature, such as a Tm of at least 83.1° C. as measured by DSC in 10 mM sodium phosphate, 50 mM sodium chloride, pH 7.0.

The variant of any one of claims 1-20 which derives from a strain of the genus *Nocardiopsis*, such as *Nocardiopsis alba*, *Nocardiopsis antarctica*, *Nocardiopsis prasina*, *Nocardiopsis composta*, *Nocardiopsis dassonvillei*, *Nocardiopsis exhalans*, *Nocardiopsis halophila*, *Nocardiopsis halotolerans*, *Nocardiopsis kunsanensis*, *Nocardiopsis listeri*, *Nocardiopsis lucentensis*, *Nocardiopsis metallicus*, *Nocardiopsis* sp., *Nocardiopsis synnemataformans*, *Nocardiopsis trehalosi*, *Nocardiopsis tropica*, *Nocardiopsis umidischolae*, or *Nocardiopsis xinjiangensis*, preferably *Nocardiopsis alba* DSM 15647, *Nocardiopsis dassonvillei* NRRL 18133, *Nocardiopsis dassonvillei* subsp. *dassonvillei* DSM 43235, *Nocardiopsis prasina* DSM 15648, *Nocardiopsis prasina* DSM 15649, *Nocardiopsis* sp. NRRL 18262, most preferably *Nocardiopsis* sp. FERM P-18676.

A composition, such as an animal feed additive, comprising at least one protease variant of any of claims 1-20, and
(a) at least one fat soluble vitamin;
(b) at least one water soluble vitamin; and/or
(c) at least one trace mineral, optionally further comprising at least one enzyme selected from the following group of enzymes: amylases, galactanases, alpha-galactosidases, xylanases, endoglucanases, endo-1,3(4)-beta-glucanases, phytases, phospholipases, and other proteases; if desired also comprising at least one amylase, and/or phospholipase.

The present invention is further described by the following examples which should not be construed as limiting the scope of the invention.

EXAMPLES

Example 1

Protease Assays pNA assay
  pNA substrate: Suc-MPF-pNA (Bachem L-1400).
  Temperature: Room temperature (25° C.)
  Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0, 11.0, and 12.0 with HCl or NaOH.

20 µl protease (diluted in 0.01% Triton X-100) is mixed with 100 µl assay buffer. The assay is started by adding 100 µl pNA substrate (50 mg dissolved in 1.0 ml DMSO and further diluted 45× with 0.01% Triton X-100). The increase in $OD_{405}$ is monitored as a measure of the protease activity.

Protazyme AK Assay
  Substrate: Protazyme AK tablet (cross-linked and dyed casein; from Megazyme)
  Temperature: controlled (assay temperature).
  Assay buffers: 199 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0 and 11.0 with HCl or NaOH.

A Protazyme AK tablet is suspended in 2.0 ml 0.01% Triton X-100 by gentle stirring. 500 µl of this suspension and 500 µl assay buffer are mixed in an Eppendorf tube and placed on ice. 20 µl protease sample (diluted in 0.01% Triton X-100) is added. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an icecold centrifuge for a few minutes and 200 µl supernatant is transferred to a microtiter plate. $OD_{650}$ is read as a measure of protease activity. A buffer blind is included in the assay (instead of enzyme).

Example 2

Preparation and Testing of Protease Variants

Four protease variants comprising the amino acid sequence of amino acids 1 to 188 of SEQ ID NO: 2 (Protease 10) with the single substitutions N47D, T127R, N92K, and Q54R, respectively, were prepared as described below for variant N47D.

Site directed mutagenesis was carried out using the Megaprimer method as described by Sarkar and Sommer, 1990 (BioTechniques 8: 404-407).

The N47D variant was constructed by use of the following primers, of which primer R10WT-CL29 (SEQ ID NO: 11) is gene specific, and primer RSWT126 (SEQ ID NO: 12) mutagenic:

```
                                       (SEQ ID NO: 11)
R10WT-CL29: 5' CCGATTATGGAGCGGATTGAACATGCG 3'

(SEQ ID NO: 12)
RSWT126:    5' GTGACCATCGGCGACGGCAGGGGCGTCTTCG 3',
``` to amplify by PCR an approximately 469 bp DNA fragment from the construct described below.

The Protease 10 DNA construct used for the above amplification was an expression cassette (SEQ ID NO: 13) for incorporation into the genome of *Bacillus subtilis*. The construct contains a fusion of DNA encoding the signal sequence and the gene encoding the pro- and the mature protein of Protease 10 (SEQ ID NO: 14), a promoter construction, and also the cat gene conferring resistance towards chloramphenicol. To facilitate the integration into the genome by homologous recombination, flanking regions of around 3 kb of a *Bacillus subtilis* endogenous genes were incorporated upstream and downstream of the Protease 10 encoding sequence.

The resulting 469 bp fragment was purified from an agarose gel (Sigma Aldrich cat. no. A6877) and used as a Megaprimer together with primer R10WT-CL39N (SEQ ID NO: 15) in a second PCR carried out on the same template.

```
R10WT-CL39N:
                                       (SEQ ID NO: 15)
    5' GGAGCTCTGAAAAAAAGGAGAGGATAAAGAATGAA 3'.
```

The full construction of approximately 10 kb is made in vitro by long range PCR, using the oligonucleotides R10WT-CL28N (SEQ ID NO: 16), R10WT-CL28C (SEQ ID NO: 17), and the Expand Long Template PCR System from Roche Applied Science (cat no. 11759060), according to the suppliers manual.

```
                                              (SEQ ID NO: 16)
R10WT-CL28N:    5' GCGTTCCGATAATCGCGGTGACAATGCCG 3'

(SEQ ID NO: 17)
R10WT-CL28C:    5' TTCATGAGTCTGCGCCCTGAGATCCTCTG 3'
```

The resulting approximately 1.2 kb fragment was purified and combined in a new PCR reaction using Expand Long Template PCR System with the flanking fragments of the construction made by two PCR reactions using R10WT-2C-rev (SEQ ID NO: 18) and R10WT-CL28C (SEQ ID NO: 17); and RSWT001 (SEQ ID NO: 19) and R10WT-CL28N (SEQ ID NO: 16) as primer sets. The resulting 10 kb fragment can be amplified using the R10WT-CL28N (SEQ ID NO: 16) and R10WT-CL28C (SEQ ID NO: 17) primers, to increase the number of transformants.

```
RWT-2C-rev:
                                              (SEQ ID NO: 18)
5' TAATCGCATGTTCAATCCGCTCCATAATCG 3'

RSWT001:
                                              (SEQ ID NO: 19)
5' CCCAACGGTTTCTTCATTCTTTATCCTCTCCTTTTTTTCAGAGC 3'
```

Competent cells of an amylase- and protease-low strain of *Bacillus subtilis* (such as strain SHA273 described in WO92/11357 and WO95/10603) were transformed with the respective resulting PCR fragments, and chlorampenicol resistant transformants were selected and checked by DNA sequencing to verify the presence of the correct mutation on the genome.

Cells of *Bacillus subtilis* harbouring constructs encoding Protease 10 and each of the four variants thereof were used to incubate shakeflasks containing a rich media (PS-1: 100 g/L Sucrose (Danisco cat. no. 109-0429), 40 g/L crust soy, 10 g/L Na$_2$HPO$_4$.12H$_2$O (Merck cat. no. 6579), 0.1 ml/L Pluronic PE 6100 (BASF 102-3098)), and cultivation took place for five days at 30° C. under vigorous shaking.

After cultivation, the supernatants were diluted four times in a 0.2M Na$_2$HPO$_4$ buffer, titrated with a 0.1M citric acid to either pH 4.0 or pH 6.0, and split in two. One half was incubated for four hours at 65° C. at the respective pH, after which it was frozen. The other half was frozen immediately and served as the control.

Prior to measuring the residual protease activity, the samples were diluted ten times in 50 mM CHES-HEPES buffer, pH 8.5. The activity was determined using a modified version of the Protazyme AK assay of Example 1, solubilising one tablet of the substrate in 4 ml CHES-HEPES buffer, pH 8.5, mixing under continuous agitation one ml of this substrate solution with 20 ul of diluted protease sample, which was then incubated at 37° C. The substrate should have the correct temperature prior to adding protease. After 15 minutes the reaction was stopped by adding 100 ul 1M NaOH and the insoluble substrate was precipitated by centrifugation at 15000 rpm for 3 minutes after which the absorbance at 650 nm was measured. The values should be below OD 3.0, alternatively the protease sample should be diluted more than ten times prior to the activity measurement.

The relative residual activity (%) is calculated by dividing the activity after incubation at 65° C. with the activity of the corresponding control. The results of Table 1 below show that all four variants are of an improved thermostability as compared to Protease 10.

TABLE 1

Residual activity after incubation for four hours at 65° C.

| Protease | % Residual Actitivty pH 6 | % Residual Activity pH 4 |
|---|---|---|
| Protease 10 + N47D | 44 | 68 |
| Protease 10 + T127R | — | 77 |
| Protease 10 + N92K | — | 55 |
| Protease 10 + Q54R | 52 | 67 |
| Protease 10 | 19 | 41 |

Example 3

Protease Variant 22

A protease variant designated "Protease 22" and comprising a number of substitutions in thirteen of the seventeen regions specified in claim 1 was designed. This variant comprises the following substitutions as compared to the mature part of Protease 10 (amino acids 1-188 of SEQ ID NO: 2): T10Y, A25S, R38T, Q42P, T44S, R49K, Q54R, V56I, A62S, T82S, S99A, G118Ns, S120T, S122R, E125Q, T129Y, N130S, M131L, R165S, T166A, F171Y, T176N, V179L, N180S, V184L, and R185T.

The mature part of Protease 22 is amino acids 1-196 of SEQ ID NO: 21. The DNA sequence corresponding to SEQ ID NO: 21 is SEQ ID NO: 20.

The DNA sequence of SEQ ID NO: 20 was constructed and introduced into a *Bacillus* host for expression. The expressed protease was purified and characterized as an alpha-lytic protease (peptidase family S1E and/or S2A).

The temperature-activity relationship of Protease 22 was measured at pH9, using the Protazyme AK assay of Example 1, Protease 10 being included for comparative purposes. The results are shown in Table 2 below.

TABLE 2

Temperature profile at pH9 of Protease 22 and Protease 10

| | Relative activity at pH 9 | |
|---|---|---|
| Temperature (° C.) | Protease 22 | Protease 10 |
| 15 | 0.016 | 0.015 |
| 25 | 0.010 | 0.024 |
| 37 | 0.028 | 0.068 |
| 50 | 0.069 | 0.199 |
| 60 | 0.138 | 0.510 |
| 70 | 0.474 | 1.000 |
| 80 | 1.000 | 0.394 |
| 90 | 0.375 | — |

From these results it appears that Protease 22 has a higher temperature optimum at pH 9 than the Protease 10, viz. around 80° C. as compared to around 70° C.

Differential Scanning Calorimetry (DSC) was used to determine temperature stability at pH 7.0 of Protease 22 and Protease 10. The purified proteases were dialysed over night at 4° C. against 10 mM sodium phosphate, 50 mM sodium chloride, pH 7.0 and run on a VP-DSC instrument (Micro Cal) with a constant scan rate of 1.5° C./min from 20 to 100° C. Data-handling was performed using the MicroCal Origin software.

The resulting denaturation or melting temperatures, Tm's, were: For Protease 22: 83.5° C.; for Protease 10: 76.5° C.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. An isolated variant of a parent protease, comprising a substitution in at least one position selected from the group consisting of:

78-81; 83-86; 88-100; 103-106; 111-114; and 118-131; wherein (a) the variant has a sequence identity to the sequence of amino acids 1 to 188 of SEQ ID NO:2 of at least 90% but less than 100%;

(b) the variant has protease activity; and (c) each position corresponds to a position of amino acids 1 to 188 of SEQ ID NO:2.

2. The variant of claim 1, which has a sequence identity to the sequence of amino acids 1 to 188 of SEQ ID NO:2 of at least 92%.

3. The variant of claim 1, which has a sequence identity to the sequence of amino acids 1 to 188 of SEQ ID NO:2 of at least 94%.

4. The variant of claim 1, which has a sequence identity to the sequence of amino acids 1 to 188 of SEQ ID NO:2 of at least 95%.

5. The variant of claim 1, which has a sequence identity to the sequence of amino acids 1 to 188 of SEQ ID NO:2 of at least 96%.

6. The variant of claim 1, which has a sequence identity to the sequence of amino acids 1 to 188 of SEQ ID NO:2 of at least 97%.

7. The variant of claim 1, which has a sequence identity to the sequence of amino acids 1 to 188 of SEQ ID NO:2 of at least 98%.

8. The variant of claim 1, which comprises a substitution at position 78.

9. The variant of claim 1, which comprises a substitution at position 79.

10. The variant of claim 1, which comprises a substitution at position 80.

11. The variant of claim 1, which comprises a substitution at position 81.

12. The variant of claim 1, which comprises a substitution at position 83.

13. The variant of claim 1, which comprises a substitution at position 84.

14. The variant of claim 1, which comprises a substitution at position 85.

15. The variant of claim 1, which comprises a substitution at position 86.

16. The variant of claim 1, which further comprises a substitution at position 87 selected from the group consisting of T87A, T87C, T87D, T87E, T87F, T87G, T87H, T87I, T87K, T87L, T87M, T87N, T87P, T87Q, T87R, T87S, T87V, T87W, and T87Y.

17. The variant of claim 1, which comprises a substitution at position 88.

18. The variant of claim 1, which comprises a substitution at position 89.

19. The variant of claim 1, which comprises a substitution at position 90.

20. The variant of claim 1, which comprises a substitution at position 92.

21. The variant of claim 1, which comprises a substitution at position 93.

22. The variant of claim 1, which comprises a substitution at position 94.

23. The variant of claim 1, which comprises a substitution at position 95.

24. The variant of claim 1, which comprises a substitution at position 96.

25. The variant of claim 1, which comprises a substitution at position 97.

26. The variant of claim 1, which comprises a substitution at position 98.

27. The variant of claim 1, which comprises a substitution at position 99.

28. The variant of claim 1, which comprises a substitution at position 103.

29. The variant of claim 1, which comprises a substitution at position 105.

30. The variant of claim 1, which comprises a substitution at position 106.

31. The variant of claim 1, which comprises a substitution at position 111.

32. The variant of claim 1, which comprises a substitution at position 113.

33. The variant of claim 1, which comprises at least one of the following substitutions:
    78A, C, D, E, F, G, H, I, K, L, M, N, P, Q, R, T, V, W, Y;
    79A, C, D, E, F, G, H, I, K, L, M, N, P, Q, S, T, V, W, Y;
    80A, C, D, E, F, G, H, I, K, L, M, N, P, Q, R, S, T, V, W;
    81A, C, D, E, F, G, H, I, K, L, M, P, Q, R, S, T, V, W, Y;
    83A, C, D, E, F, H, I, K, L, M, N, P, Q, R, S, T, V, W, Y;
    84A, C, D, E, F, H, I, K, L, M, N, P, Q, R, S, T, V, W, Y;
    85A, C, D, E, F, G, H, I, K, L, M, N, P, Q, R, S, T, V, W;
    86C, D, E, F, G, H, I, K, L, M, N, P, R, S, T, V, W, Y;
    88A, C, D, E, F, G, H, I, K, L, M, N, P, Q, R, S, T, W, Y;
    89C, D, E, F, G, H, I, K, L, M, N, P, Q, R, V, W, Y;
    90A, C, D, E, F, H, I, K, L, M, N, P, Q, R, S, T, V, W, Y;
    92P, R, K;
    93P;
    94C, P;
    95E, D;
    96E, D, P;
    97R, K;
    98P;
    99R, K;
    103C;
    105C, P;
    106C;
    111R, K; and/or
    113E, D.

34. The variant of claim 1, which comprises at least one of the following pairs of substitutions: 6C+103C; 8C+105C; 76C+85C; 94C+149C; and/or 106C+141C.

35. The variant of claim 1, which comprises at least one of the following substitutions:
    81P; 92P; 93P; 94P; 96P; 98P; 105P; and/or 125P.

36. The variant of claim 1, which comprises at least one of the following substitutions:
    81E, D; 84E, D; 89E, D; 95E, D; 96E, D; 113E, D; 120E, D; 129E, D; and/or 130E, D.

37. The variant of claim 1, which comprises at least one of the following substitutions:
    92R, K; 97R, K; 99R, K; 111R, K; 118R, K; 122R, K; 124R, K; and/or 127R, K.

38. The variant of claim 1, which comprises at least one of the following substitutions:
    81P; 84D, E; 85C; 92P, R, K; 93P; 94C, P; 95E, D; 96E, D, P; 97R, K; 98P; 103C; 105C, P; 106C; 122R, K; 124R, K; and/or 127R, K.

39. The variant of claim 1, which comprises at least one of the following substitutions:
    S78A, C, D, E, F, G, H, I, K, L, M, N, P, Q, R, T, V, W, Y;
    R79A, C, D, E, F, G, H, I, K, L, M, N, P, Q, S, T, V, W, Y;
    Y80A, C, D, E, F, G, H, I, K, L, M, N, P, Q, R, S, T, V, W;
    N81A, C, D, E, F, G, H, I, K, L, M, P, Q, R, S, T, V, W, Y;
    G83A, C, D, E, F, H, I, K, L, M, N, P, Q, R, S, T, V, W, Y;
    G84A, C, D, E, F, H, I, K, L, M, N, P, Q, R, S, T, V, W, Y;
    Y85A, C, D, E, F, G, H, I, K, L, M, N, P, Q, R, S, T, V, W;
    A86C, D, E, F, G, H, I, K, L, M, N, P, Q, R, S, T, V, W, Y;
    V88A, C, D, E, F, G, H, I, K, L, M, N, P, Q, R, S, T, W, Y;
    A89C, D, E, F, G, H, I, K, L, M, N, P, Q, R, S, T, V, W, Y;
    G90A, C, D, E, F, H, I, K, L, M, N, P, Q, R, S, T, V, W, Y;
    H91T, S;
    N92P, R, K, S;
    Q93P;
    A94C, P;
    P95A, E, D;
    I96A, E, D, P;
    G97R, K;
    S98P;
    S99A, Q, R, K;
    V100I;
    S103C;
    S105C, P;
    T106C;
    C111R, K;
    T113E, D;
    I114V;
    G118N, R, K;
    S120T, E, D;
    S122R, K;
    P124R, K;
    E125P, Q;
    T127R, K;
    T129E, D, Y, Q;
    N130E, D; and/or
    M131L.

40. A detergent composition comprising a variant of claim 1 and a surfactant.

41. An animal feed additive comprising at least one variant of claim 1, and
    (a) at least one fat soluble vitamin;
    (b) at least one water soluble vitamin; and/or
    (c) at least one trace mineral.

42. An animal feed composition having a crude protein content of 50 to 800 g/kg and comprising a variant of claim 1.

43. A method for improving the nutritional value of an animal feed comprising at least one protein, comprising adding a variant of claim 1 to the animal feed in an amount adequate for improving the nutritional value of the animal feed.

44. A method for the proteolytic treatment of proteins, comprising
    a) adding a variant of claim 1 to a composition comprising proteins; and
    (b) incubating the composition and variant for a time sufficient for treating proteins in the composition.

45. An isolated nucleic acid sequence comprising a nucleic acid sequence which encodes a variant of claim 1.

46. A nucleic acid construct comprising the nucleic acid sequence of claim 45 operably linked to one or more control sequences that direct the production of the variant in a suitable expression host.

47. A recombinant expression vector comprising the nucleic acid construct of claim 46.

48. An isolated recombinant host cell comprising the nucleic acid construct of claim 46.

49. A method for producing a variant having protease activity, comprising:
   (a) cultivating the host cell of claim 48 to produce a supernatant comprising the variant; and
   (b) recovering the variant.

* * * * *

UNITED STATES PATENT AND TRADEMARK OFFICE
CERTIFICATE OF CORRECTION

| | | |
|---|---|---|
| PATENT NO. | : 7,892,808 B2 | Page 1 of 1 |
| APPLICATION NO. | : 10/574554 | |
| DATED | : February 22, 2011 | |
| INVENTOR(S) | : De Maria et al. | |

It is certified that error appears in the above-identified patent and that said Letters Patent is hereby corrected as shown below:

Column 82, line 43, delete "N130E, D;" and insert -- N130E, D, S; --

Signed and Sealed this
Nineteenth Day of April, 2011

David J. Kappos
*Director of the United States Patent and Trademark Office*